US008952218B2

(12) United States Patent
Ayal et al.

(10) Patent No.: US 8,952,218 B2
(45) Date of Patent: Feb. 10, 2015

(54) POLYNUCLEOTIDES, POLYPEPTIDES ENCODED THEREBY, AND METHODS OF USING SAME FOR INCREASING ABIOTIC STRESS TOLERANCE, BIOMASS AND/OR YIELD IN PLANTS EXPRESSING SAME

(75) Inventors: Sharon Ayal, Kiryat-Ekron (IL); Eyal Emmanuel, Rechovot (IL); Zur Granevitze, Petach-Tikva (IL); Alex Diber, Rishon-LeZion (IL); Basia Judith Vinocur, Rechovot (IL); Hagai Karchi, Moshav Sitriya (IL); Yoav Herschkovitz, Givataim (IL)

(73) Assignee: Evogene Ltd., Rechovot (IL)

( * ) Notice: Subject to any disclaimer, the term of this patent is extended or adjusted under 35 U.S.C. 154(b) by 196 days.

(21) Appl. No.: 13/139,729

(22) PCT Filed: Dec. 28, 2009

(86) PCT No.: PCT/IB2009/055962
§ 371 (c)(1),
(2), (4) Date: Jun. 15, 2011

(87) PCT Pub. No.: WO2010/076756
PCT Pub. Date: Jul. 8, 2010

(65) Prior Publication Data
US 2011/0265222 A1 Oct. 27, 2011

Related U.S. Application Data

(60) Provisional application No. 61/213,577, filed on Jun. 22, 2009, provisional application No. 61/193,830, filed on Dec. 29, 2008.

(51) Int. Cl.
C07K 14/415 (2006.01)
C12N 15/29 (2006.01)
C12N 15/82 (2006.01)
C12N 5/10 (2006.01)

(52) U.S. Cl.
CPC .......... C12N 15/8262 (2013.01); C07K 14/415 (2013.01); C12N 15/8271 (2013.01)
USPC .......................................... 800/290; 800/289

(58) Field of Classification Search
None
See application file for complete search history.

(56) References Cited

U.S. PATENT DOCUMENTS

| 6,084,153 | A  |   | 7/2000 | Good et al. |         |
|-----------|----|---|--------|-------------|---------|
| 7,214,786 | B2 |   | 5/2007 | Kovalic et al. |      |
| 2002/0046419 | A1 |   | 4/2002 | Choo et al. |       |
| 2004/0123343 | A1 | * | 6/2004 | La Rosa et al. | 800/278 |
| 2004/0172684 | A1 |   | 9/2004 | Kovalic et al. |    |
| 2005/0108791 | A1 |   | 5/2005 | Edgerton |          |
| 2006/0123516 | A1 | * | 6/2006 | Ronen et al. | 800/289 |
| 2006/0179511 | A1 |   | 8/2006 | Chomet et al. |       |
| 2007/0044171 | A1 | * | 2/2007 | Kovalic et al. | 800/278 |
| 2009/0144848 | A1 |   | 6/2009 | Kovalic et al. |    |

FOREIGN PATENT DOCUMENTS

| WO | WO 2004/081173 | 9/2004 |
|----|----------------|--------|
| WO | WO 2004/104162 | 12/2004 |
| WO | WO 2004/111183 | 12/2004 |
| WO | WO 2005/121364 | 12/2005 |
| WO | WO 2007/020638 | 2/2007 |
| WO | WO 2007/049275 | 5/2007 |
| WO | WO 2008/075364 | 6/2008 |
| WO | WO 2008/122980 | 10/2008 |
| WO | WO 2009/013750 | 1/2009 |
| WO | WO 2009/083958 | 7/2009 |
| WO | WO 2009/141824 | 11/2009 |
| WO | WO 2010/020941 | 2/2010 |
| WO | WO 2010/049897 | 5/2010 |
| WO | WO 2010/076756 | 7/2010 |
| WO | WO 2010/100595 | 9/2010 |
| WO | WO 2010/143138 | 12/2010 |
| WO | WO 2011/015985 | 2/2011 |
| WO | WO 2011/080674 | 7/2011 |
| WO | WO 2011/135527 | 11/2011 |
| WO | WO 2012/028993 | 3/2012 |
| WO | WO 2012/085862 | 6/2012 |
| WO | WO 2012/150598 | 11/2012 |
| WO | WO 2013/027223 | 2/2013 |
| WO | WO 2013/080203 | 6/2013 |
| WO | WO 2013/098819 | 7/2013 |
| WO | WO 2013/128448 | 9/2013 |
| WO | WO 2013/179211 | 12/2013 |
| WO | WO 2014/033714 | 3/2014 |

(Continued)

OTHER PUBLICATIONS

GenBank Accession No. XM_002459047.1. Sorghum Bicolor hypothetical protein. Published Jun. 25, 2009. pp. 1-2.*
GenBank Accession No. XP_002459092.1. Sorghum Bicolor hypothetical protein. Published Jun. 25, 2009. pp. 1-2.*
Schulze et al. Environment as stress factor: stress physiology of plants. Plant Ecology. 2005. 702: 7-11.*
International Preliminary Report on Patentability Dated Jul. 7, 2011 From the International Bureau of WIPO Re. Application No. PCT/IB2009/055962.
International Search Report and the Written Opinion Dated Nov. 8, 2010 From the International Searching Authority Re. Application No. PCT/EB09/55962.

(Continued)

Primary Examiner — Brent T Page
Assistant Examiner — Ashley K Buran

(57) ABSTRACT

Provided are isolated polynucleotides comprising a nucleic acid sequence at least 80% identical to SEQ ID NO:619, 617, 606, 615, 629, 1-36, 40, 41, 43-45, 49, 52-56, 58, 113-343, 351, 354-358, 605, 607-614, 616, 618, 620-628, 630-638, 642, 645, 650, 651, 670, or 671. Also provided are nucleic acid constructs comprising same, isolated polypeptides encoded thereby, transgenic cells and transgenic plants comprising same and methods of using same for increasing abiotic stress tolerance, yield, biomass, growth rate, vigor, oil content, fiber yield, fiber quality, and/or nitrogen use efficiency of a plant.

21 Claims, 3 Drawing Sheets

(56) References Cited

FOREIGN PATENT DOCUMENTS

WO WO 2014/102773 7/2014
WO WO 2014/102774 7/2014

OTHER PUBLICATIONS

Invitation to Pay Additional Fees Dated Sep. 7, 2010 From the International Searching Authority Re. Application No. PCT/IB09/55962.
Communication Pursuant to Article 94(3) EPC Dated Mar. 8, 2013 From the European Patent Office Re. Application No. 09836167.8.
Supplementary European Search Report and the European Search Opinion Dated Apr. 26, 2012 From the European Patent Office Re. Application No. 09836167.8.
Cordonnier-Pratt et al. "WS1_13_A12.g1_A002 Water-Stressed 1 (WS1) Sorghum Bicolor cDNA, mRNA Sequence", Database EMBL [Online], XP002673839, Retrieved From EBI Accession No. EMBL:AW678130, Database Accession No. AW678130, Apr. 16, 2000.
Paterson et al. "SubName: Full=Putative Uncharacterized Protein Sb03g045710", Database UniProtKB [Online], XP002673840, Retrieved From EBI Accession No. UNIPROT:C5XHU4, Database Accession No. C5XHU4, Sep. 1, 2009.
Communication Pursuant to Rules 70(2) and 70a(2) EPC Dated May 15, 2012 From the European Patent Office Re. Application No. 09836167.8.
Communication Pursuant to Article 94(3) EPC Dated May 20, 2014 From the European Patent Office Re. Application No. 09836167.8.
Yanagisawa et al. "Metabolic Engineering With Dof1 Transcription Factor in Plants: Improved Nitrogen Assimilation and Growth Under Low-Nitrogen Conditions", Proc. Natl. Acad. Sci USA, PNAS, 101(20): 7833-7838, May 18, 2004.

* cited by examiner

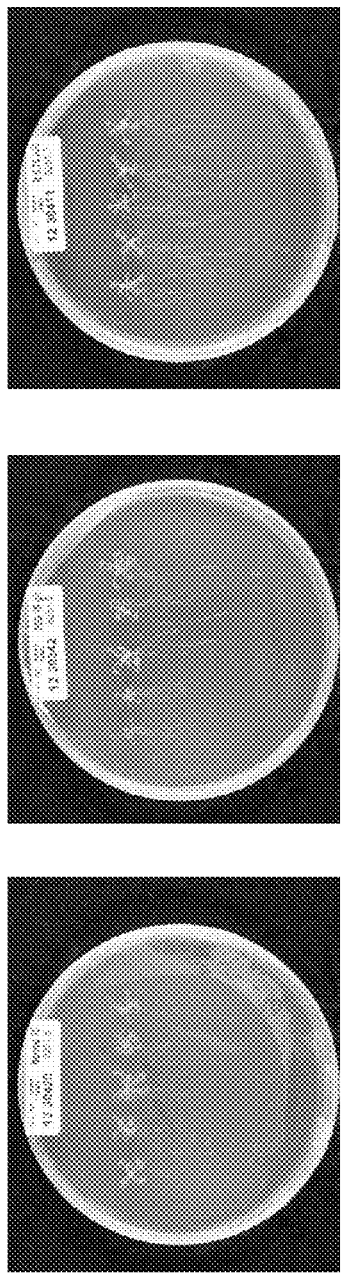
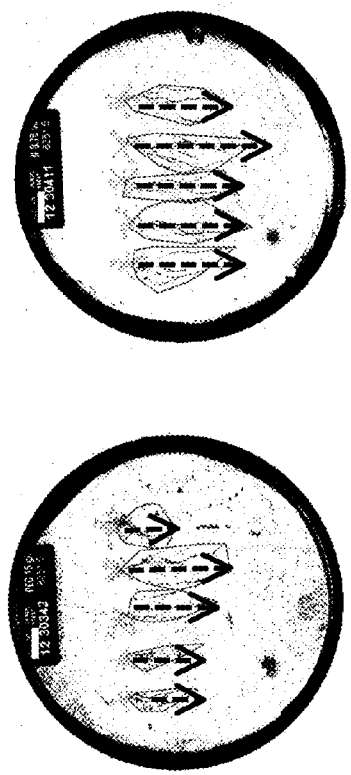
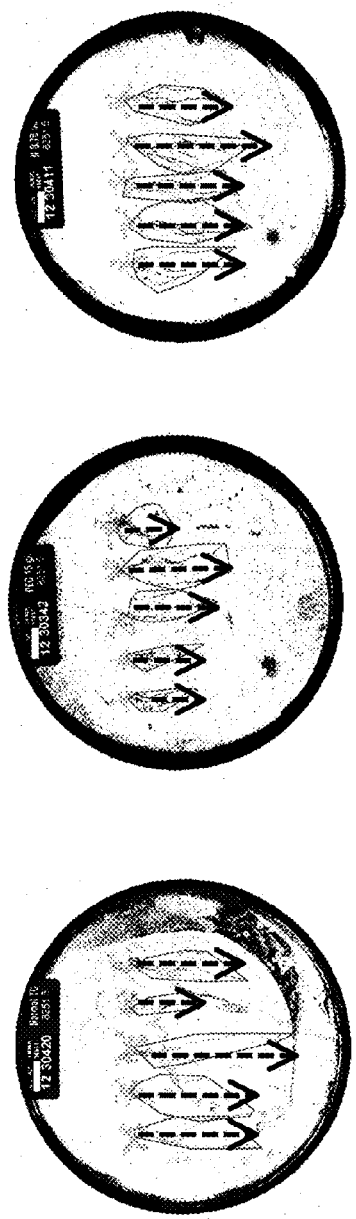

POLYNUCLEOTIDES, POLYPEPTIDES ENCODED THEREBY, AND METHODS OF USING SAME FOR INCREASING ABIOTIC STRESS TOLERANCE, BIOMASS AND/OR YIELD IN PLANTS EXPRESSING SAME

RELATED APPLICATIONS

This application is a National Phase of PCT Patent Application No. PCT/IB2009/055962 having International filing date of Dececember 28, 2009, which claims the benefit of priority of U.S. Provisional Patent Application Nos. 61/213,577 filed on Jun. 22, 2009; and 61/193,830 filed on Dec. 29, 2008. The contents of the above applications are all incorporated herein by reference.

FIELD AND BACKGROUND OF THE INVENTION

The present invention, in some embodiments thereof, relates to isolated polypeptides and polynucleotides, nucleic acid constructs comprising same, transgenic cells comprising same, transgenic plants exogenously expressing same and more particularly, but not exclusively, to methods of using same for increasing abiotic stress tolerance, growth rate, biomass, vigor, yield (e.g., seed yield, oil yield), oil content, fiber yield, fiber quality and/or fertilizer use efficiency (e.g., nitrogen use efficiency) of a plant.

Abiotic stress (ABS; also referred to as "environmental stress") conditions such as salinity, drought, flood, suboptimal temperature and toxic chemical pollution, cause substantial damage to agricultural plants. Most plants have evolved strategies to protect themselves against these conditions. However, if the severity and duration of the stress conditions are too great, the effects on plant development, growth and yield of most crop plants are profound. Furthermore, most of the crop plants are highly susceptible to abiotic stress and thus necessitate optimal growth conditions for commercial crop yields. Continuous exposure to stress causes major alterations in the plant metabolism which ultimately leads to cell death and consequently yield losses.

The global shortage of water supply is one of the most severe agricultural problems affecting plant growth and crop yield and efforts are made to mitigate the harmful effects of desertification and salinization of the world's arable land. Water deficit is a common component of many plant stresses and occurs in plant cells when the whole plant transpiration rate exceeds the water uptake. In addition to drought, other stresses, such as salinity and low temperature, produce cellular dehydration.

Drought is a gradual phenomenon, which involves periods of abnormally dry weather that persists long enough to produce serious hydrologic imbalances such as crop damage and water supply shortage. In severe cases, drought can last many years and results in devastating effects on agriculture and water supplies. Furthermore, drought is associated with increase susceptibility to various diseases.

For most crop plants, the land regions of the world are too arid. In addition, overuse of available water results in increased loss of agriculturally-usable land (desertification), and increase of salt accumulation in soils adds to the loss of available water in soils.

Salinity, high salt levels, affects one in five hectares of irrigated land. This condition is only expected to worsen, further reducing the availability of arable land and crop production, since none of the top five food crops, i.e., wheat, corn, rice, potatoes, and soybean, can tolerate excessive salt.

Detrimental effects of salt on plants result from both water deficit which leads to osmotic stress (similar to drought stress) and the effect of excess sodium ions on critical biochemical processes. As with freezing and drought, high salt causes water deficit; and the presence of high salt makes it difficult for plant roots to extract water from their environment. Soil salinity is thus one of the more important variables that determine whether a plant may thrive. In many parts of the world, sizable land areas are uncultivable due to naturally high soil salinity. Thus, salination of soils that are used for agricultural production is a significant and increasing problem in regions that rely heavily on agriculture, and is worsen by over-utilization, over-fertilization and water shortage, typically caused by climatic change and the demands of increasing population. Salt tolerance is of particular importance early in a plant's lifecycle, since evaporation from the soil surface causes upward water movement, and salt accumulates in the upper soil layer where the seeds are placed. On the other hand, germination normally takes place at a salt concentration which is higher than the mean salt level in the whole soil profile.

Germination of many crops is sensitive to temperature. A gene that would enhance germination in hot conditions would be useful for crops that are planted late in the season or in hot climates. In addition, seedlings and mature plants that are exposed to excess heat may experience heat shock, which may arise in various organs, including leaves and particularly fruit, when transpiration is insufficient to overcome heat stress. Heat also damages cellular structures, including organelles and cytoskeleton, and impairs membrane function. Heat shock may produce a decrease in overall protein synthesis, accompanied by expression of heat shock proteins, e.g., chaperones, which are involved in refolding proteins denatured by heat.

Heat stress often accompanies conditions of low water availability. Heat itself is seen as an interacting stress and adds to the detrimental effects caused by water deficit conditions. Water evaporation increases along with the rise in daytime temperatures and can result in high transpiration rates and low plant water potentials. High-temperature damage to pollen almost always occurs in conjunction with drought stress, and rarely occurs under well-watered conditions. Combined stress can alter plant metabolism in various ways; therefore understanding the interaction between different stresses may be important for the development of strategies to enhance stress tolerance by genetic manipulation.

Excessive chilling conditions, e.g., low, but above freezing, temperatures affect crops of tropical origins, such as soybean, rice, maize, and cotton. Typical chilling damage includes wilting, necrosis, chlorosis or leakage of ions from cell membranes. The underlying mechanisms of chilling sensitivity are not completely understood yet, but probably involve the level of membrane saturation and other physiological deficiencies. For example, photoinhibition of photosynthesis (disruption of photosynthesis due to high light intensities) often occurs under clear atmospheric conditions subsequent to cold late summer/autumn nights. In addition, chilling may lead to yield losses and lower product quality through the delayed ripening of maize.

Salt and drought stress signal transduction consist of ionic and osmotic homeostasis signaling pathways. The ionic aspect of salt stress is signaled via the SOS pathway where a calcium-responsive SOS3-SOS2 protein kinase complex controls the expression and activity of ion transporters such as SOS1. The osmotic component of salt stress involves complex plant reactions that overlap with drought and/or cold stress responses.

Common aspects of drought, cold and salt stress response [Reviewed in Xiong and Zhu (2002) Plant Cell Environ. 25: 131-139] include: (a) transient changes in the cytoplasmic calcium levels early in the signaling event; (b) signal transduction via mitogen-activated and/or calcium dependent protein kinases (CDPKs) and protein phosphatases; (c) increases in abscisic acid levels in response to stress triggering a subset of responses; (d) inositol phosphates as signal molecules (at least for a subset of the stress responsive transcriptional changes; (e) activation of phospholipases which in turn generates a diverse array of second messenger molecules, some of which might regulate the activity of stress responsive kinases; (f) induction of late embryogenesis abundant (LEA) type genes including the CRT/DRE responsive COR/RD genes; (g) increased levels of antioxidants and compatible osmolytes such as proline and soluble sugars; and (h) accumulation of reactive oxygen species such as superoxide, hydrogen peroxide, and hydroxyl radicals. Abscisic acid biosynthesis is regulated by osmotic stress at multiple steps. Both ABA-dependent and -independent osmotic stress signaling first modify constitutively expressed transcription factors, leading to the expression of early response transcriptional activators, which then activate downstream stress tolerance effector genes.

Several genes which increase tolerance to cold or salt stress can also improve drought stress protection, these include for example, the transcription factor AtCBF/DREB1, OsCDPK7 (Saijo et al. 2000, Plant J. 23: 319-327) or AVP1 (a vacuolar pyrophosphatase-proton pump, Gaxiola et al. 2001, Proc. Natl. Acad. Sci. USA 98: 11444-11449).

Developing stress-tolerant plants is a strategy that has the potential to solve or mediate at least some of these problems. However, traditional plant breeding strategies used to develop new lines of plants that exhibit tolerance to ABS are relatively inefficient since they are tedious, time consuming and of unpredictable outcome. Furthermore, limited germplasm resources for stress tolerance and incompatibility in crosses between distantly related plant species represent significant problems encountered in conventional breeding. Additionally, the cellular processes leading to ABS tolerance are complex in nature and involve multiple mechanisms of cellular adaptation and numerous metabolic pathways.

Genetic engineering efforts, aimed at conferring abiotic stress tolerance to transgenic crops, have been described in various publications [Apse and Blumwald (Curr Opin Biotechnol. 13:146-150, 2002), Quesada et al. (Plant Physiol. 130:951-963, 2002), Holmström et al. (Nature 379: 683-684, 1996), Xu et al. (Plant Physiol 110: 249-257, 1996), Pilon-Smits and Ebskamp (Plant Physiol 107: 125-130, 1995) and Tarczynski et al. (Science 259: 508-510, 1993)].

Various patents and patent applications disclose genes and proteins which can be used for increasing tolerance of plants to abiotic stresses. These include for example, U.S. Pat. Nos. 5,296,462 and 5,356,816 (for increasing tolerance to cold stress); U.S. Pat. No. 6,670,528 (for increasing ABST); U.S. Pat. No. 6,720,477 (for increasing ABST); U.S. application Ser. Nos. 09/938,842 and 10/342,224 (for increasing ABST); U.S. application Ser. No. 10/231,035 (for increasing ABST); WO2004/104162 (for increasing ABST and biomass); WO2007/020638 (for increasing ABST, biomass, vigor and/or yield); WO2007/049275 (for increasing ABST, biomass, vigor and/or yield).

Suboptimal nutrient (macro and micro nutrient) affect plant growth and development through the whole plant life cycle. One of the essential macronutrients for the plant is Nitrogen. Nitrogen is responsible for biosynthesis of amino acids and nucleic acids, prosthetic groups, plant hormones, plant chemical defenses, and the like. Nitrogen is often the rate-limiting element in plant growth and all field crops have a fundamental dependence on inorganic nitrogenous fertilizer. Since fertilizer is rapidly depleted from most soil types, it must be supplied to growing crops two or three times during the growing season. Additional important macronutrients are Phosphorous (P) and Potassium (K), which have a direct correlation to yield and general plant tolerance.

Vegetable or seed oils are the major source of energy and nutrition in human and animal diet. They are also used for the production of industrial products, such as paints, inks and lubricants. In addition, plant oils represent renewable sources of long-chain hydrocarbons which can be used as fuel. Since the currently used fossil fuels are finite resources and are gradually being depleted, fast growing biomass crops may be used as alternative fuels or for energy feedstocks and may reduce the dependence on fossil energy supplies. However, the major bottleneck for increasing consumption of plant oils as bio-fuel is the oil price, which is still higher than fossil fuel. In addition, the production rate of plant oil is limited by the availability of agricultural land and water. Thus, increasing plant oil yields from the same growing area can effectively overcome the shortage in production space and can decrease vegetable oil prices at the same time.

Studies aiming at increasing plant oil yields focus on the identification of genes involved in oil metabolism as well as in genes capable of increasing plant and seed yields in transgenic plants. Genes known to be involved in increasing plant oil yields include those participating in fatty acid synthesis or sequestering such as desaturase [e.g., DELTA6, DELTA12 or acyl-ACP (Ssi2; Arabidopsis Information Resource (TAIR; Hypertext Transfer Protocol://World Wide Web (dot) arabidopsis (dot) org/), TAIR No. AT2G43710)], OleosinA (TAIR No. AT3G01570) or FAD3 (TAIR No. AT2G29980), and various transcription factors and activators such as Lec1 [TAIR No. AT1G21970, Lotan et al. 1998. Cell. 26; 93 (7): 1195-205], Lec2 [TAIR No. AT1G28300, Santos Mendoza et al. 2005, FEBS Lett. 579 (21):4666-70], Fus3 (TAIR No. AT3G26790), ABI3 [TAIR No. AT3G24650, Lara et al. 2003. J Biol. Chem. 278 (23): 21003-11] and Wri1 [TAIR No. AT3G54320, Cernac and Benning, 2004. Plant J. 40 (4): 575-85].

Genetic engineering efforts aiming at increasing oil content in plants (e.g., in seeds) include upregulating endoplasmic reticulum (FAD3) and plastidal (FAD7) fatty acid desaturases in potato (Zabrouskov V., et al., 2002; Physiol Plant. 116:172-185); over-expressing the GmDof4 and GmDof11 transcription factors (Wang H W et al., 2007; Plant J. 52:716-29); over-expressing a yeast glycerol-3-phosphate dehydrogenase under the control of a seed-specific promoter (Vigeolas H, et al. 2007, Plant Biotechnol J. 5:431-41; U.S. Pat. Appl. No. 20060168684); using Arabidopsis FAE1 and yeast SLC1-1 genes for improvements in erucic acid and oil content in rapeseed (Katavic V, et al., 2000, Biochem Soc Trans. 28:935-7).

Various patent applications disclose genes and proteins which can increase oil content in plants. These include for example, U.S. Pat. Appl. No. 20080076179 (lipid metabolism protein); U.S. Pat. Appl. No. 20060206961 (the Ypr140w polypeptide); U.S. Pat. Appl. No. 20060174373 [triacylglycerols synthesis enhancing protein (TEP)]; U.S. Pat. Appl. Nos. 20070169219, 20070006345, 20070006346 and 20060195943 (disclose transgenic plants with improved nitrogen use efficiency which can be used for the conversion into fuel or chemical feedstocks); WO2008/122980 (polynucleotides for increasing oil content, growth rate, biomass, yield and/or vigor of a plant).

Cotton and cotton by-products provide raw materials that are used to produce a wealth of consumer-based products in addition to textiles including cotton foodstuffs, livestock feed, fertilizer and paper. The production, marketing, consumption and trade of cotton-based products generate an excess of $100 billion annually in the U.S. alone, making cotton the number one value-added crop.

Even though 90% of cotton's value as a crop resides in the fiber (lint), yield and fiber quality has declined due to general erosion in genetic diversity of cotton varieties, and an increased vulnerability of the crop to environmental conditions.

There are many varieties of cotton plant, from which cotton fibers with a range of characteristics can be obtained and used for various applications. Cotton fibers may be characterized according to a variety of properties, some of which are considered highly desirable within the textile industry for the production of increasingly high quality products and optimal exploitation of modem spinning technologies. Commercially desirable properties include length, length uniformity, fineness, maturity ratio, decreased fuzz fiber production, micronaire, bundle strength, and single fiber strength. Much effort has been put into the improvement of the characteristics of cotton fibers mainly focusing on fiber length and fiber fineness. In particular, there is a great demand for cotton fibers of specific lengths.

A cotton fiber is composed of a single cell that has differentiated from an epidermal cell of the seed coat, developing through four stages, i.e., initiation, elongation, secondary cell wall thickening and maturation stages. More specifically, the elongation of a cotton fiber commences in the epidermal cell of the ovule immediately following flowering, after which the cotton fiber rapidly elongates for approximately 21 days. Fiber elongation is then terminated, and a secondary cell wall is formed and grown through maturation to become a mature cotton fiber.

Several candidate genes which are associated with the elongation, formation, quality and yield of cotton fibers were disclosed in various patent applications such as U.S. Pat. No. 5,880,100 and U.S. patent application Ser. Nos. 08/580,545, 08/867,484 and 09/262,653 (describing genes involved in cotton fiber elongation stage); WO0245485 (improving fiber quality by modulating sucrose synthase); U.S. Pat. No. 6,472,588 and WO01/17333 (increasing fiber quality by transformation with a DNA encoding sucrose phosphate synthase); WO9508914 (using a fiber-specific promoter and a coding sequence encoding cotton peroxidase); WO9626639 (using an ovary specific promoter sequence to express plant growth modifying hormones in cotton ovule tissue, for altering fiber quality characteristics such as fiber dimension and strength); U.S. Pat. No. 5,981,834, U.S. Pat. No. 5,597,718, U.S. Pat. No. 5,620,882, U.S. Pat. No. 5,521,708 and U.S. Pat. No. 5,495,070 (coding sequences to alter the fiber characteristics of transgenic fiber producing plants); U.S. patent applications U.S. 2002049999 and U.S. 2003074697 (expressing a gene coding for endoxyloglucan transferase, catalase or peroxidase for improving cotton fiber characteristics); WO 01/40250 (improving cotton fiber quality by modulating transcription factor gene expression); WO 96/40924 (a cotton fiber transcriptional initiation regulatory region associated which is expressed in cotton fiber); EP0834566 (a gene which controls the fiber formation mechanism in cotton plant); WO2005/121364 (improving cotton fiber quality by modulating gene expression); WO2008/075364 (improving fiber quality, yield/biomass/vigor and/or abiotic stress tolerance of plants).

SUMMARY OF THE INVENTION

According to an aspect of some embodiments of the present invention there is provided a method of increasing abiotic stress tolerance, yield, biomass, growth rate, vigor, oil content, fiber yield, fiber quality, and/or nitrogen use efficiency of a plant, comprising expressing within the plant an exogenous polynucleotide comprising a nucleic acid sequence at least 80% identical to SEQ ID NO:619, 617, 606, 615, 629, 1-36, 40, 41, 43-45, 49, 52-56, 58, 113-343, 351, 354-358, 605, 607-614, 616, 618, 620-628, 630-638, 642, 645, 650, 651, 670, or 671, thereby increasing the abiotic stress tolerance, yield, biomass, growth rate, vigor, oil content, fiber yield, fiber quality, and/or nitrogen use efficiency of the plant.

According to an aspect of some embodiments of the present invention there is provided a method of increasing abiotic stress tolerance, yield, biomass, growth rate, vigor, oil content, fiber yield, fiber quality, and/or nitrogen use efficiency of a plant, comprising expressing within the plant an exogenous polynucleotide comprising the nucleic acid sequence selected from the group consisting of SEQ ID NOs: 619, 617, 606, 615, 629, 1-49, 51-59, 113-343, 345-351, 353-358, 605, 607-614, 616, 618, 620-628, 630-638, 641, 642, 644, 644-646, 648-651, 670, and 671, thereby increasing the abiotic stress tolerance, yield, biomass, growth rate, vigor, oil content, fiber yield, fiber quality, and/or nitrogen use efficiency of the plant.

According to an aspect of some embodiments of the present invention there is provided a method of increasing abiotic stress tolerance, nitrogen use efficiency, fiber yield and/or fiber quality of a plant, comprising expressing within the plant an exogenous polynucleotide comprising a nucleic acid sequence at least 80% identical to SEQ ID NO: 352, 639, 640, or 643, thereby increasing the abiotic stress tolerance, nitrogen use efficiency, fiber yield and/or fiber quality of the plant.

According to an aspect of some embodiments of the present invention there is provided a method of increasing nitrogen use efficiency, seed yield and/or oil content of a plant, comprising expressing within the plant an exogenous polynucleotide comprising a nucleic acid sequence at least 80% identical to SEQ ID NO: 50, 645, or 647, thereby increasing the nitrogen use efficiency, seed yield and/or oil content of the plant.

According to an aspect of some embodiments of the present invention there is provided a method of increasing seed yield, fiber yield and/or fiber quality of a plant, comprising expressing within the plant an exogenous polynucleotide comprising a nucleic acid sequence at least 80% identical to SEQ ID NO:344, thereby increasing the seed yield, fiber yield and/or fiber quality of the plant.

According to an aspect of some embodiments of the present invention there is provided a method of increasing abiotic stress tolerance, yield, biomass, growth rate, vigor, oil content, fiber yield, fiber quality, and/or nitrogen use efficiency of a plant, comprising expressing within the plant an exogenous polynucleotide comprising a nucleic acid sequence encoding a polypeptide at least 80% identical to SEQ ID NO:75, 73, 652, 71, 86, 60-70, 72, 74, 76-85, 87-95, 108-109, 112, 359-589, 602-604, 653-660, 665, 668, or 672, thereby increasing the abiotic stress tolerance, yield, biomass, growth rate, vigor, oil content, fiber yield, fiber quality, and/or nitrogen use efficiency of the plant.

According to an aspect of some embodiments of the present invention there is provided a method of increasing abiotic stress tolerance, yield, biomass, growth rate, vigor, oil content, fiber yield, fiber quality, and/or nitrogen use efficiency of a plant, comprising expressing within the plant an exogenous polynucleotide comprising a nucleic acid sequence encoding a polypeptide selected from the group consisting of SEQ ID NOs:75, 73, 652, 71, 86, 60-70, 72, 74, 76-85, 87-98, 100-109, 111, 112, 359-589, 591-597, 600-604, 653-662, 664, 666-669, and 672, thereby increasing the abiotic stress tolerance, yield, biomass, growth rate, vigor, oil content, fiber yield, fiber quality, and/or nitrogen use efficiency of the plant.

According to an aspect of some embodiments of the present invention there is provided a method of increasing abiotic stress tolerance, nitrogen use efficiency, fiber yield and/or fiber quality of a plant, comprising expressing within the plant an exogenous polynucleotide comprising a nucleic acid sequence encoding a polypeptide at least 80% identical to SEQ ID NO:99 or 598, thereby increasing the abiotic stress tolerance, nitrogen use efficiency, fiber yield and/or fiber quality of the plant.

According to an aspect of some embodiments of the present invention there is provided a method of increasing nitrogen use efficiency, seed yield and/or oil content of a plant, comprising expressing within the plant an exogenous polynucleotide comprising a nucleic acid sequence encoding a polypeptide at least 80% identical to SEQ ID NO:599 or 663, thereby increasing the nitrogen use efficiency, seed yield and/or oil content of the plant.

According to an aspect of some embodiments of the present invention there is provided a method of increasing nitrogen use efficiency, abiotic stress tolerance, seed yield and/or oil content of a plant, comprising expressing within the plant an exogenous polynucleotide comprising a nucleic acid sequence encoding a polypeptide at least 80% identical to SEQ ID NO:110 or 665, thereby increasing the nitrogen use efficiency, abiotic stress tolerance, seed yield and/or oil content of the plant.

According to an aspect of some embodiments of the present invention there is provided a method of increasing seed yield, fiber yield and/or fiber quality of a plant, comprising expressing within the plant an exogenous polynucleotide comprising a nucleic acid sequence encoding a polypeptide at least 80% identical to SEQ ID NO:590, thereby increasing the seed yield, fiber yield and/or fiber quality of the plant.

According to an aspect of some embodiments of the present invention there is provided an isolated polynucleotide comprising a nucleic acid sequence at least 80% identical to SEQ ID NO:619, 617, 606, 615, 629, 1-36, 40, 41, 43-45, 49, 52-56, 58, 113-343, 351, 354-358, 605, 607-614, 616, 618, 620-628, 630-638, 642, 645, 650-651, 670, or 671, wherein said nucleic acid sequence is capable of increasing abiotic stress tolerance, yield, biomass, growth rate, vigor, oil content, fiber yield, fiber quality, and/or nitrogen use efficiency of a plant.

According to an aspect of some embodiments of the present invention there is provided an isolated polynucleotide comprising the nucleic acid sequence selected from the group consisting of SEQ ID NOs:619, 617, 606, 615, 629, 1-49, 51-59, 113-343, 345-351, 353-358, 605, 607-614, 616, 618, 620-628, 630-638, 641, 642, 644, 644-646, 648-651, 670, and 671.

According to an aspect of some embodiments of the present invention there is provided an isolated polynucleotide comprising a nucleic acid sequence encoding a polypeptide which comprises an amino acid sequence at least 80% homologous to the amino acid sequence set forth in SEQ ID NO: 75, 73, 652, 71, 86, 60-70, 72, 74, 76-85, 87-95, 108-109, 112, 359-589, 602-604, 653-660, 665, 668, or 672, wherein said amino acid sequence is capable of increasing abiotic stress tolerance, yield, biomass, growth rate, vigor, oil content, fiber yield, fiber quality, and/or nitrogen use efficiency of a plant.

According to an aspect of some embodiments of the present invention there is provided an isolated polynucleotide comprising a nucleic acid sequence encoding a polypeptide which comprises the amino acid sequence selected from the group consisting of SEQ ID NOs:75, 73, 652, 71, 86, 60-70, 72, 74, 76-85, 87-98, 100-109, 111, 112, 359-589, 591-597, 600-604, 653-662, 664, 666-669, and 672.

According to an aspect of some embodiments of the present invention there is provided a nucleic acid construct comprising the isolated polynucleotide of claim 12, 13, 14 or 15, and a promoter for directing transcription of said nucleic acid sequence in a host cell.

According to an aspect of some embodiments of the present invention there is provided an isolated polypeptide comprising an amino acid sequence at least 80% homologous to SEQ ID NO:75, 73, 652, 71, 86, 60-70, 72, 74, 76-85, 87-95, 108-109, 112, 359-589, 602-604, 653-660, 665, 668, or 672, wherein said amino acid sequence is capable of increasing abiotic stress tolerance, yield, biomass, growth rate, vigor, oil content, fiber yield, fiber quality, and/or nitrogen use efficiency of a plant.

According to an aspect of some embodiments of the present invention there is provided an isolated polypeptide comprising the amino acid sequence selected from the group consisting of SEQ ID NOs:75, 73, 652, 71, 86, 60-70, 72, 74, 76-85, 87-98, 100-109, 111, 112, 359-589, 591-597, 600-604, 653-662, 664, 666-669, and 672

According to an aspect of some embodiments of the present invention there is provided a plant cell exogenously expressing the polynucleotide of claim 12, 13, 14 or 15, or the nucleic acid construct of claim 16.

According to an aspect of some embodiments of the present invention there is provided a plant cell exogenously expressing the polypeptide of claim 17 or 18.

According to some embodiments of the invention, the nucleic acid sequence is as set forth in SEQ ID NO:619, 617, 606, 615, 629, 1-36, 40, 41, 43-45, 49, 52-56, 58, 113-343, 351, 354-358, 605, 607-614, 616, 618, 620-628, 630-638, 642, 645, 650, 651, 670, or 671.

According to some embodiments of the invention, the polynucleotide consists of the nucleic acid sequence selected from the group consisting of SEQ ID NOs:619, 617, 606, 615, 629, 1-36, 40, 41, 43-45, 49, 52-56, 58, 113-343, 351, 354-358, 605, 607-614, 616, 618, 620-628, 630-638, 642, 645, 650, 651, 670, and 671.

According to some embodiments of the invention, the nucleic acid sequence encodes an amino acid sequence at least 80% homologous to SEQ ID NO:75, 73, 652, 71, 86, 60-70, 72, 74, 76-85, 87-95, 108-109, 112, 359-589, 602-604, 653-660, 665, 668, or 672.

According to some embodiments of the invention, the nucleic acid sequence encodes the amino acid sequence selected from the group consisting of SEQ ID NOs:75, 73, 652, 71, 86, 60-70, 72, 74, 76-85, 87-95, 108-109, 112, 359-589, 602-604, 653-660, 665, 668, and 672.

According to some embodiments of the invention, the plant cell forms part of a plant.

According to some embodiments of the invention, the method further comprising growing the plant expressing said exogenous polynucleotide under the abiotic stress.

According to some embodiments of the invention, the abiotic stress is selected from the group consisting of salinity, drought, water deprivation, flood, etiolation, low temperature, high temperature, heavy metal toxicity, anaerobiosis, nutrient deficiency, nutrient excess, atmospheric pollution and UV irradiation.

According to some embodiments of the invention, the yield comprises seed yield or oil yield.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3A-F are images depicting visualization of root development of transgenic plants exogenously expressing the polynucleotide of some embodiments of the invention when grown in transparent agar plates under normal (FIGS. 3A-B), osmotic stress (15% PEG; FIGS. 3C-D) or nitrogen-limiting (FIGS. 3E-F) conditions. The different transgenes were grown in transparent agar plates for 17 days (7 days nursery and 10 days after transplanting). The plates were photographed every 3-4 days starting at day 1 after transplanting. FIG. 3A—An image of a photograph of plants taken following 10 after transplanting days on agar plates when grown under normal (standard) conditions. FIG. 3B—An image of root analysis of the plants shown in FIG. 3A in which the lengths of the roots measured are represented by arrows. FIG. 3C—An image of a photograph of plants taken following 10 days after transplanting on agar plates, grown under high osmotic (PEG 15%) conditions. FIG. 3D—An image of root analysis of the plants shown in FIG. 3C in which the lengths of the roots measured are represented by arrows. FIG. 3E—An image of a photograph of plants taken following 10 days after transplanting on agar plates, grown under low nitrogen conditions. FIG. 3F—An image of root analysis of the plants shown in FIG. 3E in which the lengths of the roots measured are represented by arrows.

DESCRIPTION OF SPECIFIC EMBODIMENTS OF THE INVENTION

Figure 1:
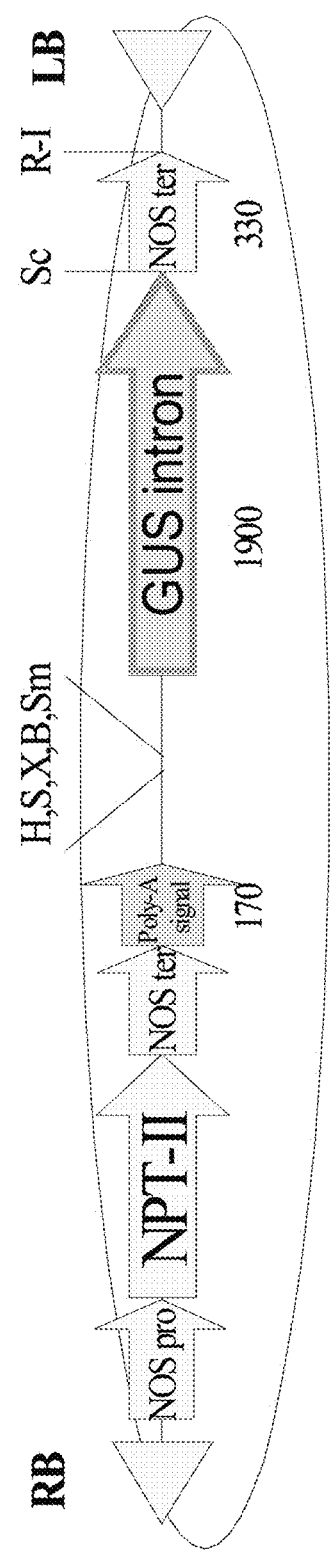
FIG. 1 is a schematic illustration of the pGI binary plasmid used for expressing the isolated polynucleotide sequences of some embodiments of the invention. RB—T-DNA right border; LB—T-DNA left border; H—HindIII restriction enzyme; X—XbaI restriction enzyme; B—BamHI restriction enzyme; S—SaiI restriction enzyme; Sm—SmaI restriction enzyme; R-I—EcoRI restriction enzyme; Sc—SacI/SstI/Ecl136II; (numbers)—Length in base-pairs; NOS pro=nopaline synthase promoter; NPT-II=neomycin phosphotransferase gene; NOS ter=nopaline synthase terminator; Poly-A signal (polyadenylation signal); GUSintron—the GUS reporter gene (coding sequence and intron) The isolated polynucleotide sequences of the invention were cloned into the vector while replacing the GUSintron reporter gene

The present invention relates to polypeptides, polynucleotides, nucleic acid constructs and methods of increasing abiotic stress tolerance, fertilizer use efficiency (e.g., nitrogen use efficiency), growth, biomass, fiber development or quality, vigor and/or yield of a plant.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have identified novel polypeptides and polynucleotides which can be used to increase abiotic stress tolerance, yield, biomass, growth rate, vigor, oil content, fiber yield, fiber quality, and/or nitrogen use efficiency of a plant.

Thus, as shown in the Examples section which follows, the present inventors have utilized bioinformatics tools to identify polynucleotides which increase abiotic stress tolerance (ABST), fertilizer use efficiency [e.g., nitrogen use efficiency (NUE)], yield (e.g., seed yield, oil yield, oil content), growth rate, biomass, vigor and/or of a plant. Genes which affect the trait-of-interest were identified using digital expression profiles in specific tissues and conditions such as expression in roots; expression under stress conditions such as drought stress, ultraviolet (UV) irradiation, cold stress, heat stress, nutrient deficiency, stress hormones [for example as abscisic acid (ABA) and ethylene] etiolation conditions, salinity stress, waterlogging; and/or expression during plant development (Tables 1-5; Example 1 of the Examples section which follows; polynucleotide SEQ ID NOs:1-59 and 638; polypeptide SEQ ID NOs:60-112). Homologous polypeptides and polynucleotides having the same function were also identified (Table 6, Example 2 of the Examples section which follows; polynucleotide SEQ ID NOs:113-358; polypeptide SEQ ID NOs:359-604). The identified polynucleotides were cloned into binary vectors [Tables 7-10; Example 3; SEQ ID NOs:605-637, 639-651, 670, 671 (polynucleotides); SEQ ID NOs: 60, 63-73, 75, 77, 81-83, 86, 87, 90, 92, 93, 94, 95, 96, 99, 100, 101, 102, 652-669, 672 (polypeptides)], transformed into *agrobacterium* cells (Example 4), and further into *Arabidopsis* plants (Example 5). Transgenic plants over-expressing the identified polynucleotides were found to exhibit increased biomass [e.g., fresh and dry weight; leaf area and growth rate, rosette area, rosette diameter and growth rate of rosette area and diameter, plot coverage, leaf number], growth rate, yield (e.g., seed yield and weight), harvest index, roots growth (e.g., root length, root coverage, growth rate of root length and/or coverage), oil yield, oil percentage in seeds, weight of 1000 seeds (Tables 11-62; Examples 6, 7, 8, 9, and 11 of the Examples section which follows) under normal or limiting conditions (e.g., abiotic stress, nitrogen limiting conditions). Altogether, these results suggest the use of the novel polynucleotides and polypeptides of the invention for increasing abiotic stress tolerance, yield, biomass, growth rate, vigor, oil content, fiber yield, fiber quality, and/or nitrogen use efficiency of a plant.

Thus, according to an aspect of some embodiments of the invention, there is provided method of increasing abiotic stress tolerance, yield, biomass, growth rate, vigor, oil content, fiber yield, fiber quality, and/or nitrogen use efficiency of a plant, the method comprising expressing within the plant an exogenous polynucleotide comprising a nucleic acid sequence at least 80% identical to SEQ ID NO: 619, 617, 606, 615, 629, 1-36, 40, 41, 43-45, 49, 52-56, 58, 113-343, 351, 354-358, 605, 607-614, 616, 618, 620-628, 630-638, 642, 645, 650, 651, 670 or 671, thereby increasing the abiotic stress tolerance, yield, biomass, growth rate, vigor, oil content, fiber yield, fiber quality, and/or nitrogen use efficiency of the plant.

As used herein the phrase "plant yield" refers to the amount (e.g., as determined by weight or size) or quantity (numbers) of tissues or organs produced per plant or per growing season. Hence increased yield could affect the economic benefit one can obtain from the plant in a certain growing area and/or growing time.

It should be noted that a plant yield can be affected by various parameters including, but not limited to, plant biomass; plant vigor; growth rate; seed yield; seed or grain quantity; seed or grain quality; oil yield; content of oil, starch and/or protein in harvested organs (e.g., seeds or vegetative parts of the plant); number of flowers (florets) per panicle (expressed as a ratio of number of filled seeds over number of primary panicles); harvest index; number of plants grown per area; number and size of harvested organs per plant and per area; number of plants per growing area (density); number of harvested organs in field; total leaf area; carbon assimilation and carbon partitioning (the distribution/allocation of carbon within the plant); resistance to shade; number of harvestable organs (e.g. seeds), seeds per pod, weight per seed; and modified architecture [such as increase stalk diameter, thickness or improvement of physical properties (e.g. elasticity)].

As used herein the phrase "seed yield" refers to the number or weight of the seeds per plant, seeds per pod, or per growing area or to the weight of a single seed, or to the oil extracted per seed. Hence seed yield can be affected by seed dimensions (e.g., length, width, perimeter, area and/or volume), number of (filled) seeds and seed filling rate and by seed oil content. Hence increase seed yield per plant could affect the economic benefit one can obtain from the plant in a certain growing area and/or growing time; and increase seed yield per growing area could be achieved by increasing seed yield per plant, and/or by increasing number of plants grown on the same given area.

The term "seed" (also referred to as "grain" or "kernel") as used herein refers to a small embryonic plant enclosed in a covering called the seed coat (usually with some stored food), the product of the ripened ovule of gymnosperm and angiosperm plants which occurs after fertilization and some growth within the mother plant.

The phrase "oil content" as used herein refers to the amount of lipids in a given plant organ, either the seeds (seed oil content) or the vegetative portion of the plant (vegetative oil content) and is typically expressed as percentage of dry weight (10% humidity of seeds) or wet weight (for vegetative portion).

It should be noted that oil content is affected by intrinsic oil production of a tissue (e.g., seed, vegetative portion), as well as the mass or size of the oil-producing tissue per plant or per growth period.

In one embodiment, increase in oil content of the plant can be achieved by increasing the size/mass of a plant's tissue(s) which comprise oil per growth period. Thus, increased oil content of a plant can be achieved by increasing the yield, growth rate, biomass and vigor of the plant.

As used herein the phrase "plant biomass" refers to the amount (e.g., measured in grams of air-dry tissue) of a tissue produced from the plant in a growing season, which could also determine or affect the plant yield or the yield per growing area. An increase in plant biomass can be in the whole plant or in parts thereof such as aboveground (harvestable) parts, vegetative biomass, roots and seeds.

As used herein the phrase "growth rate" refers to the increase in plant organ/tissue size per time (can be measured in $cm^2$ per day).

As used herein the phrase "plant vigor" refers to the amount (measured by weight) of tissue produced by the plant in a given time. Hence increased vigor could determine or affect the plant yield or the yield per growing time or growing area. In addition, early vigor (seed and/or seedling) results in improved field stand.

It should be noted that a plant yield can be determined under stress (e.g., abiotic stress, nitrogen-limiting conditions) and/or non-stress (normal) conditions.

As used herein, the phrase "non-stress conditions" refers to the growth conditions (e.g., water, temperature, light-dark cycles, humidity, salt concentration, fertilizer concentration in soil, nutrient supply such as nitrogen, phosphorous and/or potassium), that do not significantly go beyond the everyday climatic and other abiotic conditions that plants may encounter, and which allow optimal growth, metabolism, reproduction and/or viability of a plant at any stage in its life cycle (e.g., in a crop plant from seed to a mature plant and back to seed again). Persons skilled in the art are aware of normal soil conditions and climatic conditions for a given plant in a given geographic location. It should be noted that while the non-stress conditions may include some mild variations from the optimal conditions (which vary from one type/species of a plant to another), such variations do not cause the plant to cease growing without the capacity to resume growth.

The phrase "abiotic stress" as used herein refers to any adverse effect on metabolism, growth, reproduction and/or viability of a plant. Accordingly, abiotic stress can be induced by suboptimal environmental growth conditions such as, for example, salinity, water deprivation, flooding, freezing, low or high temperature, heavy metal toxicity, anaerobiosis, nutrient deficiency, atmospheric pollution or UV irradiation. The implications of abiotic stress are discussed in the Background section.

The phrase "abiotic stress tolerance" as used herein refers to the ability of a plant to endure an abiotic stress without suffering a substantial alteration in metabolism, growth, productivity and/or viability.

As used herein the phrase "water use efficiency (WUE)" refers to the level of organic matter produced per unit of water consumed by the plant, i.e., the dry weight of a plant in relation to the plant's water use, e.g., the biomass produced per unit transpiration.

As used herein the phrase "fertilizer use efficiency" refers to the metabolic process(es) which lead to an increase in the plant's yield, biomass, vigor, and growth rate per fertilizer unit applied. The metabolic process can be the uptake, spread, absorbent, accumulation, relocation (within the plant) and use of one or more of the minerals and organic moieties absorbed by the plant, such as nitrogen, phosphates and/or potassium.

As used herein the phrase "fertilizer-limiting conditions" refers to growth conditions which include a level (e.g., concentration) of a fertilizer applied which is below the level needed for normal plant metabolism, growth, reproduction and/or viability.

As used herein the phrase "nitrogen use efficiency (NUE)" refers to the metabolic process(es) which lead to an increase in the plant's yield, biomass, vigor, and growth rate per nitrogen unit applied. The metabolic process can be the uptake, spread, absorbent, accumulation, relocation (within the plant) and use of nitrogen absorbed by the plant.

As used herein the phrase "nitrogen-limiting conditions" refers to growth conditions which include a level (e.g., concentration) of nitrogen (e.g., ammonium or nitrate) applied which is below the level needed for normal plant metabolism, growth, reproduction and/or viability.

Improved plant NUE and FUE is translated in the field into either harvesting similar quantities of yield, while implementing less fertilizers, or increased yields gained by implementing the same levels of fertilizers. Thus, improved NUE or FUE has a direct effect on plant yield in the field. Thus, the polynucleotides and polypeptides of some embodiments of the invention positively affect plant yield, seed yield, and plant biomass. In addition, the benefit of improved plant NUE will certainly improve crop quality and biochemical constituents of the seed such as protein yield and oil yield.

It should be noted that improved ABST will confer plants with improved vigor also under non-stress conditions, resulting in crops having improved biomass and/or yield e.g., elongated fibers for the cotton industry, higher oil content.

As used herein the term "increasing" refers to at least about 2%, at least about 3%, at least about 4%, at least about 5%, at least about 10%, at least about 15%, at least about 20%, at least about 30%, at least about 40%, at least about 50%, at least about 60%, at least about 70%, at least about 80%, increase in abiotic stress tolerance, yield, biomass, growth rate, vigor, oil content, fiber yield, fiber quality, and/or nitrogen use efficiency of a plant as compared to a native plant [i.e., a plant not modified with the biomolecules (polynucleotide or polypeptides) of the invention, e.g., a non-transformed plant of the same species which is grown under the same growth conditions).

The phrase "expressing within the plant an exogenous polynucleotide" as used herein refers to upregulating the expression level of an exogenous polynucleotide within the plant by introducing the exogenous polynucleotide into a plant cell or plant and expressing by recombinant means, as further described herein below.

As used herein "expressing" refers to expression at the mRNA and optionally polypeptide level.

As used herein, the phrase "exogenous polynucleotide" refers to a heterologous nucleic acid sequence which may not be naturally expressed within the plant or which overexpression in the plant is desired. The exogenous polynucleotide may be introduced into the plant in a stable or transient manner, so as to produce a ribonucleic acid (RNA) molecule and/or a polypeptide molecule. It should be noted that the exogenous polynucleotide may comprise a nucleic acid sequence which is identical or partially homologous to an endogenous nucleic acid sequence of the plant.

The term "endogenous" as used herein refers to any polynucleotide or polypeptide which is present and/or naturally expressed within a plant or a cell thereof.

According to some embodiments of the invention the exogenous polynucleotide comprises a nucleic acid sequence which is at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to the nucleic acid sequence selected from the group consisting of SEQ ID NOs: 619, 617, 606, 615, 629, 1-36, 40, 41, 43-45, 49, 52-56, 58, 113-343, 351, 354-358, 605, 607-614, 616, 618, 620-628, 630-638, 642, 645, 650, 651, 670, and 671.

Identity (e.g., percent homology) can be determined using any homology comparison software, including for example, the BlastN software of the National Center of Biotechnology Information (NCBI) such as by using default parameters.

According to some embodiments of the invention the exogenous polynucleotide is at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to the polynucleotide selected from the group consisting of SEQ ID NOs: 619, 617, 606, 615, 629, 1-36, 40, 41, 43-45, 49, 52-56, 58, 113-343, 351, 354-358, 605, 607-614, 616, 618, 620-628, 630-638, 642, 645, 650, 651, 670, and 671.

According to some embodiments of the invention the exogenous polynucleotide is set forth by SEQ ID NO:619, 617, 606, 615, 629, 1-36, 40, 41, 43-45, 49, 52-56, 58, 113-343, 351, 354-358, 605, 607-614, 616, 618, 620-628, 630-638, 642, 645, 650, 651, 670, or 671.

According to an aspect of some embodiments of the invention, there is provided a method of increasing abiotic stress tolerance, yield, biomass, growth rate, vigor, oil content, fiber yield, fiber quality, and/or nitrogen use efficiency of a plant, comprising expressing within the plant an exogenous polynucleotide comprising the nucleic acid sequence selected from the group consisting of SEQ ID NOs:619, 617, 606, 615, 629, 1-49, 51-59, 113-343, 345-351, 353-358, 605, 607-614, 616, 618, 620-628, 630-638, 641, 642, 644, 644-646, 648-651, 670, and 671, thereby increasing the abiotic stress tolerance, yield, biomass, growth rate, vigor, oil content, fiber yield, fiber quality, and/or nitrogen use efficiency of the plant.

According to some embodiments of the invention the exogenous polynucleotide is set forth by the nucleic acid sequence selected from the group consisting of SEQ ID NOs:619, 617, 606, 615, 629, 1-49, 51-59, 113-343, 345-351, 353-358, 605, 607-614, 616, 618, 620-628, 630-638, 641, 642, 644, 644-646, 648-651, 670, and 671.

According to an aspect of some embodiments of the invention, there is provided a method of increasing abiotic stress tolerance, nitrogen use efficiency, fiber yield and/or fiber quality of a plant, comprising expressing within the plant an exogenous polynucleotide comprising a nucleic acid sequence at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to the polynucleotide selected from the group consisting of SEQ ID NOs:352, 639, 640, and 643, thereby increasing the abiotic stress tolerance, nitrogen use efficiency, fiber yield and/or fiber quality of the plant.

According to an aspect of some embodiments of the invention, there is provided a method of increasing abiotic stress tolerance, nitrogen use efficiency, fiber yield and/or fiber quality of a plant, comprising expressing within the plant an exogenous polynucleotide comprising the nucleic acid sequence selected from the group consisting of SEQ ID NOs: 352, 639, 640, and 643, thereby increasing the abiotic stress tolerance, nitrogen use efficiency, fiber yield and/or fiber quality of the plant.

According to some embodiments of the invention the exogenous polynucleotide is set forth by the nucleic acid sequence selected from the group consisting of SEQ ID NOs: 352, 639, 640, and 643.

According to an aspect of some embodiments of the invention, there is provided a method of increasing nitrogen use efficiency, seed yield and/or oil content of a plant, comprising expressing within the plant an exogenous polynucleotide comprising a nucleic acid sequence at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to the polynucleotide selected from the group consisting of SEQ ID NOs:50, 645, and 647, thereby increasing the nitrogen use efficiency, seed yield and/or oil content of the plant.

According to an aspect of some embodiments of the invention, there is provided a method of increasing nitrogen use efficiency, seed yield and/or oil content of a plant, comprising expressing within the plant an exogenous polynucleotide comprising the nucleic acid sequence selected from the group consisting of SEQ ID NOs:50, 645 and 647, thereby increasing the nitrogen use efficiency, seed yield and/or oil content of the plant.

According to some embodiments of the invention the exogenous polynucleotide is set forth by the nucleic acid sequence selected from the group consisting of SEQ ID NOs: 50, 645 and 647.

According to an aspect of some embodiments of the invention, there is provided a method of increasing seed yield, fiber yield and/or fiber quality of a plant, comprising expressing within the plant an exogenous polynucleotide comprising a nucleic acid sequence at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to the polynucleotide set forth by SEQ ID NO:344, thereby increasing the seed yield, fiber yield and/or fiber quality of the plant.

According to an aspect of some embodiments of the invention, there is provided a method of increasing seed yield, fiber yield and/or fiber quality of a plant, comprising expressing within the plant an exogenous polynucleotide comprising the nucleic acid sequence set forth in SEQ ID NO:344, thereby increasing the seed yield, fiber yield and/or fiber quality of the plant.

According to some embodiments of the invention the exogenous polynucleotide is set forth by the nucleic acid sequence set forth in SEQ ID NO:344.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

The term "isolated" refers to at least partially separated from the natural environment e.g., from a plant cell.

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

According to some embodiments of the invention, the exogenous polynucleotide comprising a nucleic acid sequence encoding a polypeptide having an amino acid sequence at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more say 100% homologous to the amino acid sequence selected from the group consisting of SEQ ID NOs:75, 73, 652, 71, 86, 60-70, 72, 74, 76-85, 87-95, 108-109, 112, 359-589, 602-604, 653-660, 665, 668, and 672.

Homology (e.g., percent homology) can be determined using any homology comparison software, including for example, the BlastP or TBLASTN software of the National Center of Biotechnology Information (NCBI) such as by using default parameters, when starting from a polypeptide sequence; or the tBLASTX algorithm (available via the NCBI) such as by using default parameters, which compares the six-frame conceptual translation products of a nucleotide query sequence (both strands) against a protein sequence database.

Homologous sequences include both orthologous and paralogous sequences. The term "paralogous" relates to gene-duplications within the genome of a species leading to paralogous genes. The term "orthologous" relates to homologous genes in different organisms due to ancestral relationship.

One option to identify orthologues in monocot plant species is by performing a reciprocal blast search. This may be done by a first blast involving blasting the sequence-of-interest against any sequence database, such as the publicly available NCBI database which may be found at: Hypertext Transfer Protocol://World Wide Web (dot) ncbi (dot) nlm (dot) nih (dot) gov. If orthologues in rice were sought, the sequence-of-interest would be blasted against, for example, the 28,469 full-length cDNA clones from *Oryza sativa* Nipponbare available at NCBI. The blast results may be filtered. The full-length sequences of either the filtered results or the non-filtered results are then blasted back (second blast) against the sequences of the organism from which the sequence-of-interest is derived. The results of the first and second blasts are then compared. An orthologue is identified when the sequence resulting in the highest score (best hit) in the first blast identifies in the second blast the query sequence (the original sequence-of-interest) as the best hit. Using the same rational a paralogue (homolog to a gene in the same organism) is found. In case of large sequence families, the ClustalW program may be used [Hypertext Transfer Protocol://World Wide Web (dot) ebi (dot) ac (dot) uk/Tools/clustalw2/index (dot) html], followed by a neighbor-joining tree (Hypertext Transfer Protocol://en (dot) wikipedia (dot) org/wiki/Neighbor-joining) which helps visualizing the clustering.

According to some embodiments of the invention, the exogenous polynucleotide encodes a polypeptide consisting of the amino acid sequence set forth by SEQ ID NO: 75, 73, 652, 71, 86, 60-70, 72, 74, 76-85, 87-95, 108-109, 112, 359-589, 602-604, 653-660, 665, 668, or 672.

According to an aspect of some embodiments of the invention, the method of increasing abiotic stress tolerance, yield, biomass, growth rate, vigor, oil content, fiber yield, fiber quality, and/or nitrogen use efficiency of a plant, is effected by expressing within the plant an exogenous polynucleotide comprising a nucleic acid sequence encoding a polypeptide comprising an amino acid sequence selected from the group consisting of SEQ ID NOs:75, 73, 652, 71, 86, 60-70, 72, 74, 76-85, 87-98, 100-109, 111, 112, 359-589, 591-597, 600-604, 653-662, 664, 666-669, and 672, thereby increasing the abiotic stress tolerance, yield, biomass, growth rate, vigor, oil content, fiber yield, fiber quality, and/or nitrogen use efficiency of the plant.

According to some embodiments of the invention, the exogenous polynucleotide encodes a polypeptide consisting of the amino acid sequence set forth by SEQ ID NO: 75, 73, 652, 71, 86, 60-70, 72, 74, 76-85, 87-98, 100-109, 111, 112, 359-589, 591-597, 600-604, 653-662, 664, 666-669, or 672.

According to an aspect of some embodiments of the invention, the method of increasing abiotic stress tolerance, nitrogen use efficiency, fiber yield and/or fiber quality of a plant, is effected by expressing within the plant an exogenous polynucleotide comprising a nucleic acid sequence encoding a polypeptide having an amino acid sequence least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more say 100% homologous to the amino acid sequence selected from the group consisting of SEQ ID NOs:99 and 598, thereby increasing the abiotic stress tolerance, nitrogen use efficiency, fiber yield and/or fiber quality of the plant.

According to an aspect of some embodiments of the invention, the method of increasing abiotic stress tolerance, nitrogen use efficiency, fiber yield and/or fiber quality of a plant is effected by expressing within the plant an exogenous polynucleotide comprising a nucleic acid sequence encoding a polypeptide comprising the amino acid sequence selected from the group consisting of SEQ ID NOs: 99 and 598, thereby increasing the abiotic stress tolerance, nitrogen use efficiency, fiber yield and/or fiber quality of the plant.

According to some embodiments of the invention, the exogenous polynucleotide encodes a polypeptide consisting of the amino acid sequence set forth by SEQ ID NO: 99 or 598.

According to an aspect of some embodiments of the invention, the method of increasing nitrogen use efficiency, seed yield and/or oil content of a plant is effected expressing within the plant an exogenous polynucleotide comprising a nucleic acid sequence encoding a polypeptide having an amino acid sequence least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more say 100% homologous to the amino acid sequence selected from the group consisting of SEQ ID NOs:599 and 663, thereby increasing the nitrogen use efficiency, seed yield and/or oil content of the plant.

According to an aspect of some embodiments of the invention, the method of increasing nitrogen use efficiency, seed yield and/or oil content of a plant is effected by expressing within the plant an exogenous polynucleotide comprising a nucleic acid sequence encoding a polypeptide comprising the amino acid sequence selected from the group consisting of SEQ ID NOs: 599 and 663, thereby increasing the nitrogen use efficiency, seed yield and/or oil content of the plant.

According to some embodiments of the invention, the exogenous polynucleotide encodes a polypeptide consisting of the amino acid sequence set forth by SEQ ID NO: 599 or 663.

According to an aspect of some embodiments of the invention, the method of increasing nitrogen use efficiency, abiotic stress tolerance, seed yield and/or oil content of a plant is effected by expressing within the plant an exogenous polynucleotide comprising a nucleic acid sequence encoding a polypeptide having an amino acid sequence least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more say 100% homologous to the amino acid sequence selected from the group consisting of SEQ ID NOs:110 and 665, thereby increasing the nitrogen use efficiency, abiotic stress tolerance, seed yield and/or oil content of the plant.

According to an aspect of some embodiments of the invention, the method of increasing nitrogen use efficiency, abiotic stress tolerance, seed yield and/or oil content of a plant is effected by expressing within the plant an exogenous polynucleotide comprising a nucleic acid sequence encoding a polypeptide comprising the amino acid sequence selected from the group consisting of SEQ ID NOs:110 and 665, thereby increasing the nitrogen use efficiency, abiotic stress tolerance, seed yield and/or oil content of the plant.

According to some embodiments of the invention, the exogenous polynucleotide encodes a polypeptide consisting of the amino acid sequence set forth by SEQ ID NO: 110 or 665.

According to an aspect of some embodiments of the invention, the method of increasing seed yield, fiber yield and/or fiber quality of a plant is effected by expressing within the plant an exogenous polynucleotide comprising a nucleic acid sequence encoding a polypeptide having an amino acid sequence least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more say 100% homologous to the amino acid sequence set forth by SEQ ID NO:590, thereby increasing the seed yield, fiber yield and/or fiber quality of the plant.

According to an aspect of some embodiments of the invention, the method of increasing seed yield, fiber yield and/or fiber quality of a plant is effected by expressing within the plant an exogenous polynucleotide comprising a nucleic acid sequence encoding a polypeptide comprising the amino acid sequence set forth by SEQ ID NO:590, thereby increasing the seed yield, fiber yield and/or fiber quality of the plant.

According to some embodiments of the invention, the exogenous polynucleotide encodes a polypeptide consisting of the amino acid sequence set forth by SEQ ID NO:590.

Nucleic acid sequences encoding the polypeptides of the present invention may be optimized for expression. Non-limiting examples of optimized nucleic acid sequences are provided in SEQ ID NOs: 670 (BDL103_long), 639 (BDL11) and 643 (BDL17) which encode optimized polypeptide comprising the amino acid sequences set forth by SEQ ID NOs: 96, 661 and 101, respectively. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1N[(Xn−Yn)/Yn]2/N, where Xn refers to the frequency of usage of codon n in highly expressed plant genes, where Yn to the frequency of usage of codon n in the gene of interest and N refers to the total number of codons in the gene of interest. A Table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization Tables such as those provided on-line at the Codon Usage Database through the NIAS (National Institute of Agrobiological Sciences) DNA bank in Japan (Hypertext Transfer Protocol://World Wide Web (dot) kazusa (dot) or (dot) jp/codon/). The Codon Usage Database contains codon usage tables for a number of different species, with each codon usage Table having been statistically determined based on the data present in Genbank.

By using the above Tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

Thus, the invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

The invention provides an isolated polynucleotide comprising a nucleic acid sequence at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to the polynucleotide selected from the group consisting of SEQ ID NOs: 619, 617, 606, 615, 629, 1-36, 40, 41, 43-45, 49, 52-56, 58, 113-343, 351, 354-358, 605, 607-614, 616, 618, 620-628, 630-638, 642, 645, 650-651, 670, and 671.

According to some embodiments of the invention the nucleic acid sequence is capable of increasing abiotic stress tolerance, yield, biomass, growth rate, vigor, oil content, fiber yield, fiber quality, and/or nitrogen use efficiency of a plant.

According to some embodiments of the invention the isolated polynucleotide comprising the nucleic acid sequence selected from the group consisting of SEQ ID NOs: 619, 617, 606, 615, 629, 1-36, 40, 41, 43-45, 49, 52-56, 58, 113-343, 351, 354-358, 605, 607-614, 616, 618, 620-628, 630-638, 642, 645, 650-651, 670, and 671.

According to some embodiments of the invention the isolated polynucleotide consists of the nucleic acid sequence selected from the group consisting of SEQ ID NOs:619, 617, 606, 615, 629, 1-36, 40, 41, 43-45, 49, 52-56, 58, 113-343, 351, 354-358, 605, 607-614, 616, 618, 620-628, 630-638, 642, 645, 650, 651, 670, and 671.

According to some embodiments of the invention the isolated polynucleotide is set forth by SEQ ID NO: 619, 617, 606, 615, 629, 1-36, 40, 41, 43-45, 49, 52-56, 58, 113-343, 351, 354-358, 605, 607-614, 616, 618, 620-628, 630-638, 642, 645, 650-651, 670, and 671.

According to an aspect of some embodiments of the invention, there is provided an isolated polynucleotide comprising the nucleic acid sequence selected from the group consisting of SEQ ID NOs:619, 617, 606, 615, 629, 1-49, 51-59, 113-343, 345-351, 353-358, 605, 607-614, 616, 618, 620-628, 630-638, 641, 642, 644, 644-646, 648-651, 670, and 671.

The invention provides an isolated polynucleotide comprising a nucleic acid sequence encoding a polypeptide which comprises an amino acid sequence at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to the amino acid sequence selected from the group consisting of SEQ ID NOs:75, 73, 652, 71, 86, 60-70, 72, 74, 76-85, 87-95, 108-109, 112, 359-589, 602-604, 653-660, 665, 668, and 672.

According to some embodiments of the invention the amino acid sequence is capable of increasing abiotic stress tolerance, yield, biomass, growth rate, vigor, oil content, fiber yield, fiber quality, and/or nitrogen use efficiency of a plant.

The invention provides an isolated polynucleotide comprising a nucleic acid sequence encoding a polypeptide which comprises the amino acid sequence selected from the group consisting of SEQ ID NOs: 75, 73, 652, 71, 86, 60-70, 72, 74, 76-85, 87-98, 100-109, 111, 112, 359-589, 591-597, 600-604, 653-662, 664, 666-669, and 672.

The invention provides an isolated polypeptide comprising an amino acid sequence at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to an amino acid sequence selected from the group consisting of SEQ ID NOs:75, 73, 652, 71, 86, 60-70, 72, 74, 76-85, 87-95, 108-109, 112, 359-589, 602-604, 653-660, 665, 668, and 672.

According to some embodiments of the invention the isolated polypeptide is capable of increasing abiotic stress tolerance, yield, biomass, growth rate, vigor, oil content, fiber yield, fiber quality, and/or nitrogen use efficiency of a plant.

According to some embodiments of the invention, the polypeptide comprising an amino acid sequence selected from the group consisting of SEQ ID NOs: 75, 73, 652, 71, 86, 60-70, 72, 74, 76-85, 87-98, 100-109, 111, 112, 359-589, 591-597, 600-604, 653-662, 664, 666-669, and 672.

According to some embodiments of the invention, the polypeptide is set forth by SEQ ID NO: 75, 73, 652, 71, 86, 60-70, 72, 74, 76-85, 87-98, 100-109, 111, 112, 359-589, 591-597, 600-604, 653-662, 664, 666-669, or 672.

The invention also encompasses fragments of the above described polypeptides and polypeptides having mutations, such as deletions, insertions or substitutions of one or more amino acids, either naturally occurring or man induced, either randomly or in a targeted fashion.

The term "plant" as used herein encompasses whole plants, ancestors and progeny of the plants and plant parts, including seeds, shoots, stems, roots (including tubers), and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium rectum*, *Echinochloa pyramidalis*, *Ehraffia* spp., *Eleusine coracana*, *Eragrestis* spp., *Erythrina* spp., *Eucalypfus* spp., *Euclea schimperi*, *Eulalia* vi/losa, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffus*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesli*, *Lotus* spp., *Macrotyloma axillare*, *Malus* spp., *Manihot esculenta*, *Medicago saliva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativam*, *Podocarpus totara*, *Pogonarthria fleckii*, *Pogonaffhria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys vefficillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barely, rye, oat, peanut, pea, lentil and alfalfa, cotton, rapeseed, canola, pepper, sunflower, tobacco, eggplant, eucalyptus, a tree, an ornamental plant, a perennial grass and a forage crop. Alternatively algae and other non-Viridiplantae can be used for the methods of the present invention.

According to some embodiments of the invention, the plant used by the method of the invention is a crop plant such as rice, maize, wheat, barley, peanut, potato, sesame, olive tree, palm oil, banana, soybean, sunflower, canola, sugarcane, alfalfa, millet, leguminosae (bean, pea), flax, lupinus, rapeseed, tobacco, poplar and cotton.

According to some embodiments of the invention, there is provided a plant cell exogenously expressing the polynucleotide of some embodiments of the invention, the nucleic acid construct of some embodiments of the invention and/or the polypeptide of some embodiments of the invention.

According to some embodiments of the invention, expressing the exogenous polynucleotide of the invention within the plant is effected by transforming one or more cells of the plant with the exogenous polynucleotide, followed by generating a mature plant from the transformed cells and cultivating the mature plant under conditions suitable for expressing the exogenous polynucleotide within the mature plant.

According to some embodiments of the invention, the transformation is effected by introducing to the plant cell a nucleic acid construct which includes the exogenous polynucleotide of some embodiments of the invention and at least one promoter for directing transcription of the exogenous polynucleotide in a host cell (a plant cell). Further details of suitable transformation approaches are provided hereinbelow.

According to some embodiments of the invention, there is provided a nucleic acid construct comprising the isolated polynucleotide of the invention, and a promoter for directing transcription of the nucleic acid sequence of the isolated polynucleotide in a host cell.

According to some embodiments of the invention, the isolated polynucleotide is operably linked to the promoter sequence.

A coding nucleic acid sequence is "operably linked" to a regulatory sequence (e.g., promoter) if the regulatory sequence is capable of exerting a regulatory effect on the coding sequence linked thereto.

As used herein, the term "promoter" refers to a region of DNA which lies upstream of the transcriptional initiation site of a gene to which RNA polymerase binds to initiate transcription of RNA. The promoter controls where (e.g., which portion of a plant) and/or when (e.g., at which stage or condition in the lifetime of an organism) the gene is expressed.

Any suitable promoter sequence can be used by the nucleic acid construct of the present invention. Preferably the promoter is a constitutive promoter, a tissue-specific, or an abiotic stress-inducible promoter.

Suitable constitutive promoters include, for example, CaMV 35S promoter (SEQ ID NO:675; Odell et al., Nature 313:810-812, 1985); Arabidopsis At6669 promoter (SEQ ID NO:674; see PCT Publication No. WO04081173A2); maize Ubi 1 (Christensen et al., Plant Sol. Biol. 18:675-689, 1992); rice actin (McElroy et al., Plant Cell 2:163-171, 1990); pEMU (Last et al., Theor. Appl. Genet. 81:581-588, 1991); CaMV 19S (Nilsson et al., Physiol. Plant 100:456-462, 1997); GOS2 (de Pater et al, Plant J November; 2 (6):837-44, 1992); ubiquitin (Christensen et al, Plant Mol. Biol. 18: 675-689, 1992); Rice cyclophilin (Bucholz et al, Plant Mol. Biol. 25 (5):837-43, 1994); Maize H3 histone (Lepetit et al, Mol. Gen. Genet. 231: 276-285, 1992); Actin 2 (An et al, Plant J. 10 (1); 107-121, 1996) and Synthetic Super MAS (Ni et al., The Plant Journal 7: 661-76, 1995). Other constitutive promoters include those in U.S. Pat. Nos. 5,659,026, 5,608,149; 5,608, 144; 5,604,121; 5,569,597; 5,466,785; 5,399,680; 5,268,463; and 5,608,142.

Suitable tissue-specific promoters include, but not limited to, leaf-specific promoters [such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993], seed-preferred promoters [e.g., from seed specific genes (Simon, et al., Plant Mol. Biol. 5. 191, 1985; Scofield, et al., J. Biol. Chem. 262: 12202, 1987; Baszczynski, et al., Plant Mol. Biol. 14: 633, 1990), Brazil Nut albumin (Pearson' et al., Plant Mol. Biol. 18: 235-245, 1992), legumin (Ellis, et al. Plant Mol. Biol. 10: 203-214, 1988), Glutelin (rice) (Takaiwa, et al., Mol. Gen. Genet. 208: 15-22, 1986; Takaiwa, et al., FEBS Letts. 221: 43-47, 1987), Zein (Matzke et al Plant Mol Biol, 143). 323-32 1990), napA (Stalberg, et al, Planta 199: 515-519, 1996), Wheat SPA (Albanietal, Plant Cell, 9: 171-184, 1997), sunflower oleosin (Cummins, et al., Plant Mol. Biol. 19: 873-876, 1992)], endosperm specific promoters [e.g., wheat LMW and HMW, glutenin-1 (Mol Gen Genet. 216:81-90, 1989; NAR 17:461-2), wheat a, b and g gliadins (EMBO3:1409-15, 1984), Barley 1tr1 promoter, barley B1, C, D hordein (Theor Appl Gen 98:1253-62, 1999; Plant J 4:343-55, 1993; Mol Gen Genet. 250:750-60, 1996), Barley DOF (Mena et al, The Plant Journal, 116 (1): 53-62, 1998), Biz2 (EP99106056.7), Synthetic promoter (Vicente-Carbajosa et al., Plant J. 13: 629-640, 1998), rice prolamin NRP33, rice-globulin Glb-1 (Wu et al, Plant Cell Physiology 39 (8) 885-889, 1998), rice alpha-globulin REB/OHP-1 (Nakase et al. Plant Mol. Biol. 33: 513-S22, 1997), rice ADP-glucose PP (Trans Res 6:157-68, 1997), maize ESR gene family (Plant J 12:235-46, 1997), sorgum gamma-kafirin (PMB 32:1029-35, 1996)], embryo specific promoters [e.g., rice OSH1 (Sato et al, Proc. Natl. Acad. Sci. USA, 93: 8117-8122), KNOX (Postma-Haarsma of al, Plant Mol. Biol. 39:257-71, 1999), rice oleosin (Wu et at, J. Biochem., 123: 386, 1998)], and flower-specific promoters [e.g., AtPRP4, chalene synthase (chsA) (Van der Meer, et al., Plant Mol. Biol. 15, 95-109, 1990), LAT52 (Twell et al Mol. Gen. Genet. 217:240-245; 1989), apetala-3].

Suitable abiotic stress-inducible promoters include, but not limited to, salt-inducible promoters such as RD29A (Yamaguchi-Shinozalei et al., Mol. Gen. Genet. 236:331-340, 1993); drought-inducible promoters such as maize rab17 gene promoter (Pla et. al., Plant Mol. Biol. 21:259-266, 1993), maize rab28 gene promoter (Busk et. al., Plant J. 11:1285-1295, 1997) and maize Ivr2 gene promoter (Pelleschi et. al., Plant Mol. Biol. 39:373-380, 1999); heat-inducible promoters such as heat tomato hsp80-promoter from tomato (U.S. Pat. No. 5,187,267).

The nucleic acid construct of some embodiments of the invention can further include an appropriate selectable marker and/or an origin of replication. According to some embodiments of the invention, the nucleic acid construct utilized is a shuttle vector, which can propagate both in E. coli (wherein the construct comprises an appropriate selectable marker and origin of replication) and be compatible with propagation in cells. The construct according to the present invention can be, for example, a plasmid, a bacmid, a phagemid, a cosmid, a phage, a virus or an artificial chromosome.

The nucleic acid construct of some embodiments of the invention can be utilized to stably or transiently transform plant cells. In stable transformation, the exogenous polynucleotide is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338:274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S, and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. See, e.g., Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

According to some embodiments of the invention, the transgenic plants are generated by transient transformation of leaf cells, meristematic cells or the whole plant.

Transient transformation can be effected by any of the direct DNA transfer methods described above or by viral infection using modified plant viruses.

Viruses that have been shown to be useful for the transformation of plant hosts include CaMV, Tobacco mosaic virus (TMV), brome mosaic virus (BMV) and Bean Common Mosaic Virus (BV or BCMV). Transformation of plants using plant viruses is described in U.S. Pat. No. 4,855,237 (bean golden mosaic virus; BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants are described in WO 87/06261.

According to some embodiments of the invention, the virus used for transient transformations is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; Takamatsu et al. FEBS Letters (1990) 269:73-76; and U.S. Pat. No. 5,316,931.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters. Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, New York.

In addition to the above, the polynucleotide of the present invention can also be introduced into a chloroplast genome thereby enabling chloroplast expression.

A technique for introducing exogenous polynucleotide sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the exogenous polynucleotide includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Since processes which increase oil content, yield, growth rate, biomass, vigor and/or abiotic stress tolerance of a plant can involve multiple genes acting additively or in synergy (see, for example, in Quesda et al., Plant Physiol. 130:951-063, 2002), the present invention also envisages expressing a plurality of exogenous polynucleotides in a single host plant to thereby achieve superior effect on oil content, yield, growth rate, biomass, vigor and/or abiotic stress tolerance.

Expressing a plurality of exogenous polynucleotides in a single host plant can be effected by co-introducing multiple nucleic acid constructs, each including a different exogenous polynucleotide, into a single plant cell. The transformed cell can than be regenerated into a mature plant using the methods described hereinabove.

Alternatively, expressing a plurality of exogenous polynucleotides in a single host plant can be effected by co-introducing into a single plant-cell a single nucleic-acid construct including a plurality of different exogenous polynucleotides. Such a construct can be designed with a single promoter sequence which can transcribe a polycistronic messenger RNA including all the different exogenous polynucleotide sequences. To enable co-translation of the different polypeptides encoded by the polycistronic messenger RNA, the polynucleotide sequences can be inter-linked via an internal ribosome entry site (IRES) sequence which facilitates translation of polynucleotide sequences positioned downstream of the IRES sequence. In this case, a transcribed polycistronic RNA molecule encoding the different polypeptides described above will be translated from both the capped 5' end and the two internal IRES sequences of the polycistronic RNA molecule to thereby produce in the cell all different polypeptides. Alternatively, the construct can include several promoter sequences each linked to a different exogenous polynucleotide sequence.

The plant cell transformed with the construct including a plurality of different exogenous polynucleotides, can be regenerated into a mature plant, using the methods described hereinabove.

Alternatively, expressing a plurality of exogenous polynucleotides in a single host plant can be effected by introducing different nucleic acid constructs, including different exogenous polynucleotides, into a plurality of plants. The regenerated transformed plants can then be cross-bred and resultant progeny selected for superior abiotic stress tolerance, water use efficiency, fertilizer use efficiency, growth, biomass, yield and/or vigor traits, using conventional plant breeding techniques.

According to some embodiments of the invention, the method further comprising growing the plant expressing the exogenous polynucleotide under the abiotic stress.

Non-limiting examples of abiotic stress conditions include, salinity, drought, water deprivation, excess of water (e.g., flood, waterlogging), etiolation, low temperature, high temperature, heavy metal toxicity, anaerobiosis, nutrient deficiency, nutrient excess, atmospheric pollution and UV irradiation.

Thus, the invention encompasses plants exogenously expressing the polynucleotide(s), the nucleic acid constructs and/or polypeptide(s) of the invention. Once expressed within the plant cell or the entire plant, the level of the polypeptide encoded by the exogenous polynucleotide can be determined by methods well known in the art such as, activity assays, Western blots using antibodies capable of specifically binding the polypeptide, Enzyme-Linked Immuno Sorbent Assay (ELISA), radio-immuno-assays (RIA), immunohistochemistry, immunocytochemistry, immunofluorescence and the like.

Methods of determining the level in the plant of the RNA transcribed from the exogenous polynucleotide are well known in the art and include, for example, Northern blot analysis, reverse transcription polymerase chain reaction (RT-PCR) analysis (including quantitative, semi-quantitative or real-time RT-PCR) and RNA-in situ hybridization.

The sequence information and annotations uncovered by the present teachings can be harnessed in favor of classical breeding. Thus, sub-sequence data of those polynucleotides described above, can be used as markers for marker assisted selection (MAS), in which a marker is used for indirect selection of a genetic determinant or determinants of a trait of interest (e.g., abiotic stress tolerance, increased yield, biomass, growth rate, vigor, oil content, fiber yield, fiber quality, and/or nitrogen use efficiency of a plant). Nucleic acid data of the present teachings (DNA or RNA sequence) may contain or be linked to polymorphic sites or genetic markers on the genome such as restriction fragment length polymorphism (RFLP), micro-satellites and single nucleotide polymorphism (SNP), DNA fingerprinting (DFP), amplified fragment length polymorphism (AFLP), expression level polymorphism, polymorphism of the encoded polypeptide and any other polymorphism at the DNA or RNA sequence.

Examples of marker assisted selections include, but are not limited to, selection for a morphological trait (e.g., a gene that affects form, coloration, male sterility or resistance such as the presence or absence of awn, leaf sheath coloration, height, grain color, aroma of rice); selection for a biochemical trait (e.g., a gene that encodes a protein that can be extracted and observed; for example, isozymes and storage proteins); selection for a biological trait (e.g., pathogen races or insect biotypes based on host pathogen or host parasite interaction can be used as a marker since the genetic constitution of an organism can affect its susceptibility to pathogens or parasites).

The polynucleotides and polypeptides described hereinabove can be used in a wide range of economical plants, in a safe and cost effective manner.

Plant lines exogenously expressing the polynucleotide or the polypeptide of the invention are screened to identify those that show the greatest increase of the desired plant trait.

The effect of the transgene (the exogenous polynucleotide encoding the polypeptide) on abiotic stress tolerance can be determined using known methods such as detailed below and in the Examples section which follows.

Abiotic Stress Tolerance

Transformed (i.e., expressing the transgene) and non-transformed (wild type) plants are exposed to an abiotic stress condition, such as water deprivation, suboptimal temperature (low temperature, high temperature), nutrient deficiency, nutrient excess, a salt stress condition, osmotic stress, heavy metal toxicity, anaerobiosis, atmospheric pollution and UV irradiation.

Salinity Tolerance Assay

Transgenic plants with tolerance to high salt concentrations are expected to exhibit better germination, seedling vigor or growth in high salt. Salt stress can be effected in many ways such as, for example, by irrigating the plants with a hyperosmotic solution, by cultivating the plants hydroponically in a hyperosmotic growth solution (e.g., Hoagland solution), or by culturing the plants in a hyperosmotic growth medium [e.g., 50% Murashige-Skoog medium (MS medium)]. Since different plants vary considerably in their tolerance to salinity, the salt concentration in the irrigation water, growth solution, or growth medium can be adjusted according to the specific characteristics of the specific plant cultivar or variety, so as to inflict a mild or moderate effect on the physiology and/or morphology of the plants (for guidelines as to appropriate concentration see, Bernstein and Kafkafi, Root Growth Under Salinity Stress In: Plant Roots, The Hidden Half 3rd ed. Waisel Y, Eshel A and Kafkafi U. (editors) Marcel Dekker Inc., New York, 2002, and reference therein).

For example, a salinity tolerance test can be performed by irrigating plants at different developmental stages with increasing concentrations of sodium chloride (for example 50 mM, 100 mM, 200 mM, 400 mM NaCl) applied from the bottom and from above to ensure even dispersal of salt. Following exposure to the stress condition the plants are frequently monitored until substantial physiological and/or morphological effects appear in wild type plants. Thus, the external phenotypic appearance, degree of wilting and overall success to reach maturity and yield progeny are compared between control and transgenic plants.

Quantitative parameters of tolerance measured include, but are not limited to, the average wet and dry weight, growth rate, leaf size, leaf coverage (overall leaf area), the weight of the seeds yielded, the average seed size and the number of seeds produced per plant. Transformed plants not exhibiting substantial physiological and/or morphological effects, or exhibiting higher biomass than wild-type plants, are identified as abiotic stress tolerant plants.

Osmotic Tolerance Test

Osmotic stress assays (including sodium chloride and mannitol assays) are conducted to determine if an osmotic stress phenotype was sodium chloride-specific or if it was a general osmotic stress related phenotype. Plants which are tolerant to osmotic stress may have more tolerance to drought and/or freezing. For salt and osmotic stress germination experiments, the medium is supplemented for example with 50 mM, 100 mM, 200 mM NaCl or 100 mM, 200 mM NaCl, 400 mM mannitol.

Drought Tolerance Assay/Osmoticum Assay

Tolerance to drought is performed to identify the genes conferring better plant survival after acute water deprivation. To analyze whether the transgenic plants are more tolerant to drought, an osmotic stress produced by the non-ionic osmolyte sorbitol in the medium can be performed. Control and transgenic plants are germinated and grown in plant-agar plates for 4 days, after which they are transferred to plates containing 500 mM sorbitol. The treatment causes growth retardation, then both control and transgenic plants are compared, by measuring plant weight (wet and dry), yield, and by growth rates measured as time to flowering.

Conversely, soil-based drought screens are performed with plants overexpressing the polynucleotides detailed above. Seeds from control *Arabidopsis* plants, or other transgenic plants overexpressing the polypeptide of the invention are germinated and transferred to pots. Drought stress is obtained after irrigation is ceased accompanied by placing the pots on absorbent paper to enhance the soil-drying rate. Transgenic and control plants are compared to each other when the majority of the control plants develop severe wilting. Plants are re-watered after obtaining a significant fraction of the control plants displaying a severe wilting. Plants are ranked comparing to controls for each of two criteria: tolerance to the drought conditions and recovery (survival) following re-watering.

Cold Stress Tolerance

To analyze cold stress, mature (25 day old) plants are transferred to 4° C. chambers for 1 or 2 weeks, with constitutive light. Later on plants are moved back to greenhouse. Two weeks later damages from chilling period, resulting in growth retardation and other phenotypes, are compared between both control and transgenic plants, by measuring plant weight (wet and dry), and by comparing growth rates measured as time to flowering, plant size, yield, and the like.

Heat Stress Tolerance

Heat stress tolerance is achieved by exposing the plants to temperatures above 34° C. for a certain period. Plant tolerance is examined after transferring the plants back to 22° C. for recovery and evaluation after 5 days relative to internal controls (non-transgenic plants) or plants not exposed to neither cold or heat stress.

Water Use Efficiency can be determined as the biomass produced per unit transpiration. To analyze WUE, leaf relative water content can be measured in control and transgenic plants. Fresh weight (FW) is immediately recorded; then leaves are soaked for 8 hours in distilled water at room temperature in the dark, and the turgid weight (TW) is recorded. Total dry weight (DW) is recorded after drying the leaves at 60° C. to a constant weight. Relative water content (RWC) is calculated according to the following Formula I:

$$RWC=[(FW-DW)/(TW-DW)]\times 100 \qquad \text{Formula I}$$

Fertilizer Use Efficiency

To analyze whether the transgenic plants are more responsive to fertilizers, plants are grown in agar plates or pots with a limited amount of fertilizer, as described, for example, in Example 6, hereinbelow and in Yanagisawa et al (Proc Natl Acad Sci USA. 2004; 101:7833-8). The plants are analyzed for their overall size, time to flowering, yield, protein content of shoot and/or grain. The parameters checked are the overall size of the mature plant, its wet and dry weight, the weight of the seeds yielded, the average seed size and the number of seeds produced per plant. Other parameters that may be tested are: the chlorophyll content of leaves (as nitrogen plant status and the degree of leaf verdure is highly correlated), amino acid and the total protein content of the seeds or other plant parts such as leaves or shoots, oil content, etc. Similarly, instead of providing nitrogen at limiting amounts, phosphate or potassium can be added at increasing concentrations. Again, the same parameters measured are the same as listed above. In this way, nitrogen use efficiency (NUE), phosphate use efficiency (PUE) and potassium use efficiency (KUE) are assessed, checking the ability of the transgenic plants to thrive under nutrient restraining conditions.

Nitrogen Use Efficiency

To analyze whether the transgenic *Arabidopsis* plants are more responsive to nitrogen, plant are grown in 0.75-1.5 mM (nitrogen deficient conditions) or 6-10 mM (optimal nitrogen concentration). Plants are allowed to grow for additional 20 days or until seed production. The plants are then analyzed for their overall size, time to flowering, yield, protein content of shoot and/or grain/seed production. The parameters checked can be the overall size of the plant, wet and dry weight, the weight of the seeds yielded, the average seed size and the number of seeds produced per plant. Other parameters that may be tested are: the chlorophyll content of leaves (as nitrogen plant status and the degree of leaf greenness is highly correlated), amino acid and the total protein content of the seeds or other plant parts such as leaves or shoots and oil content. Transformed plants not exhibiting substantial physiological and/or morphological effects, or exhibiting higher measured parameters levels than wild-type plants, are identified as nitrogen use efficient plants.

Nitrogen Use Efficiency Assay Using Plantlets

The assay is done according to Yanagisawa-S. et al. with minor modifications ("Metabolic engineering with Dof1 transcription factor in plants: Improved nitrogen assimilation and growth under low-nitrogen conditions" *Proc. Natl. Acad. Sci. USA* 101, 7833-7838). Briefly, transgenic plants which are grown for 7-10 days in 0.5×MS [Murashige-Skoog]

supplemented with a selection agent are transferred to two nitrogen-limiting conditions: MS media in which the combined nitrogen concentration ($NH_4NO_3$ and $KNO_3$) was 0.2 mM or 0.05 mM. Plants are allowed to grow for additional 30-40 days and then photographed, individually removed from the Agar (the shoot without the roots) and immediately weighed (fresh weight) for later statistical analysis. Constructs for which only T1 seeds are available are sown on selective media and at least 25 seedlings (each one representing an independent transformation event) are carefully transferred to the nitrogen-limiting media. For constructs for which T2 seeds are available, different transformation events are analyzed. Usually, 25 randomly selected plants from each event are transferred to the nitrogen-limiting media allowed to grow for 3-4 additional weeks and individually weighed at the end of that period. Transgenic plants are compared to control plants grown in parallel under the same conditions. Mock-transgenic plants expressing the uidA reporter gene (GUS) under the same promoter are used as control.

Nitrogen Determination

The procedure for N (nitrogen) concentration determination in the structural parts of the plants involves the potassium persulfate digestion method to convert organic N to $NO_3^-$ (Purcell and King 1996 Argon. J. 88:111-113, the modified $Cd^-$ mediated reduction of $NO_3^-$ to $NO_2^-$ (Vodovotz 1996 Biotechniques 20:390-394) and the measurement of nitrite by the Griess assay (Vodovotz 1996, supra). The absorbance values are measured at 550 nm against a standard curve of $NaNO_2$. The procedure is described in details in Samonte et al. 2006 Agron. J. 98:168-176.

Germination Tests

Germination tests compare the percentage of seeds from transgenic plants that could complete the germination process to the percentage of seeds from control plants that are treated in the same manner. Normal conditions are considered for example, incubations at 22° C. under 22-hour light 2-hour dark daily cycles. Evaluation of germination and seedling vigor is conducted between 4 and 14 days after planting. The basal media is 50% MS medium (Murashige and Skoog, 1962 Plant Physiology 15, 473-497).

Germination is checked also at unfavorable conditions such as cold (incubating at temperatures lower than 10° C. instead of 22° C.) or using seed inhibition solutions that contain high concentrations of an osmolyte such as sorbitol (at concentrations of 50 mM, 100 mM, 200 mM, 300 mM, 500 mM, and up to 1000 mM) or applying increasing concentrations of salt (of 50 mM, 100 mM, 200 mM, 300 mM, 500 mM NaCl).

The effect of the transgene on plant's vigor, growth rate, biomass, yield and/or oil content can be determined using known methods.

Plant Vigor

The plant vigor can be calculated by the increase in growth parameters such as leaf area, fiber length, rosette diameter, plant fresh weight and the like per time.

Growth Rate

The growth rate can be measured using digital analysis of growing plants. For example, images of plants growing in greenhouse on plot basis can be captured every 3 days and the rosette area can be calculated by digital analysis. Rosette area growth is calculated using the difference of rosette area between days of sampling divided by the difference in days between samples.

Evaluation of growth rate can be done by measuring plant biomass produced, rosette area, leaf size or root length per time (can be measured in $cm^2$ per day of leaf area).

Relative growth area can be calculated using Formula II.

Relative growth rate area=Regression coefficient of area along time course    Formula II Thus, the relative growth area rate is in units of 1/day and length growth rate is in units of 1/day.

Seed Yield

Evaluation of the seed yield per plant can be done by measuring the amount (weight or size) or quantity (i.e., number) of dry seeds produced and harvested from 8-16 plants and divided by the number of plants.

For example, the total seeds from 8-16 plants can be collected, weighted using e.g., an analytical balance and the total weight can be divided by the number of plants. Seed yield per growing area can be calculated in the same manner while taking into account the growing area given to a single plant. Increase seed yield per growing area could be achieved by increasing seed yield per plant, and/or by increasing number of plants capable of growing in a given area.

In addition, seed yield can be determined via the weight of 1000 seeds. The weight of 1000 seeds can be determined as follows: seeds are scattered on a glass tray and a picture is taken. Each sample is weighted and then using the digital analysis, the number of seeds in each sample is calculated.

The 1000 seeds weight can be calculated using formula III:

1000 Seed Weight=number of seed in sample/sample weight×1000    Formula III

The Harvest Index can be calculated using Formula IV

Harvest Index=Average seed yield per plant/Average dry weight    Formula IV

Grain Protein Concentration

Grain protein content (g grain protein $m^{-2}$) is estimated as the product of the mass of grain N (g grain N $m^{-2}$) multiplied by the N/protein conversion ratio of k–5.13 (Mosse 1990, supra). The grain protein concentration is estimated as the ratio of grain protein content per unit mass of the grain (g grain protein $kg^{-1}$ grain).

Fiber Length

Fiber length can be measured using fibrograph. The fibrograph system was used to compute length in terms of "Upper Half Mean" length. The upper half mean (UHM) is the average length of longer half of the fiber distribution. The fibrograph measures length in span lengths at a given percentage point (Hypertext Transfer Protocol://World Wide Web (dot) cottoninc (dot) com/ClassificationofCotton/?Pg=4#Length).

According to some embodiments of the invention, increased yield of corn may be manifested as one or more of the following: increase in the number of plants per growing area, increase in the number of ears per plant, increase in the number of rows per ear, number of kernels per ear row, kernel weight, thousand kernel weight (1000-weight), ear length/diameter, increase oil content per kernel and increase starch content per kernel.

As mentioned, the increase of plant yield can be determined by various parameters. For example, increased yield of rice may be manifested by an increase in one or more of the following: number of plants per growing area, number of panicles per plant, number of spikelets per panicle, number of flowers per panicle, increase in the seed filling rate, increase in thousand kernel weight (1000-weight), increase oil content per seed, increase starch content per seed, among others. An increase in yield may also result in modified architecture, or may occur because of modified architecture.

Similarly, increased yield of soybean may be manifested by an increase in one or more of the following: number of plants per growing area, number of pods per plant, number of seeds per pod, increase in the seed filling rate, increase in thousand seed weight (1000-weight), reduce pod shattering, increase oil content per seed, increase protein content per seed, among others. An increase in yield may also result in modified architecture, or may occur because of modified architecture.

Increased yield of canola may be manifested by an increase in one or more of the following: number of plants per growing area, number of pods per plant, number of seeds per pod, increase in the seed filling rate, increase in thousand seed weight (1000-weight), reduce pod shattering, increase oil content per seed, among others. An increase in yield may also result in modified architecture, or may occur because of modified architecture.

Increased yield of cotton may be manifested by an increase in one or more of the following: number of plants per growing area, number of bolls per plant, number of seeds per boll, increase in the seed filling rate, increase in thousand seed weight (1000-weight), increase oil content per seed, improve fiber length, fiber strength, among others. An increase in yield may also result in modified architecture, or may occur because of modified architecture.

Oil Content

The oil content of a plant can be determined by extraction of the oil from the seed or the vegetative portion of the plant. Briefly, lipids (oil) can be removed from the plant (e.g., seed) by grinding the plant tissue in the presence of specific solvents (e.g., hexane or petroleum ether) and extracting the oil in a continuous extractor. Indirect oil content analysis can be carried out using various known methods such as Nuclear Magnetic Resonance (NMR) Spectroscopy, which measures the resonance energy absorbed by hydrogen atoms in the liquid state of the sample [See for example, Conway T F. and Earle F R., 1963, Journal of the American Oil Chemists' Society; Springer Berlin/Heidelberg, ISSN: 0003-021X (Print) 1558-9331 (Online)]; the Near Infrared (NI) Spectroscopy, which utilizes the absorption of near infrared energy (1100-2500 nm) by the sample; and a method described in WO/2001/023884, which is based on extracting oil a solvent, evaporating the solvent in a gas stream which forms oil particles, and directing a light into the gas stream and oil particles which forms a detectable reflected light.

Thus, the present invention is of high agricultural value for promoting the yield of commercially desired crops (e.g., biomass of vegetative organ such as poplar wood, or reproductive organ such as number of seeds or seed biomass).

Any of the transgenic plants described hereinabove or parts thereof may be processed to produce a feed, meal, protein or oil preparation, such as for ruminant animals.

The transgenic plants described hereinabove, which exhibit an increased oil content can be used to produce plant oil (by extracting the oil from the plant).

The plant oil (including the seed oil and/or the vegetative portion oil) produced according to the method of the invention may be combined with a variety of other ingredients. The specific ingredients included in a product are determined according to the intended use. Exemplary products include animal feed, raw material for chemical modification, biodegradable plastic, blended food product, edible oil, biofuel, cooking oil, lubricant, biodiesel, snack food, cosmetics, and fermentation process raw material. Exemplary products to be incorporated to the plant oil include animal feeds, human food products such as extruded snack foods, breads, as a food binding agent, aquaculture feeds, fermentable mixtures, food supplements, sport drinks, nutritional food bars, multi-vitamin supplements, diet drinks, and cereal foods.

According to some embodiments of the invention, the oil comprises a seed oil.

According to some embodiments of the invention, the oil comprises a vegetative portion oil.

According to some embodiments of the invention, the plant cell forms a part of a plant.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", an and the include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Identifying Putative Genes which Increase Abiotic Stress Tolerance, Yield, Biomass, Growth Rate and/or Fiber Development and Quality The present inventors have identified genes which increase abiotic stress-tolerance (ABST), growth rate, biomass, fiber development or quality, vigor, yield (e.g., seed yield, oil yield), oil content, and nitrogen use efficiency. All nucleotide sequence datasets used here were originated from publicly available databases. Sequence data from 80 different plant species was introduced into a single, comprehensive database. Other information on gene expression, protein annotation, enzymes and pathways were also incorporated. Major databases used include:

Genomes
  *Arabidopsis* genome [TAIR genome version 6 (Hypertext Transfer Protocol://World Wide Web (dot) *arabidopsis* (dot) org/)]
  Rice genome [IRGSP build 4.0 (Hypertext Transfer Protocol://rgp (dot) dna (dot) affrc (dot) go (dot) jp/IRGSP/)].
  Poplar [*Populus trichocarpa* release 1.1 from JGI (assembly release v1.0) (Hypertext Transfer Protocol://World Wide Web (dot) genome (dot) jgi-psf (dot) org/)]
  Brachypodium [JGI 4× assembly Hypertext Transfer Protocol://World Wide Web (dot) brachpodium (dot) org)]
  Soybean [DOE-JGI SCP, version Glyma0 (Hypertext Transfer Protocol://World Wide Web (dot) phytozome (dot) net/)]
  Grape International Grape Genome Program Genome Assembly (Hypertext Transfer Protocol://World Wide Web (dot) genoscope (dot) cns (dot) fr/externe/Download/Projets/Projet_mL/data/assembly/
  Castobean [TIGR/J Craig Venter Institute 4× assembly (Hypertext Transfer Protocol://msc (dot) jcv (dot) org/)]
  *Sorghum* [DOE-JGI SCP, version Sbi1 Hypertext Transfer Protocol://World Wide Web (dot) phytozome (dot) net/)].
  Partially assembled genome of Maize [Hypertext Transfer Protocol://maizesequence (dot) org/]
  Expressed EST and mRNA Sequences were Extracted from
  GeneBank versions 154, 157, 160, 161, 164, 165, 166 (Hypertext Transfer Protocol://World Wide Web (dot) ncbi (dot) nlm (dot) nih (dot) gov/dbEST/)
  RefSeq (Hypertext Transfer Protocol://World Wide Web (dot) ncbi (dot) nlm (dot) nih (dot) gov/RefSeq/).
  TAIR (Hypertext Transfer Protocol://World Wide Web (dot) *arabidopsis* (dot) org/).
  Protein and Pathway Databases
  Uniprot (Hypertext Transfer Protocol://World Wide Web.expasy.uniprot.org/).
  AraCyc (Hypertext Transfer Protocol://World Wide Web (dot) *arabidopsis* (dot) org/biocyc/index (dot) jsp).
  ENZYME (Hypertext Transfer Protocol://expasy.org/enzyme/).
  Microarray Datasets were Downloaded from
  GEO (Hypertext Transfer Protocol://World Wide Web.ncbi.nlm.nih.gov/geo/)
  TAIR (Hypertext Transfer Protocol://World Wide Web.arabidopsis.org/).
  Proprietary cotton fiber microarray data
  QTL Information
  Gramene (Hypertext Transfer Protocol://World Wide Web (dot) gramene (dot) org/qtl/).
  Database Assembly was performed to build a wide, rich, reliable annotated and easy to analyze database comprised of publicly available genomic mRNA, ESTs DNA sequences, data from various crops as well as gene expression, protein annotation and pathway data QTLs, and other relevant information.

Database assembly is comprised of a toolbox of gene refining, structuring, annotation and analysis tools enabling to construct a tailored database for each gene discovery project. Gene refining and structuring tools enable to reliably detect splice variants and antisense transcripts, generating understanding of various potential phenotypic outcomes of a single gene. The capabilities of the "LEADS" platform of Compugen LTD for analyzing human genome have been confirmed and accepted by the scientific community ("Widespread Antisense Transcription", Yelin, et al. (2003) Nature Biotechnology 21, 379-85; "Splicing of Alu Sequences", Lev-Maor, et al. (2003) Science 300 (5623), 1288-91; "Computational analysis of alternative splicing using EST tissue information", Xie H et al. Genomics 2002), and have been proven most efficient in plant genomics as well.

EST Clustering and Gene Assembly

For gene clustering and assembly of organisms with available genome sequence data (*arabidopsis*, rice, castorbean, grape, brachypodium, poplar, soybean, *sorghum*) the genomic LEADS version (GANG) was employed. This tool allows most accurate clustering of ESTs and mRNA sequences on genome, and predicts gene structure as well as alternative splicing events and anti-sense transcription.

For organisms with no available full genome sequence data, "expressed LEADS" clustering software was applied.

Gene Annotation

Predicted genes and proteins were annotated as follows:

Blast search (Hypertext Transfer Protocol://World Wide Web (dot) ncbi (dot) nlm (dot) nih (dot) gov (dot) library (dot) vu (dot) edu (dot) au/BLAST/) against all plant UniProt (Hypertext Transfer Protocol://World Wide Web (dot) expasy (dot) uniprot (dot) org/) sequences was performed.

Open reading frames of each putative transcript were analyzed and longest ORF with higher number of homolgs was selected as predicted protein of the transcript.

The predicted proteins were analyzed by InterPro (Hypertext Transfer Protocol://World Wide Web (dot) ebi (dot) ac (dot) uk/interpro/).

Blast against proteins from AraCyc and ENZYME databases was used to map the predicted transcripts to AraCyc pathways.

Predicted proteins from different species were compared using blast algorithm (Hypertext Transfer Protocol://World Wide Web (dot) ncbi (dot) nlm (dot) nih (dot) gov (dot) library (dot) vu (dot) edu (dot) au/BLAST/) to validate the accuracy of the predicted protein sequence, and for efficient detection of orthologs.

Gene Expression Profiling

Few data sources were exploited for gene expression profiling, namely microarray data and digital expression profile (see below). According to gene expression profile, a correlation analysis was performed to identify genes which are co-regulated under different development stages and environmental conditions.

Publicly available microarray datasets were downloaded from TAIR and NCBI GEO sites, renormalized, and integrated into the database. Expression profiling is one of the most important resource data for identifying genes important for ABST. Moreover, when homolog genes from different crops were responsive to ABST, the genes are marked as "highly predictive to improve ABST".

A digital expression profile summary was compiled for each cluster according to all keywords included in the sequence records comprising the cluster. Digital expression, also known as electronic Northern Blot, is a tool that displays virtual expression profile based on the EST sequences forming the gene cluster. The tool can provide the expression profile of a cluster in terms of plant anatomy (in what tissues/organs is the gene expressed), developmental stage (the developmental stages at which a gene can be found) and profile of treatment (provides the physiological conditions under which a gene is expressed such as drought, cold, pathogen infection, etc). Given a random distribution of ESTs in the different clusters, the digital expression provides a probability value that describes the probability of a cluster having a total of N ESTs to contain X ESTs from a certain collection of libraries. For the probability calculations are taken into consideration: a) the number of ESTs in the cluster, b) the number of ESTs of the implicated and related libraries, c) the overall number of ESTs available representing the species. Thereby clusters with low probability values are highly enriched with ESTs from the group of libraries of interest indicating a specialized expression.

The results of the digital and microarray gene expression data are provided in Tables 1-4, hereinbelow.

Below are summarized the key criteria used to select the genes which expression thereof in a plant can be used to increase ABST, WUE, NUE, FUE, biomass, yield and oil content. The overexpression Fold ("Fold") is calculated as the ratio between the number of ESTs found in a gene or an orthologue group for a certain category ("Keyword") and the number of expected ESTs according to a normal distribution. A probabilistic value (P-value) was estimated for the calculated overexpression folds. Genes were selected based on the results presented in Tables 1-4 below and other computational filtering combined with manual curation as detailed below.

LAB25, LAB31, LAB33, LAB34, LAB45 and LAB51 were selected since they are highly expressed in roots and under drought stress conditions (as shown in Table 1 hereinbelow).

TABLE 1

Digital expression of LAB25, LAB31, LAB33, LAB34, LAB45 and LAB51 in roots and under drought stress

| Genes | Anatomy Root | | Treatment Drought stress | |
|---|---|---|---|---|
| | fold | p-value | fold | p-value |
| LAB25 | 5.39 | 1.125E−52 | 1.984434 | 0.0404051 |
| LAB31 | 10.00 | 6.034E−09 | 7.00 | 8.6157E−06 |
| LAB33 | 2.66 | 7.272E−05 | 3.25 | 0.00090165 |
| LAB34 | 3.38 | 1.474E−05 | 9.55 | 6.8734E−08 |
| LAB45 | 2.22 | 1.7E−07 | 14.11 | 4.2333E−14 |
| LAB51 | 2.10 | 0.0046312 | 4.00 | 0.0131351 |

Table 1. Digital expression of the indicated genes in root and under drought stress. Provided are the fold increase and the calculated p-values of expression of the gene in the indicated tissue or condition as compared to the randomly expected expression. Results were considered statistically significant if the p-value was lower than 0.05.

LAB4, LAB7, LAB 14 and LAB49 were selected since they are highly expressed in roots and under UV radiation, cold stress or heat stress (as shown in Table 2 hereinbelow).

TABLE 2

Digital expression of LAB4, LAB7, LAB14 and LAB49 in roots, under UV irradiation, cold stress or heat stress

| | Anatomy | | Treatment | | | | | |
|---|---|---|---|---|---|---|---|---|
| | Root | | UV irradiation | | Cold stress | | Heat stress | |
| Genes | fold | p-value | fold | p-value | fold | p-value | fold | p-value |
| LAB4 | 4.45 | 2.005E−10 | | | | | | |
| LAB7 | 2.48 | 6.421E−08 | | | 2.37 | 0.0303 | | |

TABLE 2-continued

Digital expression of LAB4, LAB7, LAB14 and LAB49 in roots, under UV irradiation, cold stress or heat stress

| | Anatomy | | Treatment | | | | | |
|---|---|---|---|---|---|---|---|---|
| | Root | | UV irradiation | | Cold stress | | Heat stress | |
| Genes | fold | p-value | fold | p-value | fold | p-value | fold | p-value |
| LAB14 | 2.15 | 0.0319954 | 3.64 | 0.00019 | | | 2 | 0.0570 |
| LAB49 | 4.17 | 8.6877E−11 | | | | | | |

Table 2. Digital expression of the indicated genes in roots, under UV irradiation, cold stress or heat stress. Provided are the fold increase and the calculated p-values of expression of the gene in the indicated tissue or condition as compared to the randomly expected expression. Results were considered statistically significant if the p-value was lower than 0.05. Blank cells indicate that either the gene is not expressed or data is not available.

LAB5, LAB13, LAB16, LAB18, LAB20, LAB22, LAB3, LAB24, LAB35, LAB38, LAB39, LAB40, LAB50 and LAB51 were selected since they are highly expressed under drought stress and possibly nutrient deficiencies, cold stress or plant development or stress hormones (as shown in Table 3 hereinbelow).

TABLE 3

Digital expression of LAB5, LAB13, LAB16, LAB18, LAB20, LAB22, LAB3, LAB24, LAB35, LAB38, LAB39, LAB40, LAB50 and LAB51 under drought stress and possibly nutrient deficiencies, cold stress or plant development or stress hormones

| | Drought stress | | Nutrient deficiencies | | Cold stress | | Plant development or stress hormones | |
|---|---|---|---|---|---|---|---|---|
| | fold | | p-value | | | | | |
| | 3.46 | 0.00188373 | fold | p-value | fold | p-value | fold | p-value |
| LAB5 | 3.13 | 0.0400183 | | | | | | |
| LAB13 | 3.00 | 0.00017491 | | | | | | |
| LAB16 | 4.00 | 0.00458478 | | | | | | |
| LAB18 | 4.95 | 4.2144E−05 | | | | | | |
| LAB20 | 8.88 | 3.4638E−22 | | | | | | |
| LAB22 | 3.00 | 0.00978408 | | | | | 3.17 | 0.0379553 |
| LAB3 | 2.37 | 5.7818E−08 | | | | | | |
| LAB24 | 14.11 | 4.2333E−14 | | | | | | |
| LAB35 | 4.00 | 0.00207373 | | | | | 3.00 | 0.0072537 |
| LAB38 | 2.35 | 0.00067594 | | | | | | |
| LAB39 | 8.93 | 2.6849E−08 | | | 3.06 | 0.0144515 | | |
| LAB40 | 7.00 | 5.6733E−05 | | | | | | |
| LAB50 | 3.44 | 1.1207E−06 | | | | | 3.15 | 0.012142 |

Table 3. Digital expression of the indicated genes under drought stress, possibly nutrient deficiencies, cold stress or plant development or stress hormones. Provided are the fold increase and the calculated p-values of expression of the gene in the indicated tissue or condition as compared to the randomly expected expression. Results were considered statistically significant if the p-value was lower than 0.05. Blank cells indicate that either the gene is not expressed or data is not available.

LAB9, LAB21, LAB32, LAB15, LAB17, LAB30, LAB36, and LAB39 were selected since they are highly expressed under etiolatlion condition, plant development or stress hormones, salinity stress or waterlogging (as shown in Table 4 hereinbelow).

TABLE 4

Digital expression of LAB9, LAB21, LAB32, LAB15, LAB17, LAB30, LAB36, and LAB39 under etiolatlion condition, plant development or stress hormones, salinity stress or waterlogging

| | Etiolated | | Plant development or stress hormones | | Salinity stress | | Waterlogging | |
|---|---|---|---|---|---|---|---|---|
| | fold | | p-value | | | | | |
| | 2.91 | 0.0160756 | fold | p-value | fold | p-value | fold | p-value |
| LAB9 | 2.23 | 0.00043618 | | | | | | |
| LAB21 | 4.65 | 5.5967E−17 | | | | | | |
| LAB32 | | | | | | | | |
| LAB15 | | | | | | | 1.0 | 0.0705542 |

TABLE 4-continued

Digital expression of LAB9, LAB21, LAB32, LAB15, LAB17, LAB30, LAB36, and LAB39 under etiolatlion condition, plant development or stress hormones, salinity stress or waterlogging

| | Etiolated | | Plant development or stress hormones | | Salinity stress | | Waterlogging | |
|---|---|---|---|---|---|---|---|---|
| | fold | p-value | fold | p-value | fold | p-value | fold | p-value |
| | 2.91 | 0.0160756 | | | | | | |
| LAB17 | | | | | | | 2.0 | 0.0420927 |
| LAB30 | | | 6.00 | 7.4196E−05 | | | | |
| LAB36 | | | 3.66 | 3.338E−06 | | | 4.7 | 9.3682E−06 |
| LAB39 | | | | | | | | |

Table 4. Digital expression of the indicated genes under etiolatlion condition, plant development or stress hormones, salinity stress or waterlogging. Provided are the fold increase and the calculated p-values of expression of the gene in the indicated tissue or condition as compared to the randomly expected expression. Results were considered statistically significant if the p-value was lower than 0.05. Blank cells indicate that either the gene is not expressed or data is not available.

Overall, 51 genes were identified to have a major impact on ABST, nitrogen use efficiency, yield (e.g., seed yield), oil content, growth rate and/or vigor when overexpressed in plants. The identified genes, their curated polynucleotide and polypeptide sequences, as well as their updated sequences according to Genebank database are summarized in Table 5, hereinbelow.

TABLE 5

Identified genes which can be used to increase ABST, fiber development (quality and yield), yield, biomass, growth rate, nitrogen use efficiency, fertilizer use efficiency, water use efficiency, and/or oil content of a plant

| Gene Name | Cluster Name | Organism | SEQ ID NO: Polynuc. | SEQ ID NO: Polypep. |
|---|---|---|---|---|
| LAB4 | rice\|gb157.2\|AA751809 | rice | 1 | 60 |
| LAB5 | sorghum\|gb161.xeno\|AW922806 | sorghum | 2 | 61 |
| LAB7 | rice\|gb157.2\|AA754242 | rice | 3 | 62 |
| LAB8 | rice\|gb157.2\|AA754407 | rice | 4 | 63 |
| LAB9 | rice\|gb157.2\|AB004799 | rice | 5 | 64 |
| LAB11 | rice\|gb157.2\|AK070868 | rice | 6 | 65 |
| LAB13 | rice\|gb157.2\|AT003625 | rice | 7 | 66 |
| LAB14 | rice\|gb157.2\|AU056017 | rice | 8 | 67 |
| LAB15 | barley\|gb157.3\|BF623077 | barley | 9 | 68 |
| LAB2 | barley\|gb157.3\|BE195266 | barley | 10 | 69 |
| LAB16 | cotton\|gb164\|BE052656 | cotton | 11 | 70 |
| LAB17 | sorghum\|gb161.xeno\|AI724026 | sorghum | 12 | 71 |
| LAB18 | sorghum\|gb161.xeno\|BE359151 | sorghum | 13 | 72 |
| LAB20 | rice\|gb157.2\|AW070136 | rice | 14 | 73 |
| LAB21 | barley\|gb157.3\|BE421259 | barley | 15 | 74 |
| LAB22 | sorghum\|gb161.xeno\|AW678130 | sorghum | 16 | 75 |
| LAB3 | canola\|gb161\|CD831005 | canola | 17 | 76 |
| LAB23 | barley\|gb157.3\|BI947386 | barley | 18 | 77 |
| LAB24 | sorghum\|gb161.xeno\|AW433371 | sorghum | 19 | 78 |
| LAB25 | barley\|gb157.3\|X84056 | barley | 20 | 79 |
| LAB30 | sorghum\|gb161.xeno\|BE362140 | sorghum | 21 | 80 |
| LAB31 | canola\|gb161\|H74460 | canola | 22 | 81 |
| LAB32 | barley\|gb157.3\|AL499903 | barley | 23 | 82 |
| LAB33 | sorghum\|gb161.xeno\|AW676682 | sorghum | 24 | 83 |
| LAB34 | soybean\|gb166\|CF921741 | soybean | 25 | 84 |
| LAB35 | wheat\|gb164\|BE497867 | wheat | 26 | 85 |
| LAB36 | sorghum\|gb161.xeno\|H55004 | sorghum | 27 | 86 |
| LAB38 | wheat\|gb164\|BE412185 | wheat | 28 | 87 |
| LAB39 | sorghum\|gb161.xeno\|BG048297 | sorghum | 29 | 88 |
| LAB40 | wheat\|gb164\|BE488436 | wheat | 30 | 89 |
| LAB41 | wheat\|gb164\|X52472 | wheat | 31 | 90 |
| LAB43 | barley\|gb157.3\|BF624177 | barley | 32 | 91 |
| LAB45 | sorghum\|gb161.crp\|AI855293 | sorghum | 33 | 92 |
| LAB49 | rice\|gb157.2\|BE040470 | rice | 34 | 93 |
| LAB50 | rice\|gb157.2\|BI305323 | rice | 35 | 94 |
| LAB51 | wheat\|gb164\|BI751966 | wheat | 36 | 95 |
| BDL103_P1 | rice\|gb157.2\|BE228840 | rice | 37 | 96 |
| BDL11 | arabidopsis\|gb165\|AT5G12460 | arabidopsis | 38 | 97 |
| BDL12 | arabidopsis\|gb165\|AT4G08530 | arabidopsis | 39 | 98 |
| BDL14 | arabidopsis\|gb165\|AT1G53690 | arabidopsis | 40 | 99 |
| BDL166 | arabidopsis\|gb165\|AT1G71691 | arabidopsis | 41 | 100 |
| BDL17 | arabidopsis\|gb165\|AT5G36680 | arabidopsis | 42 | 101 |
| BDL210 | arabidopsis\|gb165\|AT5G22810 | arabidopsis | 43 | 102 |
| CTF113 | cotton\|gb164\|AI727515 | cotton | 44 | 103 |

TABLE 5-continued

Identified genes which can be used to increase ABST, fiber development (quality and yield), yield, biomass, growth rate, nitrogen use efficiency, fertilizer use efficiency, water use efficiency, and/or oil content of a plant

| Gene Name | Cluster Name | Organism | SEQ ID NO: Polynuc. | SEQ ID NO: Polypep. |
|---|---|---|---|---|
| CTF163 | cotton\|gb164\|CO123733 | cotton | 45 | 104 |
| CTF175 | cotton\|gb164\|AW187393 | cotton | 46 | 105 |
| CTF180 | cotton\|gb164\|BG440663 | cotton | 47 | 106 |
| CTF205 | cotton\|gb164\|AI725800 | cotton | 48 | 107 |
| CTF215 | cotton\|gb164\|AI729467 | cotton | 49 | 108 |
| CTF225 | cotton\|gb164\|AW187127 | cotton | 50 | 109 |
| CTF226 | cotton\|gb164\|AI730124 | cotton | 51 | 110 |
| LAB2 | barley\|gb157.3\|BE195266 | barley | 52 | 69 |
| LAB3 | canola\|gb161\|CD831005 | canola | 53 | 76 |
| LAB32 | barley\|gb157.3\|AL499903 | barley | 54 | 82 |
| LAB38 | wheat\|gb164\|BE412185 | wheat | 55 | 87 |
| LAB51 | wheat\|gb164\|BI751966 | wheat | 56 | 95 |
| BDL17 | arabidopsis\|gb165\|AT5G36680 | *arabidopsis* | 57 | 111 |
| CTF163 | cotton\|gb164\|CO123733 | cotton | 58 | 104 |
| CTF205 | cotton\|gb164\|AI725800 | cotton | 59 | 112 |
| BDL103_P2 | rice\|gb157.2\|BE228840 | rice | 638 | 96 |

Table 5. Provided are the identified genes, their annotation, organism and polynucleotide and polypeptide sequence identifiers. SEQ ID NOs: 52-59 are polynucleotide sequences which were uncovered after cloning the gene. SEQ ID NO: 638 is a computational curated sequence.

Example 2

Identification of Homologues which Affect RBST, WUE, NUE, FUE, Yield, Growth Rate, Vigor, Biomass and Oil Content The concepts of orthology and paralogy have been applied to functional characterizations and classifications on the scale of whole-genome comparisons. Orthologs and paralogs constitute two major types of homologs: The first evolved from a common ancestor by specialization, and the latter are related by duplication events. It is assumed that paralogs arising from ancient duplication events are likely to have diverged in function while true orthologs are more likely to retain identical function over evolutionary time.

To further investigate and identify putative ortholog genes of genes affecting abiotic stress tolerance, nitrogen use efficiency, fertilizer use efficiency, yield (e.g., seed yield, oil yield, biomass, grain quantity and/or quality), growth rate, vigor, biomass, oil content, and/or water use efficiency (presented in Table 5, above) all sequences were aligned using the BLAST (/Basic Local Alignment Search Tool/). Sequences sufficiently similar were tentatively grouped. These putative orthologs were further organized under a Phylogram—a branching diagram (tree) assumed to be a representation of the evolutionary relationships among the biological taxa. Putative ortholog groups were analyzed as to their agreement with the phylogram and in cases of disagreements these ortholog groups were broken accordingly. Expression data was analyzed and the EST libraries were classified using a fixed vocabulary of custom terms such as developmental stages (e.g., genes showing similar expression profile through development with up regulation at specific stage, such as at the seed filling stage) and/or plant organ (e.g., genes showing similar expression profile across their organs with up regulation at specific organs such as root). The annotations from all the ESTs clustered to a gene were analyzed statistically by comparing their frequency in the cluster versus their abundance in the database, allowing the construction of a numeric and graphic expression profile of that gene, which is termed "digital expression". The rationale of using these two complementary methods with methods of phenotypic association studies of QTLs, and phenotype expression correlation is based on the assumption that true orthologs are likely to retain identical function over evolutionary time. These methods provide different sets of indications on function similarities between two homologous genes, similarities in the sequence level—identical amino acids in the protein domains and similarity in expression profiles.

The search and identification of homologous genes involves the screening of sequence information available, for example, in public databases, which include but are not limited to the DNA Database of Japan (DDBJ), Genbank, and the European Molecular Biology Laboratory Nucleic Acid Sequence Database (EMBL) or versions thereof or the MIPS database. A number of different search algorithms have been developed, including but not limited to the suite of programs referred to as BLAST programs. There are five implementations of BLAST, three designed for nucleotide sequence queries (BLASTN, BLASTX, and TBLASTX) and two designed for protein sequence queries (BLASTP and TBLASTN) (Coulson, Trends in Biotechnology: 76-80, 1994; Birren et al., Genome Analysis, I: 543, 1997). Such methods involve alignment and comparison of sequences. The BLAST algorithm calculates percent sequence identity and performs a statistical analysis of the similarity between the two sequences. The software for performing BLAST analysis is publicly available through the National Centre for Biotechnology Information. Other such software or algorithms are GAP, BESTFIT, FASTA and TFASTA. GAP uses the algorithm of Needleman and Wunsch (J. Mol. Biol. 48: 443-453, 1970) to find the alignment of two complete sequences that maximizes the number of matches and minimizes the number of gaps.

The homologous genes may belong to the same gene family. The analysis of a gene family may be carried out using sequence similarity analysis. To perform this analysis one may use standard programs for multiple alignments e.g. Clustal W. A neighbor-joining tree of the proteins homologous to the genes of some embodiments of the invention may be used to provide an overview of structural and ancestral relationships. Sequence identity may be calculated using an alignment program as described above. It is expected that other plants will carry a similar functional gene (orthologue)

or a family of similar genes and those genes will provide the same preferred phenotype as the genes presented here. Advantageously, these family members may be useful in the methods of some embodiments of the invention. Example of other plants include, but not limited to, barley (*Hordeum vulgare*), Arabidopsis (*Arabidopsis thaliana*), maize (*Zea mays*), cotton (*Gossypium*), Oilseed rape (*Brassica napus*), Rice (*Oryza sativa*), Sugar cane (*Saccharum officinarum*), Sorghum (*Sorghum bicolor*), Soybean (*Glycine max*), Sunflower (*Helianthus annuus*), Tomato (*Lycopersicon esculentum*) and Wheat (*Triticum aestivum*).

The above-mentioned analyses for sequence homology is preferably carried out on a full-length sequence, but may also be based on a comparison of certain regions such as conserved domains. The identification of such domains would also be well within the realm of the person skilled in the art and would involve, for example, a computer readable format of the nucleic acids of some embodiments of the invention, the use of alignment software programs and the use of publicly available information on protein domains, conserved motifs and boxes. This information is available in the PRODOM (Hypertext Transfer Protocol://World Wide Web (dot) biochem (dot) ucl (dot) ac (dot) uk/bsm/dbbrowser/protocol/prodomqry (dot) html), PIR (Hypertext Transfer Protocol://pir (dot) Georgetown (dot) edu/) or Pfam (Hypertext Transfer Protocol://World Wide Web (dot) sanger (dot) ac (dot) uk/Software/Pfam/) database. Sequence analysis programs designed for motif searching may be used for identification of fragments, regions and conserved domains as mentioned above. Preferred computer programs include, but are not limited to, MEME, SIGNALSCAN, and GENESCAN.

A person skilled in the art may use the homologous sequences provided herein to find similar sequences in other species and other organisms. Homologues of a protein encompass peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (conservative changes, such as similar hydrophobicity, hydrophilicity, antigenicity, propensity to form or break a-helical structures or 3-sheet structures). Conservative substitution Tables are well known in the art [see for example Creighton (1984) Proteins. W.H. Freeman and Company]. Homologues of a nucleic acid encompass nucleic acids having nucleotide substitutions, deletions and/or insertions relative to the unmodified nucleic acid in question and having similar biological and functional activity as the unmodified nucleic acid from which they are derived.

Table 6, hereinbelow, lists a summary of orthologous and homologous sequences of the polynucleotide sequences (SEQ ID NOs:1-59 and 638) and polypeptide sequences (SEQ ID NOs:60-112) presented in Table 5, which were identified using NCBI BLAST (BlastP) and needle (EMBOSS package) having at least 80% identity to the selected polypeptides and which are expected to posses the same role in abiotic stress tolerance (ABST), water use efficiency (WUE), nitrogen use efficiency (NUE), fertilizer use efficiency (FUE), biomass increment, growth rate increment, yield, vigor, fiber quality and/or yield and/or oil content of plants.

TABLE 6

Homologues of the identified genes of the invention which can increase ABST, fiber development (quality and yield), biomass, growth rate, nitrogen use efficiency, fertilizer use efficiency, water use efficiency, yield and/or oil content of a plant

| Polynucl. SEQ ID NO: | Gene Name | Organism/Cluster name | Polypep. SEQ ID NO: | Homology to SEQ ID NO: | % Global identity | Algor. |
|---|---|---|---|---|---|---|
| 113 | LAB4_H0 | sorghum\|gb161.crp\|AW747731 | 359 | 60 | 82.6 | blastp |
| 114 | LAB4_H1 | switchgrass\|gb167\|DN143443 | 360 | 60 | 81.6 | blastp |
| 115 | LAB5_H0 | barley\|gb157.3\|BE412466 | 361 | 61 | 83.1 | blastp |
| 116 | LAB5_H1 | barley\|gb157.3\|BF623020 | 362 | 61 | 82.3 | blastp |
| 117 | LAB5_H2 | barley\|gb157.3\|BI953964 | 363 | 61 | 82.3 | blastp |
| 118 | LAB5_H3 | brachypodium\|gb169\|AF181661 | 364 | 61 | 85.61 | tblastn |
| 119 | LAB5_H4 | cenchrus\|gb166\|BM084156 | 365 | 61 | 85.1 | blastp |
| 120 | LAB5_H5 | fescue\|gb161\|DT683694 | 366 | 61 | 87.7 | blastp |
| 121 | LAB5_H6 | maize\|gb170\|BI325281 | 367 | 61 | 94.7 | blastp |
| 122 | LAB5_H7 | rice\|gb170\|OS06G46950 | 368 | 61 | 82.3 | blastp |
| 123 | LAB5_H8 | rye\|gb164\|BE637379 | 369 | 61 | 80 | tblastn |
| 124 | LAB5_H9 | spruce\|gb162\|CO219921 | 370 | 61 | 83.1 | blastp |
| 125 | LAB5_H10 | sugarcane\|gb157.3\|BQ529602 | 371 | 61 | 93.3 | blastp |
| 126 | LAB5_H11 | sugarcane\|gb157.3\|BQ535202 | 372 | 61 | 89.23 | tblastn |
| 127 | LAB5_H12 | sugarcane\|gb157.3\|CA072503 | 373 | 61 | 94.8 | blastp |
| 128 | LAB5_H13 | sugarcane\|gb157.3\|CA082920 | 374 | 61 | 94.1 | blastp |
| 129 | LAB5_H14 | sugarcane\|gb157.3\|CA085102 | 375 | 61 | 89.1 | blastp |
| 130 | LAB5_H15 | sugarcane\|gb157.3\|CA090891 | 376 | 61 | 94.1 | blastp |
| 131 | LAB5_H16 | sugarcane\|gb157.3\|CA122790 | 377 | 61 | 90.5 | blastp |
| 132 | LAB5_H17 | switchgrass\|gb167\|DN145030 | 378 | 61 | 80.6 | blastp |
| 133 | LAB5_H18 | switchgrass\|gb167\|FE635988 | 379 | 61 | 89.3 | blastp |
| 134 | LAB5_H19 | switchgrass\|gb167\|FL774816 | 380 | 61 | 85.5 | tblastn |
| 135 | LAB5_H20 | wheat\|gb164\|AF181661 | 381 | 61 | 84.6 | blastp |
| 136 | LAB5_H21 | wheat\|gb164\|BE417364 | 382 | 61 | 83.1 | blastp |
| 137 | LAB5_H22 | wheat\|gb164\|BF484215 | 383 | 61 | 80.6 | blastp |
| 138 | LAB7_H0 | barley\|gb157.3\|AL501769 | 384 | 62 | 83 | blastp |
| 139 | LAB7_H1 | brachypodium\|gb169\|BE471170 | 385 | 62 | 82.8 | blastp |
| 140 | LAB7_H2 | maize\|gb170\|AW042403 | 386 | 62 | 80.4 | blastp |
| 141 | LAB7_H3 | maize\|gb170\|T69041 | 387 | 62 | 81.8 | blastp |
| 142 | LAB7_H4 | sorghum\|gb161.crp\|BE356561 | 388 | 62 | 82.3 | blastp |
| 143 | LAB7_H5 | sugarcane\|gb157.3\|CA091573 | 389 | 62 | 83.1 | blastp |
| 144 | LAB7_H6 | switchgrass\|gb167\|DN142661 | 390 | 62 | 81.4 | blastp |

TABLE 6-continued

Homologues of the identified genes of the invention which can increase ABST, fiber development (quality and yield), biomass, growth rate, nitrogen use efficiency, fertilizer use efficiency, water use efficiency, yield and/or oil content of a plant

| Polynucl. SEQ ID NO: | Gene Name | Organism/Cluster name | Polypep. SEQ ID NO: | Homology to SEQ ID NO: | % Global identity | Algor. |
|---|---|---|---|---|---|---|
| 145 | LAB7_H7 | switchgrass\|gb167\|FE615102 | 391 | 62 | 81.2 | blastp |
| 146 | LAB7_H8 | wheat\|gb164\|BE443254 | 392 | 62 | 84 | blastp |
| 147 | LAB7_H9 | wheat\|gb164\|BE471170 | 393 | 62 | 83.1 | blastp |
| 148 | LAB7_H10 | wheat\|gb164\|BF293813 | 394 | 62 | 82.6 | blastp |
| 149 | LAB8_H0 | rice\|gb170\|OS03G22790 | 395 | 63 | 98.85 | tblastn |
| 150 | LAB15_H0 | wheat\|gb164\|BM137033 | 396 | 68 | 87.63 | tblastn |
| 151 | LAB15_H1 | wheat\|gb164\|BM138703 | 397 | 68 | 83.51 | tblastn |
| 152 | LAB15_H2 | wheat\|gb164\|CD882022 | 398 | 68 | 81.5 | blastp |
| 153 | LAB2_H0 | brachypodium\|gb169\|DV485170 | 399 | 69 | 81.8 | blastp |
| 154 | LAB2_H1 | fescue\|gb161\|DT694419 | 400 | 69 | 83.2 | blastp |
| 155 | LAB16_H0 | antirrhinum\|gb166\|AJ787590 | 401 | 70 | 81.2 | blastp |
| 156 | LAB16_H1 | apple\|gb171\|CN580957 | 402 | 70 | 86.4 | blastp |
| 157 | LAB16_H2 | apricot\|gb157.2\|CB824020 | 403 | 70 | 85.1 | blastp |
| 158 | LAB16_H3 | arabidopsis\|gb165\|AT4G38580 | 404 | 70 | 83.7 | blastp |
| 159 | LAB16_H4 | b_juncea\|gb164\|EVGN00544315151807 | 405 | 70 | 83.7 | blastp |
| 160 | LAB16_H5 | b_oleracea\|gb161\|AM058105 | 406 | 70 | 82.4 | blastp |
| 161 | LAB16_H6 | b_oleracea\|gb161\|ES942384 | 407 | 70 | 81.7 | tblastn |
| 162 | LAB16_H7 | b_rapa\|gb162\|EX025293 | 408 | 70 | 83 | blastp |
| 163 | LAB16_H8 | barley\|gb157.3\|BF258224 | 409 | 70 | 84.97 | tblastn |
| 164 | LAB16_H9 | bean\|gb167\|CA910356 | 410 | 70 | 85.1 | blastp |
| 165 | LAB16_H10 | cacao\|gb167\|CU476614 | 411 | 70 | 95.5 | blastp |
| 166 | LAB16_H11 | canola\|gb161\|CD817401 | 412 | 70 | 83 | blastp |
| 167 | LAB16_H12 | canola\|gb161\|CN736951 | 413 | 70 | 81.7 | blastp |
| 168 | LAB16_H13 | cassava\|gb164\|BI325222 | 414 | 70 | 84.42 | tblastn |
| 169 | LAB16_H14 | castorbean\|09v1\|EG691829 | 415 | 70 | 87 | blastp |
| 170 | LAB16_H15 | catharanthus\|gb166\|FD421293 | 416 | 70 | 84.4 | blastp |
| 171 | LAB16_H16 | chestnut\|gb170\|SRR006295S0010879 | 417 | 70 | 81.3 | blastp |
| 172 | LAB16_H17 | chickpea\|09v1\|FE673275 | 418 | 70 | 81.4 | blastp |
| 173 | LAB16_H18 | cichorium\|gb171\|EH697988 | 419 | 70 | 80 | blastp |
| 174 | LAB16_H19 | citrus\|gb166\|CN184469 | 420 | 70 | 80.5 | blastp |
| 175 | LAB16_H20 | coffea\|gb157.2\|DV666808 | 421 | 70 | 80.6 | blastp |
| 176 | LAB16_H21 | cowpea\|gb166\|FC458156 | 422 | 70 | 83.1 | blastp |
| 177 | LAB16_H22 | cowpea\|gb166\|FF538669 | 423 | 70 | 80.8 | blastp |
| 178 | LAB16_H23 | grape\|gb160\|BM436505 | 424 | 70 | 86.5 | blastp |
| 179 | LAB16_H24 | ipomoea\|gb157.2\|BJ555808 | 425 | 70 | 82.6 | blastp |
| 180 | LAB16_H25 | kiwi\|gb166\|FG420453 | 426 | 70 | 81.8 | blastp |
| 181 | LAB16_H26 | liquorice\|gb171\|FS257949 | 427 | 70 | 80.5 | blastp |
| 182 | LAB16_H27 | lotus\|09v1\|GO007127 | 428 | 70 | 84.6 | blastp |
| 183 | LAB16_H28 | medicago\|09v1\|BE320877 | 429 | 70 | 81.4 | blastp |
| 184 | LAB16_H29 | melon\|gb165\|AM726967 | 430 | 70 | 83.1 | blastp |
| 185 | LAB16_H30 | papaya\|gb165\|EX255354 | 431 | 70 | 86.5 | blastp |
| 186 | LAB16_H31 | peach\|gb157.2\|BU039481 | 432 | 70 | 86.4 | blastp |
| 187 | LAB16_H32 | peanut\|gb171\|CX018165 | 433 | 70 | 82.2 | blastp |
| 188 | LAB16_H33 | peanut\|gb171\|ES491048 | 434 | 70 | 82.8 | blastp |
| 189 | LAB16_H34 | pepper\|gb171\|BM060814 | 435 | 70 | 81.8 | blastp |
| 190 | LAB16_H35 | periwinkle\|gb164\|FD421293 | 436 | 70 | 84.4 | blastp |
| 191 | LAB16_H36 | poplar\|gb170\|AJ534494 | 437 | 70 | 85.1 | blastp |
| 192 | LAB16_H37 | poplar\|gb170\|BI129301 | 438 | 70 | 83.8 | blastp |
| 193 | LAB16_H38 | potato\|gb157.2\|BG098018 | 439 | 70 | 82.5 | blastp |
| 194 | LAB16_H39 | potato\|gb157.2\|BG098308 | 440 | 70 | 82.5 | blastp |
| 195 | LAB16_H40 | prunus\|gb167\|BU039481 | 441 | 70 | 86.4 | blastp |
| 196 | LAB16_H41 | radish\|gb164\|EV544328 | 442 | 70 | 83.7 | blastp |
| 197 | LAB16_H42 | soybean\|gb168\|BE315834 | 443 | 70 | 85.1 | blastp |
| 198 | LAB16_H43 | spurge\|gb161\|DV122649 | 444 | 70 | 85.71 | tblastn |
| 199 | LAB16_H44 | strawberry\|gb164\|CO817272 | 445 | 70 | 83.8 | blastp |
| 200 | LAB16_H45 | tomato\|gb164\|AA824901 | 446 | 70 | 81.8 | blastp |
| 201 | LAB16_H46 | triphysaria\|gb164\|EX989778 | 447 | 70 | 81.8 | blastp |
| 202 | LAB16_H47 | walnuts\|gb166\|CB303653 | 448 | 70 | 80.5 | blastp |
| 203 | LAB17_H0 | barley\|gb157.3\|BE231003 | 449 | 71 | 91 | blastp |
| 204 | LAB17_H1 | brachypodium\|gb169\|BE498333 | 450 | 71 | 91 | blastp |
| 205 | LAB17_H2 | cenchrus\|gb166\|EB657534 | 451 | 71 | 84.5 | blastp |
| 206 | LAB17_H3 | fescue\|gb161\|DT685866 | 452 | 71 | 91.6 | blastp |
| 207 | LAB17_H4 | leymus\|gb166\|EG394438 | 453 | 71 | 90.3 | blastp |
| 208 | LAB17_H5 | maize\|gb170\|AW498181 | 454 | 71 | 94.2 | blastp |
| 209 | LAB17_H6 | pseudoroegneria\|gb167\|FF340520 | 455 | 71 | 90.3 | blastp |
| 210 | LAB17_H7 | rice\|gb170\|OS04G17100 | 456 | 71 | 93.5 | blastp |
| 211 | LAB17_H8 | sugarcane\|gb157.3\|CA073067 | 457 | 71 | 85.16 | tblastn |
| 212 | LAB17_H9 | sugarcane\|gb157.3\|CA075729 | 458 | 71 | 96.8 | blastp |
| 213 | LAB17_H10 | sugarcane\|gb157.3\|CA078804 | 459 | 71 | 96.8 | blastp |
| 214 | LAB17_H11 | sugarcane\|gb157.3\|CA116673 | 460 | 71 | 96.1 | blastp |
| 215 | LAB17_H12 | sugarcane\|gb157.3\|CA118688 | 461 | 71 | 97.4 | blastp |
| 216 | LAB17_H13 | sugarcane\|gb157.3\|CA119291 | 462 | 71 | 96.1 | blastp |
| 217 | LAB17_H14 | sugarcane\|gb157.3\|CA222723 | 463 | 71 | 94.2 | blastp |

TABLE 6-continued

Homologues of the identified genes of the invention which can increase ABST, fiber
development (quality and yield), biomass, growth rate, nitrogen use efficiency, fertilizer
use efficiency, water use efficiency, yield and/or oil content of a plant

| Polynucl. SEQ ID NO: | Gene Name | Organism/Cluster name | Polypep. SEQ ID NO: | Homology to SEQ ID NO: | % Global identity | Algor. |
|---|---|---|---|---|---|---|
| 218 | LAB17_H15 | switchgrass\|gb167\|DN143094 | 464 | 71 | 85.9 | blastp |
| 219 | LAB17_H16 | switchgrass\|gb167\|FL792168 | 465 | 71 | 80.8 | blastp |
| 220 | LAB17_H17 | wheat\|gb164\|BE498333 | 466 | 71 | 90.3 | blastp |
| 221 | LAB17_H18 | wheat\|gb164\|BF474623 | 467 | 71 | 89.7 | blastp |
| 222 | LAB17_H19 | wheat\|gb164\|CV760043 | 468 | 71 | 89.7 | blastp |
| 223 | LAB18_H0 | switchgrass\|gb167\|DN140747 | 469 | 72 | 80.6 | blastp |
| 224 | LAB20_H0 | sugarcane\|gb157.3\|CA130714 | 470 | 73 | 82.6 | blastp |
| 225 | LAB21_H0 | aquilegia\|gb157.3\|DR914842 | 471 | 74 | 82.9 | blastp |
| 226 | LAB21_H1 | arabidopsis\|gb165\|AT3G47340 | 472 | 74 | 80.6 | blastp |
| 227 | LAB21_H2 | b_oleracea\|gb161\|X84448 | 473 | 74 | 80.4 | blastp |
| 228 | LAB21_H3 | b_rapa\|gb162\|CV545962 | 474 | 74 | 80.3 | blastp |
| 229 | LAB21_H4 | barley\|gb157.3\|BI948886 | 475 | 74 | 87.5 | blastp |
| 230 | LAB21_H5 | bean\|gb167\|AJ133522 | 476 | 74 | 81.9 | blastp |
| 231 | LAB21_H6 | bean\|gb167\|CB542570 | 477 | 74 | 83.1 | blastp |
| 232 | LAB21_H7 | cacao\|gb167\|CA797951 | 478 | 74 | 83.5 | blastp |
| 233 | LAB21_H8 | castorbean\|09v1\|EE256522 | 479 | 74 | 82.1 | blastp |
| 234 | LAB21_H9 | centaurea\|gb166\|EL931554 | 480 | 74 | 81.2 | blastp |
| 235 | LAB21_H10 | citrus\|gb166\|BQ623162 | 481 | 74 | 83 | blastp |
| 236 | LAB21_H11 | cotton\|gb164\|AI054642 | 482 | 74 | 83.1 | blastp |
| 237 | LAB21_H12 | cotton\|gb164\|BF277939 | 483 | 74 | 81.8 | blastp |
| 238 | LAB21_H13 | cotton\|gb164\|CD486005 | 484 | 74 | 84 | blastp |
| 239 | LAB21_H14 | cowpea\|gb166\|FC458174 | 485 | 74 | 83.3 | blastp |
| 240 | LAB21_H15 | cowpea\|gb166\|FC461749 | 486 | 74 | 82.8 | blastp |
| 241 | LAB21_H16 | kiwi\|gb166\|FG404880 | 487 | 74 | 81.8 | blastp |
| 242 | LAB21_H17 | lettuce\|gb157.2\|DW062326 | 488 | 74 | 83.1 | blastp |
| 243 | LAB21_H18 | maize\|gb170\|AW076472 | 489 | 74 | 85.1 | blastp |
| 244 | LAB21_H19 | medicago\|09v1\|AW126175 | 490 | 74 | 80.7 | blastp |
| 245 | LAB21_H20 | monkeyflower\|09v1\|GO982561 | 491 | 74 | 81.4 | blastp |
| 246 | LAB21_H21 | oak\|gb170\|CU656355 | 492 | 74 | 82.8 | blastp |
| 247 | LAB21_H22 | oil_palm\|gb166\|EL681380 | 493 | 74 | 87 | blastp |
| 248 | LAB21_H23 | peach\|gb157.2\|BU043116 | 494 | 74 | 82 | blastp |
| 249 | LAB21_H24 | poplar\|gb170\|BI138803 | 495 | 74 | 82.8 | blastp |
| 250 | LAB21_H25 | poplar\|gb170\|BU814657 | 496 | 74 | 83.6 | blastp |
| 251 | LAB21_H26 | potato\|gb157.2\|CK258159 | 497 | 74 | 82.1 | blastp |
| 252 | LAB21_H27 | prunus\|gb167\|BU043116 | 498 | 74 | 82.7 | blastp |
| 253 | LAB21_H28 | pseudoroegneria\|gb167\|FF342746 | 499 | 74 | 98.3 | blastp |
| 254 | LAB21_H29 | radish\|gb164\|AB050900 | 500 | 74 | 80.6 | blastp |
| 255 | LAB21_H30 | sorghum\|gb161.crp\|AW286475 | 501 | 74 | 84.96 | tblastn |
| 256 | LAB21_H31 | soybean\|gb168\|AW126284 | 502 | 74 | 83.1 | blastp |
| 257 | LAB21_H32 | soybean\|gb168\|AW720554 | 503 | 74 | 82.3 | blastp |
| 258 | LAB21_H33 | soybean\|gb168\|GMU55874 | 504 | 74 | 81.48 | tblastn |
| 259 | LAB21_H34 | soybean\|gb168\|GMU77678 | 505 | 74 | 83.5 | blastp |
| 260 | LAB21_H35 | soybean\|gb168\|GMU77679 | 506 | 74 | 83 | blastp |
| 261 | LAB21_H36 | sugarcane\|gb157.3\|BQ535363 | 507 | 74 | 85.5 | blastp |
| 262 | LAB21_H37 | sugarcane\|gb157.3\|BQ535939 | 508 | 74 | 85.5 | blastp |
| 263 | LAB21_H38 | sunflower\|gb162\|AF037363 | 509 | 74 | 81.3 | blastp |
| 264 | LAB21_H39 | sunflower\|gb162\|AF190728 | 510 | 74 | 80.9 | blastp |
| 265 | LAB21_H40 | sunflower\|gb162\|DY931765 | 511 | 74 | 80.7 | blastp |
| 266 | LAB21_H41 | tomato\|gb164\|BG127495 | 512 | 74 | 82.5 | blastp |
| 267 | LAB21_H42 | triphysaria\|gb164\|AF014055 | 513 | 74 | 81.9 | blastp |
| 268 | LAB21_H43 | wheat\|gb164\|BE403264 | 514 | 74 | 98.6 | blastp |
| 269 | LAB21_H44 | wheat\|gb164\|BE403866 | 515 | 74 | 98.6 | blastp |
| 270 | LAB21_H45 | wheat\|gb164\|BE430398 | 516 | 74 | 87.9 | blastp |
| 271 | LAB22_H0 | maize\|gb170\|BG833173 | 517 | 75 | 81.7 | blastp |
| 272 | LAB22_H1 | maize\|gb170\|BI423707 | 518 | 75 | 86.4 | blastp |
| 273 | LAB22_H2 | sugarcane\|gb157.3\|BQ536240 | 519 | 75 | 90.9 | blastp |
| 274 | LAB22_H3 | sugarcane\|gb157.3\|BQ536340 | 520 | 75 | 91 | blastp |
| 275 | LAB22_H4 | sugarcane\|gb157.3\|BU103170 | 521 | 75 | 88.2 | blastp |
| 276 | LAB22_H5 | sugarcane\|gb157.3\|CA116439 | 522 | 75 | 89.4 | blastp |
| 277 | LAB22_H6 | switchgrass\|gb167\|FL733549 | 523 | 75 | 85.9 | blastp |
| 278 | LAB22_H7 | wheat\|gb164\|CA484841 | 524 | 75 | 100 | blastp |
| 279 | LAB3_H0 | arabidopsis\|gb165\|AT1G15380 | 525 | 76 | 89.1 | blastp |
| 280 | LAB3_H1 | b_rapa\|gb162\|EX016736 | 526 | 76 | 98.9 | blastp |
| 281 | LAB3_H2 | canola\|gb161\|CD830331 | 527 | 76 | 81.6 | blastp |
| 282 | LAB3_H3 | canola\|gb161\|CN731229 | 528 | 76 | 81.6 | blastp |
| 283 | LAB3_H4 | radish\|gb164\|EV527368 | 529 | 76 | 94.3 | blastp |
| 284 | LAB3_H5 | radish\|gb164\|EV547102 | 530 | 76 | 81 | blastp |
| 285 | LAB23_H0 | pseudoroegneria\|gb167\|FF341473 | 531 | 77 | 89.9 | blastp |
| 286 | LAB23_H1 | wheat\|gb164\|BE516915 | 532 | 77 | 87.6 | blastp |
| 287 | LAB23_H2 | wheat\|gb164\|BE517204 | 533 | 77 | 88.48 | tblastn |
| 288 | LAB24_H0 | maize\|gb170\|BE552559 | 534 | 78 | 80.4 | blastp |
| 289 | LAB24_H1 | sugarcane\|gb157.3\|CA087195 | 535 | 78 | 86.1 | blastp |
| 290 | LAB24_H2 | switchgrass\|gb167\|FL736257 | 536 | 78 | 80 | blastp |

TABLE 6-continued

Homologues of the identified genes of the invention which can increase ABST, fiber development (quality and yield), biomass, growth rate, nitrogen use efficiency, fertilizer use efficiency, water use efficiency, yield and/or oil content of a plant

| Polynucl. SEQ ID NO: | Gene Name | Organism/Cluster name | Polypep. SEQ ID NO: | Homology to SEQ ID NO: | % Global identity | Algor. |
|---|---|---|---|---|---|---|
| 291 | LAB25_H0 | leymus\|gb166\|EG374989 | 537 | 79 | 85.6 | blastp |
| 292 | LAB25_H1 | leymus\|gb166\|EG375019 | 538 | 79 | 91.3 | blastp |
| 293 | LAB25_H2 | pseudoroegneria\|gb167\|FF339936 | 539 | 79 | 90.3 | blastp |
| 294 | LAB25_H3 | rye\|gb164\|BE493752 | 540 | 79 | 84.2 | blastp |
| 295 | LAB25_H4 | wheat\|gb164\|TAU73210 | 541 | 79 | 89.2 | blastp |
| 296 | LAB25_H5 | wheat\|gb164\|TAU73211 | 542 | 79 | 91.5 | blastp |
| 297 | LAB25_H6 | wheat\|gb164\|WHTWCOR | 543 | 79 | 90.1 | blastp |
| 298 | LAB31_H0 | b_oleracea\|gb161\|AM387244 | 544 | 81 | 94.6 | blastp |
| 299 | LAB31_H1 | b_rapa\|gb162\|AT000569 | 545 | 81 | 97.9 | blastp |
| 300 | LAB31_H2 | canola\|gb161\|DY012596 | 546 | 81 | 95.2 | blastp |
| 301 | LAB31_H3 | radish\|gb164\|EV537620 | 547 | 81 | 87.1 | blastp |
| 302 | LAB32_H0 | pseudoroegneria\|gb167\|FF342820 | 548 | 82 | 89.1 | blastp |
| 303 | LAB33_H0 | sugarcane\|gb157.3\|BQ530200 | 549 | 83 | 88.1 | blastp |
| 304 | LAB34_H0 | bean\|gb167\|BQ481761 | 550 | 84 | 86.1 | blastp |
| 305 | LAB34_H1 | soybean\|gb168\|AI755294 | 551 | 84 | 90.9 | blastp |
| 306 | LAB35_H0 | barley\|gb157.3\|Y07823 | 552 | 85 | 92.4 | blastp |
| 307 | LAB35_H1 | brachypodium\|gb169\|Y07823 | 553 | 85 | 83.96 | tblastn |
| 308 | LAB36_H0 | maize\|gb170\|DW878104 | 554 | 86 | 88.3 | blastp |
| 309 | LAB38_H0 | barley\|gb157.3\|AL450676 | 555 | 87 | 91 | blastp |
| 310 | LAB38_H1 | barley\|gb157.3\|BE438884 | 556 | 87 | 91.4 | blastp |
| 311 | LAB38_H2 | barley\|gb157.3\|BF625343 | 557 | 87 | 84.9 | blastp |
| 312 | LAB38_H3 | barley\|gb157.3\|BG299345 | 558 | 87 | 86.12 | tblastn |
| 313 | LAB38_H4 | leymus\|gb166\|CD808961 | 559 | 87 | 94.3 | blastp |
| 314 | LAB38_H5 | pseudoroegneria\|gb167\|FF340156 | 560 | 87 | 95.9 | blastp |
| 315 | LAB38_H6 | wheat\|gb164\|AF495872 | 561 | 87 | 97.1 | blastp |
| 316 | LAB38_H7 | wheat\|gb164\|BE591570 | 562 | 87 | 98.4 | blastp |
| 317 | LAB39_H0 | switchgrass\|gb167\|FE640133 | 563 | 88 | 84.2 | blastp |
| 318 | LAB39_H1 | switchgrass\|gb167\|FL746283 | 564 | 88 | 84.6 | blastp |
| 319 | LAB39_H2 | wheat\|gb164\|CA484141 | 565 | 88 | 99.2 | blastp |
| 320 | LAB40_H0 | barley\|gb157.3\|BF258976 | 566 | 89 | 96.9 | blastp |
| 321 | LAB40_H1 | brachypodium\|gb169\|BE488436 | 567 | 89 | 84.4 | blastp |
| 322 | LAB41_H0 | barley\|gb157.3\|BE437787 | 568 | 90 | 90.5 | blastp |
| 323 | LAB43_H0 | leymus\|gb166\|EG377283 | 569 | 91 | 92.5 | blastp |
| 324 | LAB43_H1 | wheat\|gb164\|AL822945 | 570 | 91 | 91.7 | blastp |
| 325 | LAB43_H2 | wheat\|gb164\|BE413988 | 571 | 91 | 93.2 | blastp |
| 326 | LAB43_H3 | wheat\|gb164\|CA610190 | 572 | 91 | 92.8 | blastp |
| 327 | LAB45_H0 | apple\|gb171\|CN488819 | 573 | 92 | 80 | blastp |
| 328 | LAB45_H1 | barley\|gb157.3\|AL502429 | 574 | 92 | 88.8 | blastp |
| 329 | LAB45_H2 | basilicum\|gb157.3\|DY328093 | 575 | 92 | 80.7 | blastp |
| 330 | LAB45_H3 | brachypodium\|gb169\|BE403542 | 576 | 92 | 90.3 | blastp |
| 331 | LAB45_H4 | cotton\|gb164\|AI727046 | 577 | 92 | 80.42 | tblastn |
| 332 | LAB45_H5 | fescue\|gb161\|DT697400 | 578 | 92 | 83.1 | blastp |
| 333 | LAB45_H6 | leymus\|gb166\|EG380210 | 579 | 92 | 87.9 | blastp |
| 334 | LAB45_H7 | maize\|gb170\|LLAI855293 | 580 | 92 | 96.4 | blastp |
| 335 | LAB45_H8 | medicago\|09v1\|AW690268 | 581 | 92 | 80.76 | tblastn |
| 336 | LAB45_H9 | poplar\|gb170\|BI124748 | 582 | 92 | 80.5 | blastp |
| 337 | LAB45_H10 | potato\|gb157.2\|BF053337 | 583 | 92 | 80 | tblastn |
| 338 | LAB45_H11 | rice\|gb170\|OS02G50350 | 584 | 92 | 92.4 | blastp |
| 339 | LAB45_H12 | switchgrass\|gb167\|FL865538 | 585 | 92 | 96.2 | blastp |
| 340 | LAB45_H13 | tomato\|gb164\|BG126074 | 586 | 92 | 80.19 | tblastn |
| 341 | LAB45_H14 | wheat\|gb164\|BE403542 | 587 | 92 | 88.8 | blastp |
| 342 | LAB51_H0 | barley\|gb157.3\|BE421767 | 588 | 95 | 85.2 | blastp |
| 343 | LAB51_H1 | wheat\|gb164\|CA615952 | 589 | 95 | 93.1 | blastp |
| 344 | BDL103_H0 | barley\|gb157.3\|BI954496 | 590 | 96 | 82.75 | tblastn |
| 345 | BDL103_H1 | barley\|gb157.3\|BI956043 | 591 | 96 | 83.53 | tblastn |
| 346 | BDL103_H2 | brachypodium\|gb169\|BE497565 | 592 | 96 | 85.1 | blastp |
| 347 | BDL103_H3 | leymus\|gb166\|EG378510 | 593 | 96 | 84.6 | blastp |
| 348 | BDL103_H4 | pseudoroegneria\|gb167\|FF346555 | 594 | 96 | 81.89 | tblastn |
| 349 | BDL103_H5 | wheat\|gb164\|BE497565 | 595 | 96 | 82.68 | tblastn |
| 350 | BDL103_H6 | wheat\|gb164\|BF428885 | 596 | 96 | 83.14 | tblastn |
| 351 | BDL166_H0 | b_rapa\|gb162\|CX267860 | 597 | 100 | 81.77 | tblastn |
| 352 | BDL166_H1 | canola\|gb161\|CD820129 | 598 | 100 | 90.4 | blastp |
| 353 | CTF113_H0 | castorbean\|09v1\|XM002524611 | 599 | 103 | 81 | blastp |
| 354 | CTF113_H1 | poplar\|gb170\|BI124993 | 600 | 103 | 80.6 | blastp |
| 355 | CTF113_H2 | poplar\|gb170\|CV228068 | 601 | 103 | 81.1 | blastp |
| 356 | CTF180_H0 | castorbean\|09v1\|EG657203 | 602 | 106 | 80.7 | blastp |
| 357 | CTF215_H0 | castorbean\|09v1\|XM002514996 | 603 | 108 | 81.2 | blastp |
| 358 | CTF215_H1 | poplar\|gb170\|AI162434 | 604 | 108 | 82.3 | blastp |

Table 6: Provided are polynucleotides and polypeptides which are homologous to the identified polynucleotides or polypeptides of Table 5. Homol. = homologue; Algor. = Algorithm; Polynucl. = polynucleotide; Polypep. = polypeptide. Homology was calculated as % of identity over the aligned sequences. The query sequences were polynucleotide sequences SEQ ID NOs: 1-59 and 638) or polypeptides sequences SEQ ID NOs: 60-112, and the subject sequences are protein sequences identified in the database based on greater than 80% identity to the predicted translated sequences of the query nucleotide sequences.

Example 3

Gene Cloning and Generation of Binary Vectors for Plant Expression

To validate their role in improving ABST, yield, growth rate, vigor, biomass, nitrogen use efficiency and/or oil content selected genes were over-expressed in plants, as follows.

Cloning Strategy

Genes listed in Examples 1 and 2 hereinabove were cloned into binary vectors for the generation of transgenic plants. For cloning, the full-length open reading frames (ORFs) were identified. EST clusters and in some cases mRNA sequences were analyzed to identify the entire open reading frame by comparing the results of several translation algorithms to known proteins from other plant species.

In order to clone the full-length cDNAs, reverse transcription (RT) followed by polymerase chain reaction (PCR; RT-PCR) was performed on total RNA extracted from leaves, roots or other plant tissues, growing under normal conditions. Total RNA extraction, production of cDNA and PCR amplification was performed using standard protocols described elsewhere (Sambrook J., E. F. Fritsch, and T. Maniatis. 1989. Molecular Cloning. A Laboratory Manual, 2nd Ed. Cold Spring Harbor Laboratory Press, New York) which are well known to those skilled in the art. PCR products were purified using PCR purification kit (Qiagen)

Usually, 2 sets of primers were prepared for the amplification of each gene, via nested PCR (meaning first amplifying the gene using external primers and then using the produced PCR product as a template for a second PCR reaction, where the internal set of primers are used). Alternatively, one or two of the internal primers were used for gene amplification, both in the first and the second PCR reactions (meaning only 2-3 primers were designed for a gene). To facilitate further cloning of the cDNAs, an 8-12 bp extension was added to the 5' of each internal primer. The primer extension includes an endonuclease restriction site. The restriction sites were selected using two parameters: (a) the restriction site does not exist in the cDNA sequence; and (b) the restriction sites in the forward and reverse primers are designed such that the digested cDNA is inserted in the sense direction into the binary vector utilized for transformation. In Table 7 below, primers used for cloning selected genes are provided.

TABLE 7

Provided are primers and the restriction sites and enzymes used for cloning selected genes (polynucleotides, provided by gene name) identified herein.
PCR primers for cloning selected genes of the invention

| Gene Name | Restriction Enzymes used for cloning | Primers used for amplification (SEQ ID NOs:) |
| --- | --- | --- |
| BDL103S | SalI, Xba I | BDL103_Short_F_SalI SEQ ID NO: 677<br>AATGTCGACTCTGGGCTCAGGGATAGG<br>BDL103_NR_XbaI SEQ ID NO: 678<br>TATCTAGACTACTAAAAGGAATTATCTAGCAGAGG |
| BDL12 | SalI, SacI | BDL12_gDNA_NF_SalI SEQ ID NO: 679<br>AATGTCGACGTTCTATCCCCAACTCTAAATG<br>BDL12_gDNA_NR_SacI SEQ ID NO: 680<br>AGAGCTCCTTAAAGTTCTATCGAGATAGTGC |
| BDL14 | SalI, Xba I | BDL14_ORF_F1_SalI SEQ ID NO: 681<br>AATGTCGACAACAATGGATCTACAACAGTCCGAAAC<br>BDL14_ORF_F1_SalI SEQ ID NO: 681<br>AATGTCGACAACAATGGATCTACAACAGTCCGAAAC<br>BDL14_ORF_NR_XbaI SEQ ID NO: 682<br>AATCTAGACACTCAGACAGCTGGGTATTAAAC<br>BDL14_ORF_ER_SacI SEQ ID NO: 683<br>AGAGCTCGTTGTGGCACTCAGACAGCTG |
| BDL166 | XbaI, SacI | BDL166_NF_XbaI SEQ ID NO: 684<br>AATCTAGAAAAGTTACACCTTACTAAACACAAAC<br>BDL166_NR_SacI SEQ ID NO: 685<br>TGAGCTCTCTTGTTGATAGTCTTCATAATCG |
| BDL210 | SalI, XbaI | BDL210_NF_SalI SEQ ID NO: 686<br>AAAGTCGACAACAAAGTTATGGGTTTCTCG<br>BDL210_EF_SalI SEQ ID NO: 687<br>AAAGTCGACGAGCAACAAAGTTATGGGTTTC<br>BDL210_NR_XbaI SEQ ID NO: 688<br>ATTCTAGATTAGGATGATCAGGAGATGAGAGAG<br>BDL210_ER_XbaI SEQ ID NO: 689<br>ATTCTAGACTAAAGTAGAGAGATGGATGATCAGG |
| CTF113 | | CTF113_ORF_F_Sm SEQ ID NO: 690<br>GACCCGGGAAACGATGGAGGATCTTGCC<br>CTF113_ORF_R_Sc SEQ ID NO: 691<br>CAGAGCTCTTGGAATTGAAATGTCATTACAGAG |
| CTF163 | SalI, XbaI | CTF163_NF_SalI SEQ ID NO: 692<br>AAAGTCGACGAACTGGTTGTTCTTGGCTATG<br>CTF163_NR_XbaI SEQ ID NO: 693<br>ATTCTAGACCAGATGAACTTGGCTTTATC |

TABLE 7-continued

Provided are primers and the restriction sites and enzymes used for cloning selected genes (polynucleotides, provided by gene name) identified herein.
PCR primers for cloning selected genes of the invention

| Gene Name | Restriction Enzymes used for cloning | Primers used for amplification (SEQ ID NOs:) |
|---|---|---|
| CTF175 | EcoRV, Sac I | CTF175_ORF_NF_EcRV SEQ ID NO: 694<br>AGGATATCTTTCGATCACCGTGATGGC<br>CTF175_ORF_EF_EcRV SEQ ID NO: 695<br>AAGATATCAGAGCATTTCGATCACCGTG<br>CTF175_ORF_NR_Sc SEQ ID NO: 696<br>GCGAGCTCGTAGTGACGTCACCGGTTC<br>CTF175_ORF_ER_Sc SEQ ID NO: 697<br>TCGAGCTCCTCACCTTTCACTATCACCC |
| CTF180 | SalI, SacI | CTF180_NF_SalI SEQ ID NO: 698<br>AAAGTCGACTTCGATGTGGGATAACTGAATC<br>CTF180_ER_SacI SEQ ID NO: 699<br>AACGAGCTCATTCAACAACCTAACCATCTTTG<br>CTF180_NR_SacI SEQ ID NO: 700<br>AATGAGCTCTTTTCTTTACAGTGGAATCTGC<br>CTF180_ER_SacI SEQ ID NO: 699<br>AACGAGCTCATTCAACAACCTAACCATCTTTG |
| CTF205 | | CTF205_EF_SalI SEQ ID NO: 701<br>AAAGTCGACGAAAACACAGATGGAAGATATTAAAC<br>CTF205_ER_XbaI SEQ ID NO: 702<br>ATTCTAGATGGACTTACAGGTCAAGAAGGTAG |
| CTF215 | SalI, XbaI | CTF215_NF_SalI SEQ ID NO: 703<br>AAAGTCGACAAGTTTGGAAAGAGATGAATCC<br>CTF215_NR_XbaI SEQ ID NO: 704<br>ATTCTAGACTAAGCAAGCAGAAACAAAATATAGC |
| CTF226 | SalI, XbaI | CTF226_NF_SalI SEQ ID NO: 705<br>AAAGTCGACGCCAAGGTCAAACGAAGG<br>CTF226_EF_SalI SEQ ID NO: 706<br>AAAGTCGACCAAAAGCCAAGGTCAAACG<br>CTF226_NR_XbaI SEQ ID NO: 707<br>ATTCTAGACTAAACTTATGCAACATGAGCTGG<br>CTF226_ER_XbaI SEQ ID NO: 708<br>ACTCTAGAAAGTCATTATCCTAGTTCAGTTTGC |
| LAB11 | SalI, XbaI | LAB11_NF_SalI SEQ ID NO: 709<br>AAAGTCGACATCTACTGCCTTTGACCGATG<br>LAB11_NR_XbaI SEQ ID NO: 710<br>AATTCTAGATTACAGTTAAGTGAGGACATTCTTGG |
| LAB13 | SalI, XbaI | LAB13_NF_SalI SEQ ID NO: 711<br>AAAGTCGACCCCAAGATCGATATAAATTTCC<br>LAB13_NR_XbaI SEQ ID NO: 712<br>AACTCTAGAAACCACCATGCTTGCTCATC |
| LAB14 | EcoRV, EcoRV | LAB14_NF_EcoRV SEQ ID NO: 713<br>AATGATATCTTCCATTGTTACACGCGTTC<br>LAB14_NR_EcoRV SEQ ID NO: 714<br>AATGATATCTTAGGTGATTTAAAGCCAGAGGG |
| LAB16 | SalI, XbaI | LAB16_NF_SalI SEQ ID NO: 715<br>AAAGTCGACAACCAGACAAGAGAGAAAACAAG<br>LAB16_NR_XbaI SEQ ID NO: 716<br>AATTCTAGATTACAATCACATAACAGAACAAGCAG |
| LAB17 | EcoRV, PstI | LAB17_NF_EcoRV SEQ ID NO: 717<br>AATGATATCTTGTTTCGTTTTCCCTTAGC<br>LAB17_NR_PstI SEQ ID NO: 718<br>AATCTGCAGTCACCAGTTCACCACCATCTAC |
| LAB2 | EcoRV, PstI | LAB2_NF_EcoRV SEQ ID NO: 719<br>AATGATATCTTGCCGGTCGATCTTGAG<br>LAB2_EF_EcoRV SEQ ID NO: 720<br>AATGATATCCCTATATCTCCCTCCTCCTCC |
| LAB2 | | LAB2_NR_PstI SEQ ID NO: 721<br>AATCTGCAGTCAGCCACGGACTACCTACATGAC<br>LAB2_ER_PstI SEQ ID NO: 722<br>AACCTGCAGACAATTTCATTCTGTGGGTTC |

TABLE 7-continued

Provided are primers and the restriction sites and enzymes used for cloning selected genes (polynucleotides, provided by gene name) identified herein.
PCR primers for cloning selected genes of the invention

| Gene Name | Restriction Enzymes used for cloning | Primers used for amplification (SEQ ID NOs:) |
|---|---|---|
| LAB20 | SmaI | LAB20_NF SEQ ID NO: 723<br>CCTCAGAAAATCACCGTACG<br>LAB20_NR_SmaI SEQ ID NO: 724<br>TAACCCGGGCCTATGAACAGATATCTGACATGATC |
| LAB21 | SalI, XbaI | LAB21_NF_SalI SEQ ID NO: 725<br>TTAGTCGACGGAGAGAGATCTTCTAGCTACATAC<br>LAB21_NR_XbaI SEQ ID NO: 726<br>TAATCTAGATCACAGGACAGGACACCATCAAC |
| LAB22 | SalI, XbaI | LAB22_NF_SalI SEQ ID NO: 727<br>TTAGTCGACGGAGACAAAGATGGAGAACAAC<br>LAB22_NR_XbaI SEQ ID NO: 728<br>TATTCTAGACCGAAATTAAACAACAAGTACAC |
| LAB23 | EcoRV, EcoRV | LAB23_NF_EcoRV SEQ ID NO: 729<br>AAAGATATCGGAGGTACATATAGCTAGCGAAG<br>LAB23_NR_EcoRV SEQ ID NO: 730<br>AATGATATCCTAACAAAATCCACGACTCCACTG |
| LAB24 | SalI, XbaI | LAB24_NF_SalI SEQ ID NO: 731<br>AAAGTCGACGAGAGAGGATGGTGAGCAGC<br>LAB24_NR_XbaI SEQ ID NO: 732<br>AATTCTAGATTACGTGTAGTCATCAAATCACGC |
| LAB25 | SalI, XbaI | LAB25_NF_SalI SEQ ID NO: 733<br>AATGTCGACTCTAGCTCCCACGAGTCTTTAG<br>LAB25_NR_XbaI SEQ ID NO: 734<br>AATTCTAGATTACAACAATTTAATGGAGGTCCG |
| LAB3 | SalI, XbaI | LAB3_NF_SalI SEQ ID NO: 735<br>TTAGTCGACGAGCAAAAAATGAAGGAGAAC<br>LAB3_NR_XbaI SEQ ID NO: 736<br>TATTCTAGATTACAGAGATTGTTAAGGTTGGACC |
| LAB31 | EcoRV, PstI | LAB31 NF EcoRV SEQ ID NO: 737<br>AAAGATATCTCACAATTTCATTCACAAGTCG<br>LAB31 NR PstI SEQ ID NO: 738<br>AATCTGCAGTTTTCAAATCCAAACCCAAC |
| LAB32 | SalI, XbaI | LAB32_NE_SalI SEQ ID NO: 739<br>AAAGTCGACCTTTCCTTTCCTTTCCATCC<br>LAB32_EF_SalI SEQ ID NO: 740<br>AATTCTAGAAGCCATCACCACGCATTAC<br>LAB32_NR_XbaI SEQ ID NO: 741<br>AATTCTAGAAGCACTGAGCAGCCTTCATC<br>LAB32_ER_XbaI SEQ ID NO: 740<br>AATTCTAGAAGCCATCACCACGCATTAC |
| LAB33 | EcoRV, EcoRV | LAB33 NF EcoRV SEQ ID NO: 742<br>TCAGATATCCATCGCATCGCATCCATC<br>LAB33 NR EcoRV SEQ ID NO: 743<br>ATAGATATCGCTGCCTGCTTCTGATCTG |
| LAB34 | SalI, XbaI | LAB34_NF_SalI SEQ ID NO: 744<br>AAAGTCGACGCTAGTGAGATACCATGGACAAC<br>LAB34_NR_XbaI SEQ ID NO: 745<br>AAATCTAGATTACTTCTATGCTGGAATGACTTTG |
| LAB35 |  | LAB35_NF_SalI SEQ ID NO: 746<br>AAAGTCGACCAGATCGCGATGAAGTCTTG<br>LAB35_EF_SalI SEQ ID NO: 747<br>AAAGTCGACAGGGGAGAAGAGAGAGACAG<br>LAB35_NR_XbaI SEQ ID NO: 748<br>AAATCTAGATTAGCTCGTTCATTTAGCCTCAG<br>LAB35 ER Xba SEQ ID NO: 749<br>TCCTCTAGAGAGTTTATTCCTCGACGATGC |

TABLE 7-continued

Provided are primers and the restriction sites and enzymes used for cloning selected genes (polynucleotides, provided by gene name) identified herein.
PCR primers for cloning selected genes of the invention

| Gene Name | Restriction Enzymes used for cloning | Primers used for amplification (SEQ ID NOs:) |
|---|---|---|
| LAB36 | | LAB36_NF_SalI SEQ ID NO: 750 AAAGTCGACCAGTGTAGAGCAAGAGGTGTGG LAB36_EF_SalI SEQ ID NO: 751 AAAGTCGACTCGTCTCGATCAGTGTAGAGC LAB36_NR_XbaI SEQ ID NO: 752 AAATCTAGATTACGTCGTTCATTTAGCCTTTG LAB36_ER_XbaI SEQ ID NO: 753 AATTCTAGACAATTATTCCACAGGACATCAC |
| LAB38 | EcoRV | LAB38_NF_EcoRV SEQ ID NO: 754 AAAGATATCAGGAGATATGGCCCAGAGG LAB38_EF_EcoRV SEQ ID NO: 755 TTAGATATCCTGCTTGCAATACTTAGTAGAGG LAB38_NR_EcoRV SEQ ID NO: 756 AAAGATATCTTAACGTACTCTCAGGTGAGGCG LAB38_ER_EcoRV SEQ ID NO: 757 TAAGATATCTTTATTTATTCACCGGAGCAAC |
| LAB39 | SalI, XbaI | LAB39_NF_SalI SEQ ID NO: 758 AAAGTCGACCAAAATAGCAGAGATGGGAGG LAB39_NR_XbaI SEQ ID NO: 759 AAATCTAGATCACGGTAATCAGTTCAGCATGG |
| LAB40 | SalI, XbaI | LAB40_NF_SalI SEQ ID NO: 760 AAAGTCGACACACTACCAACATGGAAACATAC LAB40_EF_SalI SEQ ID NO: 761 AAAGTCGACGCTGAATCGGCACACACTAC LAB40_NR_XbaI SEQ ID NO: 762 AATTCTAGATGACCATCATCAGTTCATTGC LAB40_ER_XbaI SEQ ID NO: 763 AATTCTAGAGGAGTGAGGACTTTACAAAATG |
| LAB41 | SalI, XbaI | LAB41_NF_SalI SEQ ID NO: 764 AAAGTCGACAAGAGCTGCGAGAGGAAGG LAB41_NR_XbaI SEQ ID NO: 765 AAATCTAGATTAACATCAATTGTCAGTCATCGG |
| LAB45 | SalI, StuI | LAB45_NF_SalI SEQ ID NO: 766 AAAGTCGACATTCTTATCAAAACAGAGGAACC LAB45_EF_SalI SEQ ID NO: 767 AAAGTCGACCTCCCTCAGATTCTTATCAAAAC LAB45_NR_XbaI SEQ ID NO: 768 AAATCTAGATTAGCATCAGTTGGATACCATG LAB45_ER_XbaI SEQ ID NO: 769 AAATCTAGATTAAGTCACAAGTTGAAGCATGGTG |
| LAB49 | EcoRV, EcoRV | LAB49_NF_EcoRV SEQ ID NO: 770 AAAGATATCACGATCAGCCATGAAGAGC LAB49_NR_EcoRV SEQ ID NO: 771 AAAGATATCTTATTAAGCTGGCTGGTTGTGAC |
| LAB5 | | LAB5_EF_EcoRV SEQ ID NO: 772 AAAGATATCCTCTTCCACAATCCACATTCC LAB5_ER_PstI SEQ ID NO: 773 AATCTGCAGTGACGATCCATCTATGAACAAC |
| LAB50 | | LAB50_NF_SalI SEQ ID NO: 774 AAAGTCGACCACGGAGAAAAGAAAGATCG LAB50_NR_XbaI SEQ ID NO: 775 AAATCTAGATTAAAACTCCGGCTGCTAGACC |
| LAB51 | SalI, XbaI | LAB51_NF_SalI SEQ ID NO: 776 AAAGTCGACAGTACTTCGGTTGATGGCTTC LAB51_EF_SalI SEQ ID NO: 777 AAAGTCGACCTCTGCTCGTCTCTGCATTTAG |

TABLE 7-continued

Provided are primers and the restriction sites and enzymes used for cloning selected genes (polynucleotides, provided by gene name) identified herein.
PCR primers for cloning selected genes of the invention

| Gene Name | Restriction Enzymes used for cloning | Primers used for amplification (SEQ ID NOs:) |
|---|---|---|
| LAB51 | | LAB51_NR_XbaI SEQ ID NO: 778 AAATCTAGATTAAACACTTATGTATGCACGCTTAG LAB51_ER_XbaI SEQ ID NO: 779 AAATCTAGATTATCCACACCAAGACCAAGACAG |

TABLE 8

Restriction enzymes and cloning vectors used to clone selected genes of the invention

| Gene name | Binary vector | Restriction enzymes used for cloning into binary vector - FORWARD | Restriction enzymes used for cloning into binary vector - REVERSE | Restriction enzymes used for digesting the binary vector |
|---|---|---|---|---|
| BDL103 | pBXYN (pGI_35S) | XbaI | Sac I | XbaI, Sac I |
| BDL103 | pBXYN (pGI_35S) | SalI | EcoR I | SalI, EcoR I |
| BDL11 | pM (pMBLArt) | NotI | Not I | NotI, Not I |
| BDL12 | pBXYN (pGI_35S) | HindIII | EcoR I | HindIII, EcoR I |
| BDL14 | pBXYN (pGI_35S) | HindIII | EcoRI | HindIII, EcoRI |
| BDL166 | pQXYN | XbaI | EcoRI | XbaI, EcoRI |
| BDL17 | pM (pMBLArt) | NotI | Not I | NotI, Not I |
| BDL17S | pM (pMBLArt) | NotI | Not I | NotI, Not I |
| BDL210 | pQXYN | SalI | EcoRI | SalI, EcoRI |
| CTF113 | pBXYN (pGI_35S) | SmaI | Sac I | SmaI, SacI |
| CTF163 | pQXYN | SalI | SacI | SalI, SacI |
| CTF175 | pBXYN (pGI_35S) | EcoRV | Sac I | SmaI, SacI |
| CTF180 | pQXYN | SalI | EcoRI | SalI, EcoRI |
| CTF205 | pQXYN | SalI | SacI | SalI, SacI |
| CTF215 | pQXYN | SalI | SacI | SalI, SacI |
| CTF226 | pQXYN | SalI | SacI | SalI, SacI |
| LAB11 | pQFN | SalI | EcoRI | SalI, EcoRI |
| LAB13 | pQFN | SalI | EcoRI | SalI, EcoRI |
| LAB14 | pQYN | BamHI | SmaI | BamHI, Ecl136II |
| LAB15 | pQFN | SalI | Ecl136II | SalI, StuI |
| LAB16 | pQFN | SalI | EcoRI | SalI, EcoRI |
| LAB17 | pQFN | EcoRV | SmaI | StuI, StuI |
| LAB18 | pQFN | SalI | Ecl136II | SalI, StuI |
| LAB2 | pQFN | EcoRV | SmaI | StuI, StuI |
| LAB20 | pQYN | HindIII | SmaI | HindIII, Ecl136II |
| LAB21 | pQFN | SalI | EcoRI | SalI, EcoRI |
| LAB22 | pQFN | SalI | XbaI | SalI, XbaI |
| LAB23 | pQFN | EcoRV | EcoRV | StuI, StuI |
| LAB24 | pQYN_6669 | SalI | EcoRI | SalI, EcoRI |
| LAB25 | pQFN | SalI | EcoRI | SalI, EcoRI |
| LAB3 | pQFN | SalI | EcoRI | SalI, EcoRI |
| LAB31 | pQYN | BamHI | SmaI | BamHI, Ecl136II |
| LAB32 | pQFN | SalI | EcoRI | SalI, EcoRI |
| LAB33 | pQFN | EcoRV | EcoRV | StuI, StuI |
| LAB34 | pQFN | SalI | EcoRI | SalI, EcoRI |
| LAB35 | pQFN | SalI | Ecl136II | SalI, StuI |
| LAB36 | pQFN | SalI | EcoRV | SalI, StuI |
| LAB38 | pQYN | BamHI | SmaI | BamHI, Ecl136II |
| LAB39 | pQFN | SalI | EcoRI | SalI, EcoRI |
| LAB4 | pQFN | EcoRV | EcoRV | SmaI, SmaI |
| LAB40 | pQFN | SalI | EcoRI | SalI, EcoRI |
| LAB41 | pQYN_6669 | SalI | EcoRI | SalI, EcoRI |
| LAB45 | pQFN | SalI | BamHI | SalI, BamHI |
| LAB49 | pQFN | EcoRV | Ecl136II | StuI, StuI |
| LAB5 | pQFN | EcoRV | KpnI | StuI, KpnI |
| LAB50 | pQFN | SalI | BamHI | SalI, BamHI |
| LAB51 | pQYN_6669 | SalI | EcoRI | SalI, EcoRI |
| LAB8 | pQFN | BamHI | XhoI | BamHI, XhoI |
| LAB9 | pQFN | BamHI | KpnI | BamHI, KpnI |

Table 8: Provided are the restriction enzymes and cloning vectors used for cloning selected genes of the invention.

TABLE 9

Primers used for colony screening of the binary plasmid

| Gene Name | Colony Screening FP Name | FP SEQ ID NO: | Colony Screening RP Name | RP SEQ ID NO: |
|---|---|---|---|---|
| BDL103_Long | 35S_1F | 780 | NOS R | 784 |
| BDL103_Short | BDL103_Short_F_SalI | 677 | 101_ER | 785 |
| BDL11_GA | 35S_1F | 780 | 101_R | 786 |
| BDL12 | 101 EF | 781 | BDL12_gDNA_NR_SacI | 680 |
| BDL14 | BDL14_ORF_F1_SalI | 681 | 101_R | 786 |
| BDL166 | 35S_1F | 780 | BDL166_NR_SacI | 685 |
| BDL17 | 35S_1F | 780 | 101_R | 786 |
| BDL17 | 101-F | 782 | BDL17_GA_R | 787 |
| BDL210 | 35S_1F | 780 | BDL210_NR_XbaI | 688 |
| CTF113 | 35S_1F | 780 | NOS R | 784 |
| CTF163 | 35S_1F | 780 | CTF163_NR_XbaI | 693 |
| CTF175 | 35S_1F | 780 | NOS R | 784 |
| CTF180 | 35S_1F | 780 | CTF180_NR_SacI | 700 |
| CTF205 | 35S_1F | 780 | CTF205_ER_XbaI | 702 |
| CTF215 | 35S_1F | 780 | CTF215_NR_XbaI | 704 |
| CTF226 | 35S_1F | 780 | CTF226_NR_XbaI | 707 |
| LAB11 | 6669 F | 783 | LAB11_NR_XbaI | 710 |
| LAB13 | 6669 F | 783 | 101_R | 786 |
| LAB14 | p6669-F | 783 | 101_ER | 785 |
| LAB15 | p6669-F | 783 | 101_ER | 785 |
| LAB16 | 6669 F | 783 | LAB16_NR_XbaI | 716 |
| LAB17 | p6669-F | 783 | LAB17_NR_PstI | 718 |
| LAB18 | p6669-F | 783 | 101_ER | 785 |
| LAB2 | p6669-F | 783 | LAB2_NR_PstI | 721 |
| LAB20 | 101-F | 782 | LAB20_NR_SmaI | 724 |
| LAB21 | 6669 F | 783 | LAB21_NR_XbaI | 726 |
| LAB22 | 6669 F | 783 | LAB22_NR_XbaI | 728 |
| LAB23 | p6669-F | 783 | LAB14_NR_EcoRV | 714 |
| LAB24 | 6669 F | 783 | LAB24_NR_XbaI | 732 |
| LAB25 | 6669 F | 783 | LAB25_NR_XbaI | 734 |
| LAB3 | 6669 F | 783 | LAB3_NR_XbaI | 736 |
| LAB31 | LAB31 NF EcoRV | 737 | 101 EF | 781 |
| LAB32 | 6669 F | 783 | LAB32_NR_XbaI | 741 |
| LAB33 | p6669-F | 783 | LAB33_R1_seq | 788 |
| LAB34 | 6669 F | 783 | LAB34_NR_XbaI | 745 |
| LAB35 | 6669 F | 783 | LAB35_NR_XbaI | 748 |
| LAB36 | 6669 F | 783 | LAB36_NR_XbaI | 752 |
| LAB38 | LAB38_NF_EcoRV | 754 | 101 EF | 781 |
| LAB39 | 6669 F | 783 | LAB39_NR_XbaI | 759 |
| LAB4 | 6669 F | 783 | LAB4_R_GA | 789 |
| LAB40 | 6669 F | 783 | LAB40_NR_XbaI | 762 |
| LAB41 | 6669 F | 783 | LAB41_NR_XbaI | 765 |
| LAB45 | 6669 F | 783 | LAB45_NR_XbaI | 790 |
| LAB49 | 6669 F | 783 | LAB49_NR_EcoRV | 771 |
| LAB5 | p6669-F | 783 | 101_ER | 785 |
| LAB50 | 6669 F | 783 | LAB50_NR_XbaI | 775 |
| LAB51 | 6669 F | 783 | LAB51_NR_XbaI | 778 |
| LAB8 | 6669 F | 783 | LAB8_GA_rev | 791 |
| LAB9 | 6669 F | 783 | LAB9_GA_rev | 792 |

Table 9. Provided are the forward primers (FP) and reverse primers (RP) along with their sequence identifiers used for screening of colonies harboring the cloned genes of some embodiments of the invention.

TABLE 10

Cloned genes from cDNA libraries or genomic DNA and the polypeptides encoded thereby

| Gene Name | High copy plasmid | Amplified from Organism | Origin | Polynuc. SEQ ID NO: | Polypep. SEQ ID NO: |
|---|---|---|---|---|---|
| BDL103_Long | | | GeneArt | 670 | 96 |
| BDL103_Short | pGXN (pKG + Nos + 35S) | RICE *Oryza sativa* L. *Japonica* ND | cDNA-RICE | 671 | 672 |
| BDL11 | pGXN (pKG + Nos + 35S) | | GeneArt | 639 | 661 |
| BDL12 | pGXN (pKG + Nos + 35S) | *ARABIDOPSIS Arabidopsis thaliana* ND | gDNA | 640 | 662 |
| BDL14 | pGXN (pKG + Nos + 35S) | *ARABIDOPSIS Arabidopsis thaliana* ND | cDNA | 641 | 99 |
| BDL166 | pGXN (pKG + Nos + 35S) | *ARABIDOPSIS Arabidopsis thaliana* ND | cDNA | 642 | 100 |

TABLE 10-continued

Cloned genes from cDNA libraries or genomic DNA and the polypeptides encoded thereby

| Gene Name | High copy plasmid | Amplified from Organism | Origin | Polynuc. SEQ ID NO: | Polypep. SEQ ID NO: |
|---|---|---|---|---|---|
| BDL17 | pGXN (pKG + Nos + 35S) | | GeneArt | 643 | 101 |
| BDL17 | pGN_Napin | | GeneArt | 643 | 101 |
| BDL210 | pGXN (pKG + Nos + 35S) | ARABIDOPSIS Arabidopsis thaliana ND | cDNA | 644 | 102 |
| CTF113 | pKS(Pks_J) | Cotton | cDNA | 645 | 663 |
| CTF163 | pGXN (pKG + Nos + 35S) | COTTON Gossypium barbadense ND | cDNA | 646 | 664 |
| CTF175 | pKS(Pks_J) | Cotton | cDNA | 647 | 665 |
| CTF180 | pGXN (pKG + Nos + 35S) | COTTON Gossypium barbadense ND | cDNA | 648 | 666 |
| CTF205 | pGXN (pKG + Nos + 35S) | COTTON Gossypium barbadense ND | cDNA | 649 | 667 |
| CTF215 | pGXN (pKG + Nos + 35S) | COTTON Gossypium barbadense ND | cDNA | 650 | 668 |
| CTF226 | pGXN (pKG + Nos + 35S) | COTTON Gossypium barbadense ND | cDNA | 651 | 669 |
| LAB11 | pGXN (pKG + Nos + 35S) | RICE Oryza sativa L. Japonica ND | cDNA | 609 | 65 |
| LAB13 | pGXN (pKG + Nos + 35S) | RICE Oryza sativa L. Japonica ND | cDNA | 610 | 66 |
| LAB14 | pKSJ_6669a | RICE Oryza sativa L. Japonica ND | cDNA | 611 | 67 |
| LAB15 | | | GeneArt | 612 | 68 |
| LAB16 | pGXN (pKG + Nos + 35S) | COTTON Gossypium barbadense ND | cDNA | 614 | 70 |
| LAB17 | pKSJ_6669a | SORGHUM Sorghum bicolor Monsanto S5 | cDNA | 615 | 71 |
| LAB18 | | | GeneArt | 616 | 72 |
| LAB2 | pKS(Pks_J) | BARLEY Hordeum vulgare L. ND | cDNA | 613 | 69 |
| LAB20 | pUC19_pr6669 | RICE Oryza sativa L. Japonica ND | cDNA | 617 | 73 |
| LAB21 | pGXN (pKG + Nos + 35S) | BARLEY Hordeum vulgare L. ND | cDNA | 618 | 653 |
| LAB22 | pGXN (pKG + Nos + 35S) | SORGHUM Sorghum bicolor Monsanto S5 | cDNA | 619 | 75 |
| LAB23 | pKSJ_6669a | BARLEY Hordeum vulgare L. ND | cDNA | 621 | 77 |
| LAB24 | pGXN (pKG + Nos + 35S) | SORGHUM Sorghum bicolor Monsanto S5 | cDNA | 622 | 655 |
| LAB25 | pGXN (pKG + Nos + 35S) | BARLEY Hordeum vulgare L. ND | cDNA | 623 | 656 |
| LAB3 | pGXN (pKG + Nos + 35S) | COTTON Gossypium hirsutum Akala | cDNA | 620 | 654 |
| LAB31 | pKSJ_6669a | COTTON Gossypium hirsutum Akala | cDNA | 624 | 81 |
| LAB32 | pGXN (pKG + Nos + 35S) | BARLEY Hordeum vulgare L. ND | cDNA | 625 | 82 |
| LAB33 | pKS(Pks_J) | SORGHUM Sorghum bicolor Monsanto S5 | cDNA | 626 | 83 |
| LAB34 | pGXN (pKG + Nos + 35S) | SOYBEAN Glycine max ND | cDNA | 627 | 657 |
| LAB35 | Topo B | WHEAT Triticum aestivum L. ND | cDNA | 628 | 658 |
| LAB36 | Topo B | SORGHUM Sorghum bicolor Monsanto S5 | cDNA | 629 | 86 |
| LAB38 | pKSJ_6669a | WHEAT Triticum aestivum L. ND | cDNA | 630 | 87 |
| LAB39 | pGXN (pKG + Nos + 35S) | SORGHUM Sorghum bicolor Monsanto S5 | cDNA | 631 | 659 |
| LAB4 | | | GeneArt | 605 | 60 |
| LAB40 | pGXN (pKG + Nos + 35S) | SORGHUM Sorghum bicolor Monsanto S5 | cDNA | 632 | 660 |
| LAB41 | pGXN (pKG + Nos + 35S) | WHEAT Triticum aestivum L. ND | cDNA | 633 | 90 |
| LAB45 | TopoB_LAB45 | SORGHUM Sorghum bicolor Monsanto S5 | cDNA + part from GA | 634 | 92 |
| LAB49 | pKSJ_6669a | RICE Oryza sativa L. Japonica ND | cDNA | 635 | 93 |
| LAB5 | Topo B | SORGHUM Sorghum bicolor Monsanto S5 | cDNA | 606 | 652 |

TABLE 10-continued

Cloned genes from cDNA libraries or genomic DNA and the polypeptides encoded thereby

| Gene Name | High copy plasmid | Amplified from | | Polynuc. SEQ ID NO: | Polypep. SEQ ID NO: |
|---|---|---|---|---|---|
| | | Organism | Origin | | |
| LAB50 | Topo B | RICE *Oryza sativa* L. *Japonica* ND | cDNA | 636 | 94 |
| LAB51 | pGXN (pKG + Nos + 35S) | WHEAT *Triticum aestivum* L. ND | cDNA | 637 | 95 |
| LAB8 | | | GeneArt | 607 | 63 |
| LAB9 | | | GeneArt | 608 | 64 |

Table 10. Provided are the cloned and synthetic genes, the polypeptides encoded thereby along with their sequence identifiers. Also provided are the source of DNA used for cloning (cDNA or genomic DNA) and the organism from which the gene was cloned. Polynuc. = polynucleotide; Polypep. = polypeptide. BDL103 short was amplified from pGXN_BDL103. pGXN_BDL103 was amplified from cDNA-RICE *Oryza sativa* L. *Japonica* ND. LAB45 was composed of a part cloned from cDNA with the primers indicated and a part ordered from GA PCR products were digested with the restriction endonucleases (Roche, Switzerland) according to the sites design in the primers (Table 7). Each digested PCR product was inserted into a high copy vector originated from pBlue-script KS plasmid vector (pBlue-script KS plasmid vector, Hypertext Transfer Protocol://World Wide Web (dot) stratagene (dot) com/manuals/212205 (dot) pdf) or pUC19 (New England BioLabs Inc). In case of the high copy vector originated from pBlue-script KS plasmid vector (pGXN) the PCR product was inserted in the high copy plasmid upstream to the NOS terminator (SEQ ID NO:673) originated from pBI 101.3 binary vector (GenBank Accession No. U12640, nucleotides 4417 to 4693) and down stream to the 35S promoter (SEQ ID NO:675). In other cases (pKSJ_6669a or pUC19_pr6669) the At6669 promoter (SEQ ID NO:674) was already cloned into the pBlue-script KS or pUC19 respectively, so the gene was introduced downstream of the promoter.

Sequencing of the inserted genes was performed, using the ABI 377 sequencer (Applied Biosystems). In all the cases, after confirming the sequences of the cloned genes, the cloned cDNA accompanied with the NOS terminator was introduced into a modified pGI binary vector containing the At6669 promoter via digestion with appropriate restriction endonucleases. In other cases the cloned cDNA accompanied with the At6669 promoter was introduced into a pGI vector (that hasn't already contained the At6669 promoter). In any case the insert was followed by single copy of the NOS terminator (SEQ ID NO: 673). Part of the genes were introduced into a binary vector pGI containing the 35S promoter. The digested products and the linearized plasmid vector were ligated using T4 DNA ligase enzyme (Roche, Switzerland).

Several DNA sequences of the selected genes were synthesized by GeneArt (Hypertext Transfer Protocol://World Wide Web (dot) geneart (dot) com/). Synthetic DNA is designed in silico. Suitable restriction enzymes sites are added to the cloned sequences at the 5' end and at the 3' end to enable later cloning into the desired binary vector.

The pPI plasmid vector is constructed by inserting a synthetic poly-(A) signal sequence, originating from pGL3 basic plasmid vector (Promega, GenBank Accession No. U47295; nucleotides 4658-4811) into the HindIII restriction site of the binary vector pBI101.3 (Clontech, GenBank Accession No. U12640). pGI (FIG. 1) is similar to pPI, but the original gene in the back bone is GUS-Intron, rather than GUS.

Figure 2:
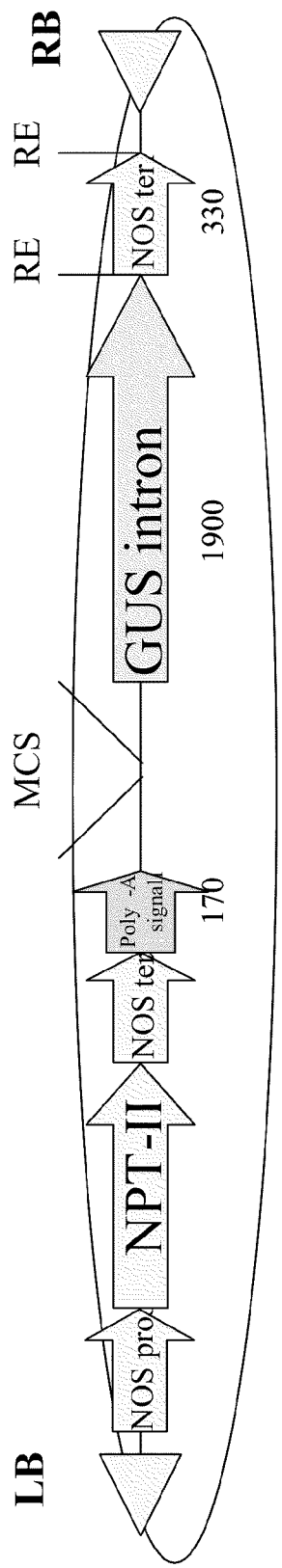
FIG. 2 is a schematic illustration of the modified pGI binary plasmid used for expressing the isolated polynucleotide sequences of the invention. RD—T-DNA right border; LB—T-DNA left border; MCS—Multiple cloning site; RE—any restriction enzyme; (numbers)—Length in base-pairs; NOS pro=nopaline synthase promoter; NPT-II=neomycin phosphotransferase gene; NOS ter=nopaline synthase terminator; Poly-A signal (polyadenylation signal); GUSintron—the GUS reporter gene (coding sequence and intron) The isolated polynucleotide sequences of the invention were cloned into the vector while replacing the GUSintron reporter gene.

The modified pGI vector (FIG. 2) is a modified version of the pGI vector in which the cassette is inverted between the left and right borders so the gene and its corresponding promoter are close to the right border and the NPTII gene is close to the left border.

At6669, the *Arabidopsis thaliana* promoter sequence (set forth in SEQ ID NO: 674) was inserted in the pGI binary vector, upstream to the cloned genes, followed by DNA ligation and binary plasmid extraction from positive *E. coli* colonies, as described above. Colonies were analyzed by PCR using the primers covering the insert which were designed to span the introduced promoter and gene. Positive plasmids were identified, isolated and sequenced as described above.

Some genes were cloned downstream of the Napin promoter (SEQ ID NO:676) and upstream to the NOS terminator in the pMBLArt vector. The vector displays resistance to Basta.

Promoters used: *Arabidopsis* At6669 promoter (SEQ ID NO: 674; which is SEQ ID NO: 61 of WO04081173), Napin (SEQ ID NO: 676) and 35S (SEQ ID NO: 675).

Example 4

Transforming *Agrobacterium Tumefaciens* Cells with Binary Vectors Harboring Putative Genes Each of the binary vectors described in Example 3 above were used to transform *Agrobacterium* cells. Two additional binary constructs, having a GUS/Luciferase reporter gene replacing the selected gene (positioned downstream of the At6669 promoter), were used as negative controls.

The binary vectors were introduced to *Agrobacterium tumefaciens* GV301, or LB4404 competent cells (about $10^9$ cells/mL) by electroporation. The electroporation was performed using a MicroPulser electroporator (Biorad), 0.2 cm cuvettes (Biorad) and EC-2 electroporation program (Biorad). The treated cells were cultured in LB liquid medium at 28° C. for 3 hours, then plated over LB agar supplemented with gentamycin (50 mg/L; for *Agrobacterium* strains GV301) or streptomycin (300 mg/L; for *Agrobacterium* strain LB4404) and kanamycin (50 mg/L) at 28° C. for 48 hours. *Abrobacterium* colonies developed on the selective media were analyzed by PCR using the primers which are designed to span the inserted sequence in the pPI plasmid. The resulting PCR products were isolated and sequenced as described in Example 3 above, to verify that the correct polynucleotide sequences were properly introduced to the *Agrobacterium* cells.

Example 5

Transformation of *Arabidopsis Thaliana* Plants with the Identified Polynucleotides of the Invention

*Arabidopsis thaliana* Columbia plants (T0 plants) were transformed according to the Floral Dip procedure [Clough S J, Bent A F. (1998) Floral dip: a simplified method for *Agrobacterium*-mediated transformation of *Arabidopsis thaliana*. Plant J. 16 (6): 735-43] and Desfeux C, Clough S J, Bent A F. (2000) [Female reproductive tissues are the primary targets of *Agrobacterium*-mediated transformation by the *Arabidopsis* floral-dip method. Plant Physiol. 123 (3): 895-904] with minor modifications. Briefly, $T_0$ Plants were sown in 250 ml pots filled with wet peat-based growth mix. The pots were covered with aluminum foil and a plastic dome, kept at 4° C. for 3-4 days, then uncovered and incubated in a growth chamber at 18-24° C. under 16/8 hour light/dark cycles. The To plants were ready for transformation six days before anthesis.

Single colonies of *Agrobacterium* carrying the binary constructs were generated as described in Example 4 above. Colonies were cultured in LB medium supplemented with kanamycin (50 mg/L) and gentamycin (50 mg/L). The cultures were incubated at 28° C. for 48 hours under vigorous shaking and then centrifuged at 4000 rpm for 5 minutes. The pellets comprising the *Agrobacterium* cells were re-suspended in a transformation medium containing half-strength (2.15 g/L) Murashige-Skoog (Duchefa); 0.044 µM benzylamino purine (Sigma); 112 µg/L B5 Gambourg vitamins (Sigma); 5% sucrose; and 0.2 ml/L Silwet L-77 (OSI Specialists, CT) in double-distilled water, at pH of 5.7.

Transformation of $T_0$ plants was performed by inverting each plant into an *Agrobacterium* suspension, such that the above ground plant tissue was submerged for 3-5 seconds. Each inoculated $T_0$ plant was immediately placed in a plastic tray, then covered with clear plastic dome to maintain humidity and was kept in the dark at room temperature for 18 hours, to facilitate infection and transformation. Transformed (transgenic) plants were then uncovered and transferred to a greenhouse for recovery and maturation. The transgenic $T_0$ plants were grown in the greenhouse for 3-5 weeks until siliques were brown and dry. Seeds were harvested from plants and kept at room temperature until sowing.

For generating $T_1$ and $T_2$ transgenic plants harboring the genes, seeds collected from transgenic $T_0$ plants were surface-sterilized by soaking in 70% ethanol for 1 minute, followed by soaking in 5% sodium hypochloride and 0.05% triton for 5 minutes. The surface-sterilized seeds were thoroughly washed in sterile distilled water then placed on culture plates containing half-strength Murashige-Skoog (Duchefa); 2% sucrose; 0.8% plant agar; 50 mM kanamycin; and 200 mM carbenicylin (Duchefa). The culture plates were incubated at 4° C. for 48 hours then transferred to a growth room at 25° C. for an additional week of incubation. Vital $T_1$ *Arabidopsis* plants were transferred to a fresh culture plates for another week of incubation. Following incubation the $T_1$ plants were removed from culture plates and planted in growth mix contained in 250 ml pots. The transgenic plants were allowed to grow in a greenhouse to maturity. Seeds harvested from $T_1$ plants were cultured and grown to maturity as $T_2$ plants under the same conditions as used for culturing and growing the $T_1$ plants.

Example 6

Transgenic Plants Overexpressing the Polynucleotides of Some Embodiments of the Invention Exhibit Increased ABST, NUE, Biomass and/or Growth Rate Plants transgenic to the polynucleotides of some embodiments of the invention were assayed for fertilizer use efficiency in a tissue culture assay.

Assay 1: Plant Growth at Nitrogen Deficiency Under Tissue Culture Conditions

The present inventors have found the nitrogen use efficiency (NUE) assay to be relevant for the evaluation of the ABST candidate genes, since nitrogen limiting conditions encourage root elongation, increases root coverage and allows detecting the potential of the plant to generate a better root system under drought conditions. In addition, there are indications in the literature that biological mechanisms of NUE and drought tolerance are linked (Wesley et al., 2002 Journal of Experiment Botany Vol 53, No. 366, pp. 13-25).

Surface sterilized seeds were sown in basal media [50% Murashige-Skoog medium (MS) supplemented with 0.8% plant agar as solidifying agent] in the presence of Kanamycin (for selecting only transgenic plants). After sowing, plates were transferred for 2-3 days for stratification at 4° C. and then grown at 25° C. under 12-hour light 12-hour dark daily cycles for 7 to 10 days. At this time point, seedlings randomly chosen were carefully transferred to plates with nitrogen-limiting conditions: 0.5 MS media in which the combined nitrogen concentration ($NH_4NO_3$ and $KNO_3$) is 0.75 mM (nitrogen deficient conditions) or 15 mM [Normall (optimal) nitrogen concentration]. Each plate contains 5 seedlings of same event, and 3-4 different plates (replicates) for each event. For each polynucleotide of the invention at least four independent transformation events were analyzed from each construct. Plants expressing the polynucleotides of the invention were compared to the average measurement of the control plants (generated by transformation of plant with an empty vector under the same promoter or a vector comprising the GUS reporter gene under the same promoter) used in the same experiment.

Digital Imaging

A laboratory image acquisition system, which consists of a digital reflex camera (Canon EOS 300D) attached with a 55 mm focal length lens (Canon EF-S series), mounted on a reproduction device (Kaiser RS), which included 4 light units (4×150 Watts light bulb) and located in a darkroom, is used for capturing images of plantlets sawn in agar plates.

The image capturing process was repeated every 3-4 days starting at day 1 till day 10 (see for example the images in FIGS. 3A-F).

An image analysis system was used, which consists of a personal desktop computer (Intel P4 3.0 GHz processor) and a public domain program—ImageJ 1.39 (Java based image processing program which was developed at the U.S. National Institutes of Health and freely available on the internet at Hypertext Transfer Protocol://rsbweb (dot) nih (dot) gov/). Images were captured in resolution of 10 Mega Pixels (3888×2592 pixels) and stored in a low compression JPEG (Joint Photographic Experts Group standard) format. Next, analyzed data was saved to text files and processed using the JMP statistical analysis software (SAS institute).

Seedling Analysis

Using the digital analysis seedling data was calculated, including leaf area, root coverage and root length.

The relative growth rate for the various seedling parameters was calculated according to the following formulas V, VI and VII.

Relative growth rate of leaf area=Regression coefficient of leaf area along time course.     Formula V Relative growth rate of root coverage=Regression coefficient of root coverage along time course.     Formula VI Relative growth rate of root length=Regression coefficient of root length along time course.     Formula VII At the end of the experiment, plantlets were removed from the media and weighed for the determination of plant fresh weight. Plantlets were then dried for 24 hours at 60° C., and weighed again to measure plant dry weight for later statistical analysis. Growth rate was determined by comparing the leaf area coverage, root coverage and root length, between each couple of sequential photographs, and results were used to resolve the effect of the gene introduced on plant vigor, under osmotic stress, as well as under normal or optimal conditions. Similarly, the effect of the gene introduced on biomass accumulation, under osmotic stress as well as under optimal conditions, was determined by comparing the plants' fresh and dry weight to that of control plants (containing an empty vector or the GUS reporter gene under the same promoter). From every construct created, 3-5 independent transformation events were examined in replicates.

Statistical Analyses

To identify genes conferring significantly improved tolerance to abiotic stresses or enlarged root architecture, the results obtained from the transgenic plants were compared to those obtained from control plants. To identify outperforming genes and constructs, results from the independent transformation events tested were analyzed separately. To evaluate the effect of a gene event over a control the data was analyzed by Student's t-test and the p value was calculated. Results were considered significant if p≤0.1. The JMP statistics software package was used (Version 5.2.1, SAS Institute Inc., Cary, N.C., USA).

Experimental Results

The genes presented in Tables 11-18, hereinbelow, were found to increase ABST by improving root performance, plant growth characteristic and plant biomass when grown under limiting nitrogen growth conditions as compared to control plants.

Tables 11-18 depict analyses of root growth (root length and root coverage; Tables 11 and 12); plant biomass (plant fresh, dry weight and leaf area; Tables 13 and 14); root growth rate (relative growth rate of root length and root coverage; Tables 15 and 16); and leaf area and leaf area growth rate (relative growth rate of leaf area; Tables 17 and 18) when grown under limiting nitrogen conditions [low nitrogen or nitrogen deficient conditions (0.75 mM N)] in plants overexpressing the polynucleotides of some embodiments of the invention under the regulation of a constitutive promoter [35S (SEQ ID NO:675) or At6669 (SEQ ID NO:674)]. Evaluation of each gene was performed by testing the performance of several events. Some of the genes were evaluated in more than one tissue culture assay and the second experiment confirmed the significant increment in plant biomass. Event with p-value<0.05 was considered statistically significant.

TABLE 11

Transgenic *Arabidopsis* plants exogenously expressing the polynucleotides of some embodiments of the invention under the regulation of the 35S promoter exhibit improved plant roots under nitrogen deficient conditions

| Gene Name | Event # | Ave. | p-value | % incr. |
|---|---|---|---|---|
| Plant Root length [cm] | | | | |
| BDL103 | 8033.1 | 6.07 | 2.24E−04 | 22.7 |
| BDL103 | 8033.4 | 5.55 | 1.28E−02 | 12.3 |
| Control | | 4.95 | | |
| CTF163 | 11012.2 | 5.46 | 4.92E−02 | 16 |
| CTF163 | 11012.7 | 5.97 | 3.81E−03 | 27 |
| Control | | 4.71 | | 0.00 |
| CTF163 | 11011.2 | 5.86 | 7.62E−03 | 36 |

TABLE 11-continued

Transgenic *Arabidopsis* plants exogenously expressing the polynucleotides of some embodiments of the invention under the regulation of the 35S promoter exhibit improved plant roots under nitrogen deficient conditions

| Gene Name | Event # | Ave. | p-value | % incr. |
|---|---|---|---|---|
| CTF163 | 11012.2 | 6.16 | 1.70E−03 | 43 |
| CTF163 | 11012.4 | 5.64 | 3.36E−02 | 31 |
| CTF163 | 11012.7 | 6.52 | 6.74E−03 | 52 |
| Control | | 4.30 | | |
| CTF226 | 10982.3 | 7.02 | 9.00E−06 | 38 |
| Control | | 5.08 | | 0.00 |
| CTF205 | 11972.3 | 5.49 | 4.87E−02 | 14 |
| Control | | 4.83 | | 0.00 |
| Plant Root Coverage [cm$^2$] | | | | |
| CTF113 | 5871.2 | 15.17 | 3.7E−02 | 19 |
| Control | | 12.79 | | 0.00 |
| BDL103 | 8033.1 | 8.63 | 1.3E−03 | 34 |
| Control | | 6.45 | | 0.00 |
| CTF163 | 11011.2 | 7.03 | 2.1E−02 | 42 |
| CTF163 | 11012.2 | 7.59 | 2.8E−02 | 53 |
| CTF163 | 11012.7 | 8.03 | 5.5E−04 | 62 |
| Control | | 4.96 | | 0.00 |
| CTF226 | 10982.1 | 8.81 | 8.8E−03 | 63 |
| CTF226 | 10982.3 | 10.72 | 9.1E−03 | 98 |
| Control | | 5.42 | | 0.00 |
| CTF205 | 11972.3 | 6.81 | 7.3E−04 | 44 |
| Control | | 4.74 | | 0.00 |

Table 11: Analyses of plant roots (root length and root coverage) of transgenic plants overexpressing the exogenous polynucleotides of some embodiments of the invention (using the cloned or synthetic genes listed in Table 10 above) under the regulation of a constitutive promoter (35S; SEQ ID NO: 675) when grown under limiting nitrogen conditions [low nitrogen or nitrogen deficient conditions (0.75 mM N)] as compared to control plants. "Incr." = increment with respect to a control plant which has been transformed with an empty vector. Ave. = Average calculated from several transgenic events. "Event #" = number of event (transgenic transformation).

TABLE 12

Transgenic *Arabidopsis* plants exogenously expressing the polynucleotides of some embodiments of the invention under the regulation of the At6669 promoter exhibit improved plant roots under nitrogen deficient conditions

| Gene Name | Event # | Ave. | p-value | % incr. |
|---|---|---|---|---|
| Plant Root length [cm] | | | | |
| LAB31 | 11423.4 | 6.72 | 5.38E−03 | 17 |
| LAB13 | 11482.2 | 7.12 | 1.50E−02 | 24 |
| LAB41 | 11554.3 | 6.74 | 1.68E−02 | 17 |
| LAB23 | 11572.6 | 7.38 | 2.39E−04 | 28 |
| Control | | 5.77 | | |
| LAB11 | 11024.4 | 6.90 | 1.01E−02 | 22 |
| LAB22 | 11064.6 | 6.46 | 1.27E−02 | 14 |
| Control | | 5.66 | | |
| LAB32 | 11162.2 | 7.16 | 5.30E−03 | 16 |
| LAB34 | 11171.4 | 6.80 | 4.04E−02 | 11 |
| LAB38 | 11434.4 | 6.82 | 3.42E−02 | 11 |
| Control | | 6.14 | | |
| LAB20 | 11131.1 | 6.50 | 2.83E−02 | 17 |
| LAB20 | 11132.7 | 6.63 | 3.94E−03 | 19 |
| LAB9 | 12284.1 | 6.31 | 1.42E−02 | 13 |
| LAB45 | 12361.1 | 6.60 | 1.08E−02 | 19 |
| LAB45 | 12363.2 | 6.81 | 5.63E−03 | 23 |
| LAB45 | 12364.2 | 6.56 | 1.99E−02 | 18 |
| LAB45 | 12365.1 | 7.02 | 5.96E−03 | 26 |
| LAB8 | 12423.3 | 6.28 | 3.68E−02 | 13 |
| LAB8 | 12425.4 | 6.88 | 5.67E−04 | 24 |
| Control | | 5.56 | | |
| LAB32 | 11162.2 | 6.17 | 4.14E−03 | 25 |
| LAB31 | 11421.5 | 5.74 | 2.02E−02 | 16 |
| LAB31 | 11423.4 | 5.66 | 4.38E−02 | 14 |
| LAB13 | 11482.2 | 6.19 | 3.14E−03 | 25 |
| LAB8 | 12423.4 | 5.74 | 3.33E−02 | 16 |
| Control | | 4.95 | | 0.00 |
| LAB20 | 11131.1 | 6.09 | 1.16E−02 | 20 |

TABLE 12-continued

Transgenic *Arabidopsis* plants exogenously expressing the polynucleotides of some embodiments of the invention under the regulation of the At6669 promoter exhibit improved plant roots under nitrogen deficient conditions

| Gene Name | Event # | Ave. | p-value | % incr. |
|---|---|---|---|---|
| LAB20 | 11131.2 | 6.81 | 9.93E−03 | 34 |
| LAB20 | 11132.7 | 5.97 | 7.15E−04 | 18 |
| LAB20 | 11134.4 | 5.81 | 1.05E−02 | 14 |
| LAB24 | 11191.5 | 6.43 | 7.00E−05 | 27 |
| LAB24 | 11192.1 | 6.15 | 3.99E−02 | 21 |
| LAB24 | 11193.5 | 6.55 | 2.20E−04 | 29 |
| LAB24 | 11193.6 | 6.00 | 3.51E−02 | 18 |
| LAB49 | 11281.2 | 6.09 | 5.70E−05 | 20 |
| LAB49 | 11281.4 | 6.29 | 9.66E−03 | 24 |
| LAB49 | 11283.1 | 6.01 | 2.98E−03 | 18 |
| LAB49 | 11283.5 | 6.69 | 4.50E−03 | 32 |
| LAB3 | 11331.1 | 6.50 | 4.00E−06 | 28 |
| LAB3 | 11333.1 | 6.55 | 2.33E−04 | 29 |
| LAB3 | 11333.5 | 6.05 | 1.00E−04 | 19 |
| LAB3 | 11334.1 | 5.83 | 2.89E−02 | 15 |
| LAB5 | 11443.3 | 6.07 | 1.28E−04 | 20 |
| LAB5 | 11444.1 | 5.99 | 7.11E−04 | 18 |
| LAB36 | 11583.1 | 6.02 | 1.37E−02 | 19 |
| LAB36 | 11584.5 | 6.23 | 4.30E−05 | 23 |
| LAB36 | 11585.5 | 6.74 | 3.65E−03 | 33 |
| Control |  | 5.08 |  |  |
| LAB2 | 11234.2 | 5.79 | 0.025 | 15.69% |
| LAB2 | 11231.1 | 5.93 | 0.007 | 18.61% |
| Control |  | 5 |  |  |
| LAB2 | 11231.1 | 5.8 | 0.023 | 13.73% |
| Control |  | 5.1 |  |  |
| Plant Root Coverage [cm²] | | | | |
| LAB31 | 11423.4 | 9.25 | 3.9E−03 | 47 |
| LAB13 | 11482.2 | 8.91 | 4.7E−02 | 42 |
| LAB41 | 11551.2 | 8.47 | 3.3E−02 | 35 |
| LAB41 | 11554.3 | 9.09 | 1.6E−02 | 45 |
| LAB23 | 11572.6 | 12.36 | 5.5E−05 | 96 |
| Control |  | 6.29 |  | 0.00 |
| LAB11 | 11024.4 | 9.65 | 4.3E−02 | 54 |
| Control |  | 6.28 |  | 0.00 |
| LAB38 | 11434.4 | 8.50 | 4.5E−02 | 30 |
| Control |  | 6.55 |  | 0.00 |
| LAB4 | 11962.1 | 6.17 | 2.4E−02 | 20 |
| LAB4 | 11964.2 | 6.63 | 2.3E−02 | 29 |
| Control |  | 5.13 |  | 0.00 |
| LAB20 | 11131.2 | 7.66 | 3.0E−02 | 38 |
| LAB9 | 12284.1 | 9.08 | 6.5E−03 | 64 |
| LAB9 | 12286.1 | 8.19 | 8.4E−03 | 48 |
| LAB45 | 12361.1 | 9.06 | 1.3E−02 | 63 |
| LAB45 | 12361.2 | 8.20 | 3.5E−02 | 48 |
| LAB45 | 12363.2 | 7.28 | 1.0E−02 | 31 |
| LAB45 | 12365.1 | 11.21 | 1.5E−02 | 102 |
| LAB8 | 12423.3 | 7.43 | 2.9E−02 | 34 |
| LAB8 | 12425.4 | 10.37 | 1.3E−02 | 87 |
| Control |  | 5.55 |  | 0.00 |
| LAB20 | 11131.1 | 7.32 | 9.7E−03 | 42 |
| LAB20 | 11131.2 | 7.28 | 7.5E−03 | 42 |
| LAB24 | 11191.5 | 6.51 | 4.7E−02 | 27 |
| LAB24 | 11193.5 | 6.62 | 4.5E−02 | 29 |
| LAB49 | 11281.2 | 6.48 | 3.6E−02 | 26 |
| LAB49 | 11283.5 | 8.10 | 1.4E−02 | 58 |
| LAB3 | 11331.1 | 6.71 | 1.7E−02 | 30 |
| Control |  | 5.14 |  | 0.00 |

Table 12: Analyses of plant roots (root length and root coverage) of transgenic plants overexpressing the exogenous polynucleotides of some embodiments of the invention (using the cloned or synthetic genes listed in Table 10 above) under the regulation of a constitutive promoter (At6669; SEQ ID NO: 674) when grown under limiting nitrogen conditions [low nitrogen or nitrogen deficient conditions (0.75 mM N)] as compared to control plants. "Incr." = increment with respect to a control plant which has been transformed with an empty vector. Ave. = Average calculated from several transgenic events. "Event #" = number of event (transgenic transformation).

TABLE 13

Transgenic *Arabidopsis* plants exogenously expressing the polynucleotides of some embodiments of the invention under the regulation of the 35S promoter exhibit improved plant biomass under nitrogen deficient conditions

| Gene Name | Event # | Ave. | p-value | % incr. |
|---|---|---|---|---|
| Plant Fresh Weight [g] | | | | |
| CTF163 | 11011.2 | 0.10 |  | 0.00 |
| Control |  | 0.14 | 4.1E−02 | 31 |
| CTF215 | 11072.1 | 0.16 | 2.1E−02 | 27 |
| Control |  | 0.13 |  | 0.00 |
| CTF226 | 10982.1 | 0.20 | 1.0E−03 | 49 |
| CTF226 | 10982.3 | 0.18 | 4.7E−02 | 40 |
| Control |  | 0.13 |  | 0.00 |
| Plant Dry Weight [g] | | | | |
| CTF215 | 11072.1 | 0.0089 | 1.5E−03 | 53 |
| Control |  | 0.0058 |  |  |

Table 13: Analyses of plant Biomass (fresh weight and dry weight) of transgenic plants overexpressing the exogenous polynucleotides of some embodiments of the invention (using the cloned or synthetic genes listed in Table 10 above) under the regulation of a constitutive promoter (35S; SEQ ID NO: 675) when grown under limiting nitrogen conditions [low nitrogen or nitrogen deficient conditions (0.75 mM N)] as compared to control plants. "Incr." = increment with respect to a control plant which has been transformed with an empty vector. Ave. = Average calculated from several transgenic events. "Event #" = number of event (transgenic transformation).

TABLE 14

Transgenic *Arabidopsis* plants exogenously expressing the polynucleotides of some embodiments of the invention under the regulation of the At6669 promoter exhibit improved plant biomass under nitrogen deficient conditions

| Gene Name | Event # | Ave. | p-value | % incr. |
|---|---|---|---|---|
| Plant Fresh Weight [g] | | | | |
| LAB31 | 11421.5 | 0.130 | 1.9E−03 | 62 |
| LAB31 | 11423.4 | 0.125 | 2.6E−04 | 55 |
| LAB13 | 11482.2 | 0.119 | 8.8E−03 | 48 |
| LAB41 | 11554.3 | 0.119 | 7.0E−03 | 48 |
| LAB23 | 11572.6 | 0.164 | 3.7E−03 | 105 |
| Control |  | 0.080 |  | 0.00 |
| LAB11 | 11022.3 | 0.142 | 4.0E−02 | 83 |
| LAB11 | 11024.4 | 0.155 | 4.6E−04 | 99 |
| Control |  | 0.078 |  | 0.00 |
| LAB15 | 11642.2 | 0.107 | 4.0E−02 | 39 |
| Control |  | 0.077 |  | 0.00 |
| LAB18 | 11653.4 | 0.087 | 3.5E−02 | 27 |
| Control |  | 0.068 |  | 0.00 |
| LAB20 | 11131.2 | 0.120 | 6.5E−04 | 85 |
| LAB9 | 12281.2 | 0.100 | 1.1E−02 | 55 |
| LAB9 | 12286.1 | 0.108 | 4.8E−02 | 67 |
| LAB45 | 12361.2 | 0.088 | 2.6E−03 | 35 |
| Control |  | 0.065 |  | 0.00 |
| LAB32 | 11162.2 | 0.107 | 8.4E−03 | 44 |
| LAB31 | 11423.4 | 0.119 | 3.0E−02 | 60 |
| LAB13 | 11484.2 | 0.110 | 8.7E−03 | 47 |
| LAB51 | 11561.5 | 0.139 | 3.6E−03 | 86 |
| LAB51 | 11563.2 | 0.105 | 3.8E−02 | 41 |
| Control |  | 0.075 |  | 0.00 |
| LAB20 | 11131.1 | 0.095 | 4.8E−02 | 29 |
| LAB20 | 11134.4 | 0.098 | 2.2E−02 | 33 |
| LAB49 | 11283.5 | 0.109 | 6.3E−04 | 48 |
| LAB3 | 11333.5 | 0.094 | 1.5E−02 | 28 |
| LAB3 | 11334.1 | 0.096 | 2.5E−02 | 30 |
| LAB36 | 11583.1 | 0.101 | 4.0E−03 | 37 |
| LAB36 | 11584.5 | 0.090 | 3.5E−02 | 23 |
| LAB36 | 11585.5 | 0.117 | 2.1E−03 | 59 |
| Control |  | 0.073 |  | 0.00 |
| Plant Dry Weight [g] | | | | |
| LAB31 | 11423.4 | 0.0057 | 3.0E−05 | 39 |
| LAB41 | 11554.3 | 0.0062 | 6.8E−03 | 52 |
| LAB23 | 11572.6 | 0.0079 | 8.3E−04 | 93 |
| LAB23 | 11573.4 | 0.0051 | 3.8E−03 | 24 |

TABLE 14-continued

Transgenic *Arabidopsis* plants exogenously expressing the polynucleotides of some embodiments of the invention under the regulation of the At6669 promoter exhibit improved plant biomass under nitrogen deficient conditions

| Gene Name | Event # | Ave. | p-value | % incr. |
|---|---|---|---|---|
| LAB23 | 11574.2 | 0.0051 | 3.7E−02 | 26 |
| Control |  | 0.0041 |  | 0.00 |
| LAB11 | 11024.4 | 0.0069 | 2.3E−04 | 81 |
| LAB16 | 11032.2 | 0.0048 | 2.9E−02 | 25 |
| Control |  | 0.0038 |  | 0.00 |
| LAB32 | 11163.2 | 0.0061 | 2.0E−02 | 67 |
| LAB25 | 11341.2 | 0.0047 | 3.8E−02 | 28 |
| LAB38 | 11434.4 | 0.0045 | 2.8E−02 | 24 |
| LAB15 | 11642.2 | 0.0053 | 2.4E−04 | 45 |
| Control |  | 0.0037 |  | 0.00 |
| LAB18 | 11653.4 | 0.0042 | 3.1E−02 | 19 |
| Control |  | 0.0035 |  | 0.00 |
| LAB20 | 11131.2 | 0.0056 | 9.5E−04 | 91 |
| Control |  | 0.0029 |  | 0.00 |
| LAB51 | 11561.5 | 0.0070 | 2.9E−02 | 92 |
| LAB8 | 12423.1 | 0.0049 | 5.0E−02 | 36 |
| Control |  | 0.0036 |  | 0.00 |
| LAB49 | 11283.5 | 0.0054 | 8.3E−03 | 52 |
| LAB5 | 11444.5 | 0.0059 | 2.5E−03 | 65 |
| LAB36 | 11585.5 | 0.0052 | 8.7E−05 | 45 |
| Control |  | 0.0036 |  | 0.00 |

Table 14: Analyses of plant Biomass (fresh weight and dry weight) of transgenic plants overexpressing the exogenous polynucleotides of some embodiments of the invention (using the cloned or synthetic genes listed in Table 10 above) under the regulation of a constitutive promoter (At6669; SEQ ID NO: 674) when grown under limiting nitrogen conditions [low nitrogen or nitrogen deficient conditions (0.75 mM N)] as compared to control plants. "Incr." = increment with respect to a control plant which has been transformed with an empty vector. Ave. = Average calculated from several transgenic events. "Event #" = number of event (transgenic transformation).

TABLE 15

Transgenic *Arabidopsis* plants exogenously expressing the polynucleotides of some embodiments of the invention under the regulation of the 35S promoter exhibit improved plant biomass and growth rate under nitrogen deficient conditions

| Gene Name | Event # | Ave. | p-value | % incr. |
|---|---|---|---|---|
| *Relative growth rate of root length (regression coefficient)* | | | | |
| BDL103 | 8033.1 | 0.571 | 2.2E−03 | 28.0% |
| BDL103 | 8033.4 | 0.543 | 8.5E−03 | 21.9% |
| Control |  | 0.446 |  | 0.0% |
| CTF163 | 11012.2 | 0.525 | 5.0E−04 | 28.2% |
| CTF163 | 11012.7 | 0.517 | 5.3E−03 | 26.2% |
| CTF215 | 11073.4 | 0.507 | 1.9E−02 | 23.7% |
| Control |  | 0.410 |  | 0.0% |
| CTF163 | 11011.2 | 0.542 | 5.7E−04 | 43.0% |
| CTF163 | 11012.2 | 0.573 | 2.2E−04 | 51.2% |
| CTF163 | 11012.4 | 0.503 | 1.7E−02 | 32.8% |
| CTF163 | 11012.7 | 0.572 | 1.2E−04 | 50.9% |
| Control |  | 0.379 |  | 0.0% |
| CTF226 | 10982.3 | 0.646 | 1.5E−04 | 34.8% |
| Control |  | 0.480 |  | 0.0% |
| *Relative growth rate of root coverage (regression coefficient)* | | | | |
| BDL103 | 8033.1 | 0.96 | 2.2E−03 | 38 |
| Control |  | 0.70 |  | 0.0 |
| CTF163 | 11011.2 | 0.74 | 2.0E−02 | 33 |
| Control |  | 0.55 |  | 0.0 |
| CTF163 | 11011.2 | 0.84 | 1.8E−03 | 48 |
| CTF163 | 11012.2 | 0.91 | 1.4E−03 | 61 |
| CTF163 | 11012.7 | 0.95 | 2.9E−05 | 67 |
| Control |  | 0.57 |  | 0.0 |
| CTF226 | 10982.1 | 1.06 | 6.7E−05 | 68 |
| CTF226 | 10982.3 | 1.25 | 1.0E−06 | 99 |
| CTF226 | 10985.1 | 0.80 | 4.9E−02 | 28 |
| Control |  | 0.63 |  | 0.0 |

TABLE 15-continued

Transgenic *Arabidopsis* plants exogenously expressing the polynucleotides of some embodiments of the invention under the regulation of the 35S promoter exhibit improved plant biomass and growth rate under nitrogen deficient conditions

| Gene Name | Event # | Ave. | p-value | % incr. |
|---|---|---|---|---|
| CTF205 | 11972.3 | 0.76 | 1.2E−03 | 37 |
| Control |  | 0.56 |  | 0.0 |

Table 15: Analyses of root growth rate (relative growth rate of root length and root coverage) of transgenic plants overexpressing the exogenous polynucleotides of some embodiments of the invention (using the cloned or synthetic genes listed in Table 10 above) under the regulation of a constitutive promoter (35S; SEQ ID NO: 675) when grown under limiting nitrogen conditions [low nitrogen or nitrogen deficient conditions (0.75 mM N)] as compared to control plants. "Incr." = increment with respect to a control plant which has been transformed with an empty vector. Ave. = Average calculated from several transgenic events. "Event #" = number of event (transgenic transformation).

TABLE 16

Transgenic *Arabidopsis* plants exogenously expressing the polynucleotides of some embodiments of the invention under the regulation of the At6669 promoter exhibit improved plant biomass and growth rate under nitrogen deficient conditions

| Gene Name | Event # | Ave. | p-value | % incr. |
|---|---|---|---|---|
| *Relative growth rate of root length (Regression coefficient)* | | | | |
| LAB31 | 11422.1 | 0.58 | 2.8E−02 | 24 |
| LAB31 | 11423.4 | 0.62 | 1.3E−03 | 31 |
| LAB13 | 11482.2 | 0.58 | 2.5E−02 | 24 |
| LAB41 | 11551.2 | 0.59 | 4.0E−02 | 26 |
| LAB23 | 11572.6 | 0.62 | 4.0E−03 | 31 |
| Control |  | 0.47 |  | 0.0 |
| LAB32 | 11162.2 | 0.63 | 6.1E−03 | 22 |
| LAB34 | 11171.4 | 0.62 | 6.5E−03 | 22 |
| LAB38 | 11434.4 | 0.62 | 9.8E−03 | 20 |
| Control |  | 0.51 |  | 0.0 |
| LAB4 | 11964.2 | 0.57 | 2.6E−02 | 28 |
| Control |  | 0.44 |  | 0.0 |
| LAB20 | 11131.1 | 0.58 | 4.8E−02 | 27 |
| LAB45 | 12365.1 | 0.60 | 4.0E−02 | 30 |
| LAB8 | 12425.4 | 0.59 | 3.7E−02 | 28 |
| Control |  | 0.46 |  | 0.0 |
| LAB20 | 11131.2 | 0.56 | 1.4E−04 | 42 |
| LAB20 | 11132.1 | 0.46 | 3.5E−02 | 17 |
| LAB24 | 11191.5 | 0.51 | 1.7E−04 | 31 |
| LAB24 | 11193.5 | 0.48 | 3.3E−03 | 22 |
| LAB24 | 11193.6 | 0.49 | 4.4E−03 | 24 |
| LAB49 | 11281.2 | 0.50 | 7.1E−04 | 26 |
| LAB49 | 11283.5 | 0.57 | 1.7E−05 | 46 |
| LAB3 | 11331.1 | 0.52 | 1.0E−05 | 33 |
| LAB3 | 11333.1 | 0.49 | 9.0E−04 | 25 |
| LAB3 | 11334.1 | 0.45 | 4.4E−02 | 15 |
| LAB5 | 11443.3 | 0.45 | 5.0E−02 | 13 |
| LAB5 | 11444.1 | 0.53 | 1.4E−05 | 34 |
| LAB5 | 11444.5 | 0.48 | 6.6E−03 | 22 |
| LAB36 | 11584.5 | 0.50 | 2.7E−04 | 27 |
| LAB36 | 11585.5 | 0.53 | 1.2E−04 | 34 |
| Control |  | 0.39 |  | 0.0 |
| *Relative growth rate of root coverage (regression coefficient)* | | | | |
| LAB31 | 11421.5 | 1.01 | 3.0E−02 | 42 |
| LAB31 | 11423.4 | 1.09 | 2.8E−03 | 54 |
| LAB13 | 11482.2 | 1.05 | 1.2E−02 | 49 |
| LAB41 | 11551.2 | 1.00 | 2.4E−02 | 41 |
| LAB41 | 11554.3 | 1.07 | 5.6E−03 | 51 |
| LAB23 | 11572.6 | 1.45 | 1.0E−06 | 105 |
| Control |  | 0.71 |  | 0.0 |
| LAB11 | 11024.4 | 1.13 | 6.0E−03 | 59 |
| Control |  | 0.71 |  | 0.0 |
| LAB32 | 11162.2 | 1.00 | 5.1E−03 | 36 |
| LAB34 | 11171.4 | 0.96 | 7.1E−03 | 30 |
| LAB38 | 11434.4 | 1.01 | 3.4E−03 | 36 |
| LAB15 | 11642.2 | 1.05 | 5.2E−03 | 42 |
| LAB15 | 11644.1 | 0.96 | 8.0E−03 | 30 |

TABLE 16-continued

Transgenic *Arabidopsis* plants exogenously expressing the polynucleotides of some embodiments of the invention under the regulation of the At6669 promoter exhibit improved plant biomass and growth rate under nitrogen deficient conditions

| Gene Name | Event # | Ave. | p-value | % incr. |
|---|---|---|---|---|
| Control | | 0.74 | | 0.0 |
| LAB4 | 11964.1 | 0.85 | 4.3E−02 | 41 |
| Control | | 0.60 | | 0.0 |
| LAB4 | 11964.2 | 0.75 | 2.9E−02 | 32 |
| Control | | 0.56 | | 0.0 |
| LAB20 | 11131.1 | 0.88 | 3.5E−03 | 39 |
| LAB20 | 11132.7 | 0.81 | 3.7E−02 | 27 |
| LAB9 | 12284.1 | 1.06 | 1.7E−05 | 68 |
| LAB9 | 12286.1 | 0.96 | 2.4E−04 | 51 |
| LAB45 | 12361.1 | 1.05 | 4.6E−05 | 66 |
| LAB45 | 12361.2 | 0.95 | 1.3E−03 | 50 |
| LAB45 | 12363.2 | 0.83 | 1.2E−02 | 30 |
| LAB45 | 12364.2 | 1.16 | 2.7E−04 | 83 |
| LAB45 | 12365.1 | 1.30 | 0.0E+00 | 105 |
| LAB8 | 12423.3 | 0.88 | 2.0E−03 | 39 |
| LAB8 | 12425.4 | 1.22 | 2.0E−06 | 92 |
| Control | | 0.63 | | 0.0 |
| LAB20 | 11131.1 | 0.80 | 1.5E−02 | 41 |
| LAB20 | 11131.2 | 0.85 | 3.4E−03 | 49 |
| LAB24 | 11191.5 | 0.74 | 4.9E−02 | 30 |
| LAB24 | 11193.6 | 0.76 | 4.7E−02 | 34 |
| LAB49 | 11281.2 | 0.74 | 4.0E−02 | 31 |
| LAB49 | 11283.5 | 0.97 | 4.0E−04 | 72 |
| LAB3 | 11331.1 | 0.76 | 3.1E−02 | 34 |
| LAB36 | 11584.5 | 0.74 | 4.3E−02 | 31 |
| LAB36 | 11585.5 | 0.85 | 1.2E−02 | 51 |
| Control | | 0.57 | | 0.0 |

Table 16: Analyses of root growth rate (relative growth rate of root length and root coverage) of transgenic plants overexpressing the exogenous polynucleotides of some embodiments of the invention (using the cloned or synthetic genes listed in Table 10 above) under the regulation of a constitutive promoter (At6669; SEQ ID NO: 674) when grown under limiting nitrogen conditions [low nitrogen or nitrogen deficient conditions (0.75 mM N)] as compared to control plants. "Incr." = increment with respect to a control plant which has been transformed with an empty vector. Ave. = Average calculated from several transgenic events. "Event #" = number of event (transgenic transformation).

TABLE 17

Transgenic *Arabidopsis* plants exogenously expressing the polynucleotides of some embodiments of the invention under the regulation of the 35S promoter exhibit improved plant biomass and growth rate under nitrogen deficient conditions

| Gene Name | Event # | Ave. | p-value | % incr. |
|---|---|---|---|---|
| Leaf area (cm$^2$) | | | | |
| CTF113 | 5871.2 | 0.70 | 3.6E−02 | 21.6% |
| Control | | 0.58 | | 0.0% |
| CTF163 | 11011.2 | 0.77 | 3.0E−02 | 28.4% |
| Control | | 0.60 | | 0.0% |
| CTF215 | 11072.1 | 0.83 | 1.8E−02 | 27.9% |
| Control | | 0.65 | | 0.0% |
| CTF226 | 10982.1 | 1.16 | 8.3E−04 | 44.1% |
| CTF226 | 10982.3 | 1.10 | 1.6E−02 | 36.4% |
| Control | | 0.80 | | 0.0% |
| CTF180 | 11371.1 | 0.59 | 4.2E−02 | 16.2% |
| Control | | 0.51 | | 0.0% |
| Relative growth rate of Leaf area | | | | |
| CTF163 | 11011.2 | 0.07 | 1.7E−02 | 24 |
| Control | | 0.06 | | 0.00 |
| CTF215 | 11072.1 | 0.08 | 4.6E−02 | 30 |
| Control | | 0.06 | | 0.00 |
| CTF226 | 10982.1 | 0.11 | 1.1E−03 | 47 |
| CTF226 | 10982.3 | 0.11 | 7.9E−03 | 45 |
| Control | | 0.08 | | 0.00 |

Table 17: Analyses of leaf area and leaf area growth rate (relative growth rate of leaf area) of transgenic plants overexpressing the exogenous polynucleotides of some embodiments of the invention (using the cloned or synthetic genes listed in Table 10 above) under the regulation of a constitutive promoter (35S; SEQ ID NO: 675) when grown under limiting nitrogen conditions [low nitrogen or nitrogen deficient conditions (0.75 mM N)] as compared to control plants. "Incr." = increment with respect to a control plant which has been transformed with an empty vector. Ave. = Average calculated from several transgenic events. "Event #" = number of event (transgenic transformation).

TABLE 18

Transgenic *Arabidopsis* plants exogenously expressing the polynucleotides of some embodiments of the invention under the regulation of the At6669 promoter exhibit improved plant biomass and growth rate under nitrogen deficient conditions

| Gene Name | Event # | Ave. | p-value | % incr. |
|---|---|---|---|---|
| Leaf area (cm$^2$) | | | | |
| LAB31 | 11421.5 | 0.79 | 4.9E−04 | 51.0% |
| LAB31 | 11423.4 | 0.69 | 2.4E−03 | 32.1% |
| LAB23 | 11572.6 | 0.93 | 7.0E−04 | 76.7% |
| Control | | 0.52 | | 0.0% |
| LAB11 | 11024.4 | 0.80 | 3.3E−05 | 48.2% |
| Control | | 0.54 | | 0.0% |
| LAB32 | 11163.2 | 0.67 | 5.2E−03 | 17.9% |
| LAB17 | 11534.1 | 0.84 | 8.6E−03 | 48.4% |
| LAB15 | 11642.2 | 0.68 | 5.3E−03 | 20.5% |
| Control | | 0.57 | | 0.0% |
| LAB4 | 11964.2 | 0.52 | 4.0E−02 | 30.3% |
| Control | | 0.40 | | 0.0% |
| LAB20 | 11131.2 | 0.51 | 3.1E−04 | 43.7% |
| LAB9 | 12281.2 | 0.45 | 2.2E−02 | 28.1% |
| Control | | 0.35 | | 0.0% |
| LAB20 | 11131.1 | 0.64 | 4.3E−03 | 46.9% |
| LAB20 | 11134.4 | 0.53 | 2.5E−02 | 23.6% |
| LAB9 | 12284.1 | 0.79 | 1.8E−03 | 83.2% |
| LAB9 | 12286.1 | 0.56 | 4.3E−02 | 29.9% |
| LAB45 | 12365.1 | 0.75 | 2.5E−02 | 72.8% |
| LAB8 | 12425.4 | 0.68 | 5.9E−03 | 56.7% |
| Control | | 0.43 | | 0.0% |
| LAB31 | 11423.4 | 0.60 | 6.8E−04 | 49.2% |
| LAB13 | 11481.5 | 0.57 | 2.1E−02 | 43.5% |
| LAB51 | 11561.2 | 0.55 | 2.5E−02 | 36.9% |
| LAB51 | 11561.5 | 0.55 | 3.3E−02 | 37.4% |
| Control | | 0.40 | | 0.0% |
| LAB20 | 11131.1 | 0.55 | 2.1E−02 | 28.2% |
| LAB49 | 11283.5 | 0.58 | 3.7E−02 | 33.6% |
| LAB5 | 11444.5 | 0.54 | 2.6E−02 | 26.0% |
| Control | | 0.43 | | 0.0% |
| Relative growth rate of leaf area (regression coefficient) | | | | |
| LAB31 | 11421.5 | 0.08 | 1.0E−05 | 53.6% |
| LAB31 | 11423.4 | 0.07 | 2.7E−05 | 45.4% |
| LAB13 | 11482.2 | 0.06 | 2.1E−02 | 23.5% |
| LAB13 | 11484.2 | 0.06 | 1.7E−02 | 25.0% |
| LAB41 | 11551.2 | 0.07 | 2.0E−03 | 34.5% |
| LAB41 | 11554.3 | 0.07 | 9.9E−04 | 49.2% |
| LAB23 | 11572.6 | 0.09 | 0.0E+00 | 86.1% |
| Control | | 0.05 | | 0.0% |
| LAB11 | 11024.4 | 0.08 | 4.4E−03 | 39.2% |
| Control | | 0.06 | | 0.0% |
| LAB25 | 11341.1 | 0.07 | 4.9E−02 | 24.6% |
| LAB17 | 11534.1 | 0.08 | 1.8E−03 | 41.4% |
| Control | | 0.06 | | 0.0% |
| LAB20 | 11131.2 | 0.05 | 1.3E−03 | 37.3% |
| LAB9 | 12281.2 | 0.05 | 1.9E−02 | 27.4% |
| LAB9 | 12284.1 | 0.05 | 2.6E−02 | 48.5% |

TABLE 18-continued

Transgenic *Arabidopsis* plants exogenously expressing the polynucleotides of some embodiments of the invention under the regulation of the At6669 promoter exhibit improved plant biomass and growth rate under nitrogen deficient conditions

| Gene Name | Event # | Ave. | p-value | % incr. |
|---|---|---|---|---|
| LAB9 | 12286.1 | 0.05 | 3.9E−02 | 30.3% |
| LAB45 | 12364.2 | 0.05 | 4.7E−02 | 30.6% |
| Control | | 0.04 | | 0.0% |
| LAB20 | 11131.1 | 0.07 | 5.9E−04 | 47.5% |
| LAB9 | 12284.1 | 0.08 | 1.0E−06 | 83.1% |
| LAB9 | 12286.1 | 0.06 | 1.3E−02 | 32.8% |
| LAB45 | 12361.1 | 0.06 | 4.5E−03 | 44.4% |
| LAB45 | 12365.1 | 0.08 | 3.8E−04 | 69.1% |
| LAB8 | 12422.3 | 0.06 | 2.6E−02 | 37.8% |
| LAB8 | 12425.4 | 0.07 | 8.1E−05 | 58.7% |
| Control | | 0.04 | | 0.0% |
| LAB31 | 11423.4 | 0.06 | 2.7E−02 | 35.4% |
| Control | | 0.04 | | 0.0% |
| LAB49 | 11283.5 | 0.06 | 2.8E−02 | 41.4% |
| Control | | 0.04 | | 0.0% |

Table 18: Analyses of leaf area and leaf area growth rate (leaf area growth rate) of transgenic plants overexpressing the exogenous polynucleotides of some embodiments of the invention (using the cloned or synthetic genes listed in Table 10 above) under the regulation of a constitutive promoter (At6669; SEQ ID NO: 674) when grown under limiting nitrogen conditions [low nitrogen or nitrogen deficient conditions (0.75 mM N)] as compared to control plants. "Incr." = increment with respect to a control plant which has been transformed with an empty vector. Ave. = Average calculated from several transgenic events. "Event #" = number of event (transgenic transformation).

The genes presented in Tables 19-26, hereinbelow, were found to improve plant performance by improving root performance, plant growth characteristic and plant biomass when grown under normal growth conditions, compared to control plants.

Tables 19-26 depict analyses of root growth (root length and root coverage; Tables 19 and 20); plant biomass (plant fresh, dry weight and leaf area; Tables 21 and 22); root growth rate (relative growth rate of root length and root coverage; Tables 23 and 24); leaf area and leaf area growth rate (Relative growth rate of leaf area; Tables 25 and 26) when grown under normal growth conditions (i.e., in the presence of 15 mM nitrogen) in plants overexpressing the polynucleotides of some embodiments of the invention under the regulation of a constitutive promoter [35S (SEQ ID NO:675) or At6669 (SEQ ID NO:674)]. Evaluation of each gene was performed by testing the performance of several events. Some of the genes were evaluated in more than one tissue culture assay and the second experiment confirmed the significant increment in plant biomass. Event with p-value<0.05 was considered statistically significant.

TABLE 19

Transgenic *Arabidopsis* plants exogenously expressing the polynucleotides of some embodiments of the invention under the regulation of the 35S promoter exhibit improved plant roots under normal conditions

| Gene Name | Event # | Ave. | p-value | % incr. |
|---|---|---|---|---|
| | Plant root length [cm] | | | |
| BDL103 | 8033.4 | 5.29 | 7.6E−03 | 14.5% |
| Control | | 4.62 | | 0.0% |
| CTF113 | 5871.3 | 2.51 | 2.7E−02 | 42.3% |
| Control | | 1.76 | | 0.0% |
| CTF163 | 11012.7 | 6.38 | 9.6E−03 | 48.1% |
| Control | | 4.31 | | 0.0% |

TABLE 19-continued

Transgenic *Arabidopsis* plants exogenously expressing the polynucleotides of some embodiments of the invention under the regulation of the 35S promoter exhibit improved plant roots under normal conditions

| Gene Name | Event # | Ave. | p-value | % incr. |
|---|---|---|---|---|
| CTF205 | 11972.3 | 5.26 | 5.5E−03 | 23.4% |
| Control | | 4.26 | | 0.0% |
| | Plant root coverage [cm$^2$] | | | |
| BDL166 | 9985.2 | 7.21 | 3.1E−02 | 67.0% |
| Control | | 4.32 | | 0.0% |
| CTF163 | 11012.7 | 6.41 | 1.6E−02 | 40.2% |
| Control | | 4.58 | | 0.0% |
| CTF205 | 11972.3 | 4.64 | 2.8E−02 | 47.5% |
| Control | | 3.15 | | 0.0% |

Table 19: Analyses of plant roots (root length and root coverage) of transgenic plants overexpressing the exogenous polynucleotides of some embodiments of the invention (using the cloned or synthetic genes listed in Table 10 above) under the regulation of a constitutive promoter (35S; SEQ ID NO: 675) when grown under normal conditions as compared to control plants. "Incr." = increment with respect to a control plant which has been transformed with an empty vector. Ave. = Average calculated from several transgenic events. "Event #" = number of event (transgenic transformation).

TABLE 20

Transgenic *Arabidopsis* plants exogenously expressing the polynucleotides of some embodiments of the invention under the regulation of the At6669 promoter exhibit improved plant roots under normal conditions

| Gene Name | Event # | Ave. | p-value | % incr. |
|---|---|---|---|---|
| | Plant root length [cm] | | | |
| LAB31 | 11421.5 | 6.55 | 1.15E−02 | 21.9% |
| LAB31 | 11423.2 | 6.44 | 4.87E−02 | 20.0% |
| LAB31 | 11423.4 | 6.32 | 4.20E−02 | 17.7% |
| LAB13 | 11482.2 | 6.90 | 2.98E−03 | 28.4% |
| LAB13 | 11484.2 | 6.69 | 3.18E−02 | 24.5% |
| LAB41 | 11551.2 | 6.89 | 2.57E−03 | 28.4% |
| LAB23 | 11572.6 | 6.72 | 4.99E−03 | 25.2% |
| Control | | 5.37 | | 0.0% |
| LAB11 | 11022.1 | 5.79 | 8.49E−03 | 22.2% |
| LAB11 | 11022.3 | 6.25 | 1.42E−03 | 31.9% |
| LAB11 | 11024.4 | 5.87 | 1.96E−02 | 23.9% |
| LAB16 | 11032.2 | 5.84 | 1.06E−02 | 23.4% |
| LAB22 | 11062.3 | 6.09 | 2.15E−03 | 28.6% |
| LAB22 | 11063.4 | 5.66 | 2.93E−02 | 19.6% |
| LAB22 | 11064.6 | 5.78 | 1.99E−02 | 21.9% |
| LAB36 | 11585.5 | 5.77 | 3.64E−03 | 21.8% |
| Control | | 4.74 | | 0.0% |
| LAB32 | 11162.2 | 5.27 | 2.10E−02 | 14.2% |
| LAB32 | 11163.2 | 5.91 | 2.14E−02 | 27.9% |
| LAB34 | 11175.1 | 5.55 | 1.21E−02 | 20.1% |
| LAB33 | 11272.4 | 5.07 | 4.85E−02 | 9.8% |
| LAB25 | 11341.1 | 5.79 | 3.40E−02 | 25.4% |
| LAB15 | 11642.2 | 5.74 | 3.61E−02 | 24.2% |
| LAB15 | 11644.2 | 5.15 | 3.29E−02 | 11.6% |
| Control | | 4.62 | | 0.0% |
| LAB2 | 11234.2 | 5.18 | 4.51E−02 | 20.9% |
| LAB4 | 11962.1 | 5.15 | 2.22E−02 | 20.4% |
| LAB4 | 11963.2 | 4.98 | 1.41E−02 | 16.3% |
| Control | | 4.28 | | 0.0% |
| LAB20 | 11131.1 | 5.52 | 3.31E−02 | 20.6% |
| LAB9 | 12281.2 | 5.22 | 6.31E−03 | 14.1% |
| LAB45 | 12365.1 | 5.84 | 1.27E−03 | 27.6% |
| Control | | 4.58 | | 0.0% |
| LAB45 | 12361.1 | 6.10 | 2.44E−02 | 11.2% |
| LAB8 | 12425.4 | 6.31 | 8.97E−03 | 15.0% |
| Control | | 5.48 | | 0.0% |
| LAB13 | 11482.2 | 5.86 | 4.74E−03 | 21.5% |
| Control | | 4.82 | | 0.0% |
| LAB20 | 11131.2 | 6.81 | 8.98E−04 | 28.8% |
| LAB20 | 11132.7 | 6.58 | 1.90E−02 | 24.6% |
| LAB20 | 11134.4 | 6.12 | 1.60E−02 | 15.8% |
| LAB24 | 11193.5 | 6.10 | 2.51E−03 | 15.6% |
| LAB3 | 11333.1 | 6.45 | 1.02E−02 | 22.2% |

TABLE 20-continued

Transgenic *Arabidopsis* plants exogenously expressing the polynucleotides of some embodiments of the invention under the regulation of the At6669 promoter exhibit improved plant roots under normal conditions

| Gene Name | Event # | Ave. | p-value | % incr. |
|---|---|---|---|---|
| LAB36 | 11584.5 | 6.53 | 3.45E−02 | 23.6% |
| Control |  | 5.28 |  | 0.0% |
| LAB2 | 11234.2 | 5.17 | 0.045 | 7.81% |
| Control |  | 4.80 |  |  |
| Plant root coverage [cm²] | | | | |
| LAB13 | 11482.2 | 8.17 | 1.1E−02 | 62.5% |
| LAB41 | 11551.2 | 6.90 | 2.7E−02 | 37.3% |
| LAB23 | 11572.6 | 7.11 | 9.5E−03 | 41.5% |
| Control |  | 5.03 |  | 0.0% |
| LAB22 | 11062.3 | 5.77 | 7.7E−04 | 55.9% |
| LAB36 | 11585.5 | 5.21 | 6.3E−03 | 40.8% |
| Control |  | 3.70 |  | 0.0% |
| LAB34 | 11175.1 | 5.97 | 6.2E−03 | 50.8% |
| LAB50 | Control | 4.86 |  | 0.0% |
| LAB4 | 11964.2 | 4.70 | 4.1E−02 | 41.8% |
| LAB18 | Control | 3.31 |  | 0.0% |
| LAB4 | 11964.1 | 5.30 | 1.5E−02 | 30.7% |
| Control |  | 4.05 |  | 0.0% |
| LAB9 | 12281.2 | 5.45 | 2.5E−02 | 55.1% |
| LAB45 | 12365.1 | 5.91 | 3.5E−02 | 68.1% |
| Control |  | 3.51 |  | 0.0% |
| LAB9 | 12284.1 | 8.02 | 6.4E−03 | 69.3% |
| LAB45 | 12365.1 | 7.92 | 1.8E−03 | 67.2% |
| LAB8 | 12423.1 | 7.10 | 6.2E−03 | 50.0% |
| LAB8 | 12425.4 | 7.47 | 3.8E−03 | 57.8% |
| Control |  | 4.74 |  | 0.0% |
| LAB49 | 11281.4 | 5.43 | 3.3E−02 | 26.9% |
| Control |  | 4.28 |  | 0.0% |

Table 20: Analyses of plant roots (root length and root coverage) of transgenic plants overexpressing the exogenous polynucleotides of some embodiments of the invention (using the cloned or synthetic genes listed in Table 10 above) under the regulation of a constitutive promoter (At6669; SEQ ID NO: 674) when grown under normal conditions as compared to control plants. "Incr." = increment with respect to a control plant which has been transformed with an empty vector. Ave. = Average calculated from several transgenic events. "Event #" = number of event (transgenic transformation).

TABLE 21

Transgenic *Arabidopsis* plants exogenously expressing the polynucleotides of some embodiments of the invention under the regulation of the 35S promoter exhibit improved plant biomass under normal conditions

| Gene Name | Event # | Ave. | p-value | % incr. |
|---|---|---|---|---|
| Plant Fresh Weight [g] | | | | |
| CTF113 | 5872.1 | 0.15 | 2.1E−02 | 44.4% |
| Control |  | 0.10 |  | 0.0% |
| BDL14 | 5761.2 | 0.24 | 3.3E−02 | 44.5% |
| Control |  | 0.16 |  | 0.0% |
| BDL17 | 6081.3 | 0.30 | 2.9E−02 | 63.5% |
| Control |  | 0.18 |  | 0.0% |
| BDL166 | 9985.2 | 0.29 | 5.9E−03 | 52.2% |
| Control |  | 0.19 |  | 0.0% |
| CTF226 | 10985.1 | 0.19 | 3.1E−02 | 40.0% |
| CTF226 | 10985.5 | 0.17 | 2.2E−02 | 29.7% |
| Control |  | 0.13 |  | 0.0% |
| CTF205 | 11972.3 | 0.11 | 1.2E−02 | 32.1% |
| Control |  | 0.09 |  | 0.0% |
| BDL17 | 6081.3 | 0.20 | 4.7E−03 | 78.5% |
| BDL17 | 6081.5 | 0.20 | 2.2E−02 | 83.1% |
| BDL17 | 6083.2 | 0.21 | 1.0E−04 | 94.9% |
| Control |  | 0.11 |  | 0.0% |
| CTF180 | 11371.1 | 0.11 | 5.7E−04 | 63.2% |
| CTF180 | 11376.1 | 0.09 | 1.3E−02 | 29.5% |
| CTF205 | 11972.3 | 0.10 | 1.6E−02 | 46.2% |

TABLE 21-continued

Transgenic *Arabidopsis* plants exogenously expressing the polynucleotides of some embodiments of the invention under the regulation of the 35S promoter exhibit improved plant biomass under normal conditions

| Gene Name | Event # | Ave. | p-value | % incr. |
|---|---|---|---|---|
| CTF205 | 11973.2 | 0.09 | 3.7E−02 | 35.0% |
| Control |  | 0.07 |  | 0.0% |
| Plant Dry Weight [g] | | | | |
| CTF113 | 5872.1 | 0.0086 | 2.3E−02 | 0.44 |
| Control | Control | 0.0060 |  | 0.00 |
| CTF175 | 8701.4 | 0.0054 | 4.5E−03 | 0.91 |
| CTF175 | 8702.4 | 0.0042 | 4.9E−02 | 0.49 |
| Control | Control | 0.0028 |  | 0.00 |
| BDL103 | 8033.12 | 0.0050 | 8.3E−03 | 0.13 |
| Control | Control | 0.0107 |  | 0.00 |
| BDL166 | 9985.2 | 0.0163 | 8.5E−04 | 0.73 |
| Control | Control | 0.0094 |  | 0.00 |
| CTF215 | 11072.1 | 0.0080 | 2.6E−02 | 0.29 |
| Control | Control | 0.0062 |  | 0.00 |
| CTF226 | 10982.1 | 0.0097 | 2.5E−03 | 0.69 |
| CTF226 | 10985.1 | 0.0081 | 1.5E−02 | 0.42 |
| Control | Control | 0.0057 |  | 0.00 |
| CTF205 | 11972.3 | 0.0053 | 5.0E−03 | 0.20 |
| Control | Control | 0.0044 |  | 0.00 |
| BDL17 | 6081.3 | 0.0088 | 4.0E−02 | 0.49 |
| BDL17 | 6083.2 | 0.0106 | 2.1E−02 | 0.79 |
| Control | Control | 0.0059 |  | 0.00 |
| CTF180 | 11371.1 | 0.0044 | 5.0E−02 | 0.49 |
| CTF180 | 11376.1 | 0.0038 | 4.0E−02 | 0.28 |
| Control | Control | 0.0030 |  | 0.00 |

Table 21: Analyses of plant Biomass (fresh weight and dry weight) of transgenic plants overexpressing the exogenous polynucleotides of some embodiments of the invention (using the cloned or synthetic genes listed in Table 10 above) under the regulation of a constitutive promoter (35S; SEQ ID NO: 675) when grown under normal conditions as compared to control plants. "Incr." = increment with respect to a control plant which has been transformed with an empty vector. Ave. = Average calculated from several transgenic events. "Event #" = number of event (transgenic transformation).

TABLE 22

Transgenic *Arabidopsis* plants exogenously expressing the polynucleotides of some embodiments of the invention under the regulation of the At6669 promoter exhibit improved plant biomass under normal conditions

| Gene Name | Event # | Ave. | p-value | % incr. |
|---|---|---|---|---|
| Plant Fresh Weight [g] | | | | |
| LAB23 | 11572.6 | 0.129 | 4.2E−02 | 31.2% |
| Control |  | 0.098 |  | 0.0% |
| LAB11 | 11022.1 | 0.102 | 3.2E−03 | 43.8% |
| LAB11 | 11022.3 | 0.099 | 5.7E−03 | 39.2% |
| LAB16 | 11032.2 | 0.126 | 1.5E−02 | 77.4% |
| LAB16 | 11033.2 | 0.098 | 2.1E−02 | 37.9% |
| LAB22 | 11064.6 | 0.125 | 3.7E−02 | 75.7% |
| LAB36 | 11585.5 | 0.091 | 1.7E−02 | 27.3% |
| Control |  | 0.071 |  | 0.0% |
| LAB32 | 11163.2 | 0.116 | 8.2E−03 | 39.8% |
| LAB33 | 11272.2 | 0.120 | 6.0E−03 | 43.7% |
| LAB17 | 11534.1 | 0.110 | 4.6E−02 | 31.9% |
| LAB15 | 11642.2 | 0.154 | 2.8E−02 | 85.2% |
| Control |  | 0.083 |  | 0.0% |
| LAB18 | 11653.7 | 0.076 | 3.3E−02 | 26.9% |
| Control |  | 0.060 |  | 0.0% |
| LAB20 | 11131.2 | 0.167 | 1.4E−04 | 146.4% |
| LAB20 | 11134.4 | 0.095 | 2.1E−02 | 40.7% |
| LAB9 | 12284.1 | 0.133 | 4.7E−02 | 95.8% |
| Control |  | 0.068 |  | 0.0% |
| LAB32 | 11163.1 | 0.089 | 3.8E−03 | 40.3% |
| LAB31 | 11422.5 | 0.099 | 1.4E−02 | 55.8% |
| LAB31 | 11423.1 | 0.106 | 8.6E−03 | 66.6% |
| LAB13 | 11481.5 | 0.102 | 8.7E−05 | 60.6% |
| LAB13 | 11482.2 | 0.106 | 2.2E−02 | 65.9% |
| LAB13 | 11483.2 | 0.114 | 4.3E−02 | 79.4% |
| LAB13 | 11483.3 | 0.081 | 4.5E−02 | 27.2% |

TABLE 22-continued

Transgenic *Arabidopsis* plants exogenously expressing the polynucleotides of some embodiments of the invention under the regulation of the At6669 promoter exhibit improved plant biomass under normal conditions

| Gene Name | Event # | Ave. | p-value | % incr. |
|---|---|---|---|---|
| LAB13 | 11484.2 | 0.127 | 5.0E−04 | 99.6% |
| LAB51 | 11561.2 | 0.107 | 8.1E−03 | 67.3% |
| LAB51 | 11561.5 | 0.135 | 2.7E−02 | 112.1% |
| LAB51 | 11564.7 | 0.119 | 3.3E−02 | 86.9% |
| LAB8 | 12422.3 | 0.079 | 3.6E−02 | 24.1% |
| LAB8 | 12423.3 | 0.081 | 2.5E−02 | 27.5% |
| Control | | 0.064 | | 0.0% |
| LAB3 | 11333.5 | 0.128 | 1.6E−03 | 53.0% |
| Control | | 0.084 | | 0.0% |
| Plant Dry Weight [g] | | | | |
| LAB23 | 11571.5 | 0.0057 | 1.0E−02 | 0.30 |
| LAB23 | 11572.6 | 0.0062 | 1.1E−03 | 0.43 |
| Control | Control | 0.0044 | | 0.00 |
| LAB11 | 11022.1 | 0.0045 | 3.4E−02 | 0.53 |
| LAB11 | 11023.4 | 0.0035 | 4.9E−02 | 0.18 |
| LAB11 | 11024.4 | 0.0044 | 3.6E−02 | 0.52 |
| LAB22 | 11064.6 | 0.0055 | 1.4E−02 | 0.89 |
| LAB36 | 11584.2 | 0.0042 | 3.7E−02 | 0.43 |
| LAB36 | 11584.5 | 0.0036 | 8.8E−03 | 0.24 |
| Control | Control | 0.0029 | | 0.00 |
| LAB32 | 11163.2 | 0.0057 | 1.9E−02 | 0.40 |
| LAB33 | 11272.2 | 0.0051 | 1.9E−02 | 0.25 |
| LAB15 | Control | 0.0041 | | 0.00 |
| LAB18 | 11653.7 | 0.0037 | 2.7E−02 | 0.24 |
| Control | Control | 0.0030 | | 0.00 |
| LAB20 | 11131.2 | 0.0063 | 3.8E−02 | 1.24 |
| LAB9 | 12282.2 | 0.0039 | 2.4E−02 | 0.37 |
| LAB9 | 12284.1 | 0.0057 | 4.2E−02 | 1.01 |
| LAB45 | 12365.1 | 0.0047 | 2.6E−02 | 0.66 |
| Control | Control | 0.0028 | | 0.00 |
| LAB9 | 12281.2 | 0.0063 | 2.2E−02 | 0.30 |
| LAB9 | 12284.1 | 0.0077 | 1.5E−03 | 0.58 |
| Control | Control | 0.0049 | | 0.00 |
| LAB32 | 11163.1 | 0.0046 | 9.9E−04 | 0.67 |
| LAB31 | 11422.1 | 0.0041 | 2.5E−02 | 0.48 |
| LAB31 | 11423.1 | 0.0050 | 4.3E−02 | 0.82 |
| LAB31 | 11423.4 | 0.0053 | 3.5E−02 | 0.91 |
| LAB13 | 11483.2 | 0.0051 | 3.2E−02 | 0.85 |
| LAB13 | 11484.2 | 0.0063 | 8.4E−03 | 1.27 |
| LAB51 | 11561.2 | 0.0039 | 3.5E−02 | 0.42 |
| Control | Control | 0.0028 | | 0.00 |
| LAB24 | 11193.6 | 0.0041 | 6.2E−03 | 0.44 |
| LAB3 | 11334.1 | 0.0042 | 3.4E−03 | 0.47 |
| LAB5 | 11443.4 | 0.0039 | 4.8E−03 | 0.36 |
| LAB5 | 11444.5 | 0.0044 | 1.7E−02 | 0.54 |
| LAB36 | 11583.1 | 0.0044 | 9.1E−04 | 0.57 |
| Control | .5 | 0.0028 | | 0.00 |

Table 22: Analyses of plant biomass (fresh weight and dry weight) of transgenic plants overexpressing the exogenous polynucleotides of some embodiments of the invention (using the cloned or synthetic genes listed in Table 10 above) under the regulation of a constitutive promoter (At6669; SEQ ID NO: 674) when grown under normal conditions as compared to control plants. "Incr." = increment with respect to a control plant which has been transformed with an empty vector. Ave. = Average calculated from several transgenic events. "Event #" = number of event (transgenic transformation).

TABLE 23

Transgenic *Arabidopsis* plants exogenously expressing the polynucleotides of some embodiments of the invention under the regulation of the 35S promoter exhibit improved plant biomass and growth rate under normal conditions

| Gene Name | Event # | Ave. | p-value | % incr. |
|---|---|---|---|---|
| Relative growth rate of root length (regression coefficient) | | | | |
| BDL103 | 8033.4 | 0.509 | 2.23E−02 | 21.9% |
| Control | | 0.418 | | 0.0% |
| CTF113 | 5871.3 | 0.192 | 3.31E−02 | 49.6% |
| Control | | 0.128 | | 0.0% |
| BDL210 | 10831.5 | 0.356 | 3.29E−02 | 36.5% |
| Control | | 0.261 | | 0.0% |
| CTF163 | 11012.7 | 0.604 | 8.70E−05 | 64.9% |
| Control | | 0.366 | | 0.0% |
| Relative growth rate of root coverage (regression coefficient) | | | | |
| CTF113 | 5871.3 | 0.27 | 2.3E−03 | 165.9% |
| Control | | 0.10 | | 0.0% |
| BDL210 | 10831.5 | 0.42 | 4.9E−02 | 54.4% |
| Control | | 0.27 | | 0.0% |
| BDL166 | 9985.2 | 0.83 | 1.2E−02 | 62.4% |
| Control | | 0.51 | | 0.0% |
| CTF163 | 11012.7 | 0.75 | 4.0E−03 | 42.6% |
| Control | | 0.53 | | 0.0% |
| BDL17 | 60815 | 1.12 | 3.2E−02 | 52.6% |
| Control | | 0.74 | | 0.0% |
| CTF205 | 11972.3 | 0.50 | 1.0E−02 | 38.7% |
| Control | | 0.36 | | 0.0% |

Table 23: Analyses of root growth rate (relative growth rate of root length and root coverage) of transgenic plants overexpressing the exogenous polynucleotides of some embodiments of the invention (using the cloned or synthetic genes listed in Table 10 above) under the regulation of a constitutive promoter (35S; SEQ ID NO: 675) when grown under normal conditions as compared to control plants. "Incr." = increment with respect to a control plant which has been transformed with an empty vector. Ave. = Average calculated from several transgenic events. "Event #" = number of event (transgenic transformation).

TABLE 24

Transgenic *Arabidopsis* plants exogenously expressing the polynucleotides of some embodiments of the invention under the regulation of the At6669 promoter exhibit improved plant biomass and growth rate under normal conditions

| Gene Name | Event # | Ave. | p-value | % incr. |
|---|---|---|---|---|
| Relative Growth Rate of Root Length (Regression coefficient) | | | | |
| LAB13 | 11482.2 | 0.594 | 1.86E−02 | 38.3% |
| LAB41 | 11551.2 | 0.618 | 6.18E−03 | 43.8% |
| Control | | 0.430 | | 0.0% |
| LAB22 | 11062.3 | 0.498 | 1.22E−02 | 31.6% |
| LAB36 | 11585.5 | 0.487 | 1.84E−02 | 28.8% |
| Control | | 0.378 | | 0.0% |
| LAB21 | 11144.1 | 0.423 | 2.99E−02 | 25.1% |
| LAB32 | 11162.2 | 0.412 | 3.64E−02 | 21.9% |
| LAB32 | 11163.2 | 0.455 | 1.59E−02 | 34.7% |
| LAB34 | 11175.1 | 0.432 | 1.57E−02 | 27.8% |
| LAB25 | 11341.1 | 0.457 | 8.49E−03 | 35.1% |
| LAB25 | 11342.2 | 0.464 | 3.22E−02 | 37.3% |
| LAB38 | 11434.4 | 0.431 | 2.27E−02 | 27.6% |
| LAB15 | 11641.1 | 0.480 | 2.38E−03 | 42.0% |
| LAB15 | 11642.2 | 0.464 | 7.31E−03 | 37.3% |
| Control | | 0.338 | | 0.0% |
| LAB2 | 11231.1 | 0.430 | 4.51E−02 | 24.2% |
| LAB4 | 11962.1 | 0.439 | 1.79E−02 | 26.6% |
| LAB4 | 11964.2 | 0.480 | 5.38E−03 | 38.6% |
| Control | | 0.346 | | 0.0% |
| LAB20 | 11131.1 | 0.476 | 3.64E−03 | 32.5% |
| LAB45 | 12364.2 | 0.439 | 4.72E−02 | 22.2% |
| LAB45 | 12365.1 | 0.462 | 5.73E−03 | 28.6% |
| Control | | 0.359 | | 0.0% |
| LAB13 | 11482.2 | 0.505 | 2.79E−02 | 26.0% |
| Control | | 0.401 | | 0.0% |
| LAB20 | 11131.2 | 0.543 | 1.00E−05 | 40.0% |
| LAB20 | 11132.7 | 0.527 | 1.08E−03 | 35.9% |
| LAB49 | 11281.4 | 0.482 | 3.02E−02 | 24.3% |
| LAB3 | 11333.1 | 0.519 | 4.80E−04 | 33.7% |
| LAB5 | 11444.1 | 0.470 | 9.27E−03 | 21.3% |
| LAB36 | 11584.2 | 0.485 | 1.39E−02 | 25.0% |
| LAB36 | 11584.5 | 0.546 | 2.23E−04 | 40.7% |

TABLE 24-continued

Transgenic *Arabidopsis* plants exogenously expressing the polynucleotides of some embodiments of the invention under the regulation of the At6669 promoter exhibit improved plant biomass and growth rate under normal conditions

| Gene Name | Event # | Ave. | p-value | % incr. |
|---|---|---|---|---|
| Control | | 0.388 | | 0.0% |
| LAB2 | 11231.1 | 0.43 | 0.04 | |
| Control | | 0.35 | | 20.16% |

Relative Growth Rate of Root Coverage (Regression coefficient)

| Gene Name | Event # | Ave. | p-value | % incr. |
|---|---|---|---|---|
| LAB31 | 11423.4 | 0.83 | 1.6E-02 | 52.0% |
| LAB13 | 11482.2 | 0.97 | 4.6E-04 | 79.0% |
| LAB13 | 11484.2 | 0.79 | 2.6E-02 | 45.1% |
| LAB41 | 11551.2 | 0.80 | 1.7E-02 | 47.3% |
| LAB41 | 11552.4 | 0.77 | 4.7E-02 | 42.4% |
| LAB41 | 11554.3 | 0.94 | 4.9E-03 | 73.6% |
| LAB23 | 11572.6 | 0.82 | 7.6E-03 | 51.2% |
| Control | | 0.54 | | 0.0% |
| LAB11 | 11022.1 | 0.59 | 1.7E-02 | 45.8% |
| LAB11 | 11022.3 | 0.58 | 1.4E-02 | 42.6% |
| LAB16 | 11032.3 | 0.56 | 2.1E-02 | 38.3% |
| LAB22 | 11062.3 | 0.67 | 2.1E-04 | 65.5% |
| LAB36 | 11585.5 | 0.59 | 6.3E-03 | 45.2% |
| Control | | 0.41 | | 0.0% |
| LAB32 | 11163.2 | 0.60 | 6.9E-03 | 46.9% |
| LAB34 | 11175.1 | 0.64 | 8.6E-04 | 56.7% |
| LAB25 | 11341.1 | 0.55 | 3.7E-02 | 34.9% |
| LAB25 | 11342.2 | 0.59 | 3.3E-02 | 44.3% |
| LAB17 | 11533.7 | 0.57 | 4.9E-02 | 39.4% |
| LAB15 | 11642.2 | 0.73 | 1.5E-03 | 78.2% |
| LAB15 | 11644.1 | 0.58 | 2.1E-02 | 41.2% |
| LAB15 | 11644.2 | 0.58 | 1.4E-02 | 42.7% |
| Control | | 0.41 | | 0.0% |
| LAB4 | 11964.2 | 0.55 | 3.0E-03 | 48.5% |
| Control | | 0.37 | | 0.0% |
| LAB2 | 11231.1 | 0.58 | 2.6E-02 | 39.5% |
| LAB4 | 11963.2 | 0.65 | 4.0E-02 | 54.6% |
| LAB4 | 11964.1 | 0.58 | 1.8E-02 | 37.8% |
| Control | | 0.42 | | 0.0% |
| LAB20 | 11131.1 | 0.49 | 3.3E-02 | 26.5% |
| LAB20 | 11131.2 | 0.55 | 2.9E-02 | 41.2% |
| LAB9 | 12281.2 | 0.60 | 4.2E-04 | 55.9% |
| LAB45 | 12361.2 | 0.62 | 7.1E-03 | 61.2% |
| LAB45 | 12364.2 | 0.54 | 8.5E-03 | 39.6% |
| LAB45 | 12365.1 | 0.63 | 8.7E-04 | 63.0% |
| Control | | 0.39 | | 0.0% |
| LAB9 | 12284.1 | 0.89 | 9.8E-04 | 68.3% |
| LAB45 | 12361.2 | 0.75 | 2.9E-02 | 42.1% |
| LAB45 | 12365.1 | 0.91 | 2.0E-04 | 71.0% |
| LAB8 | 12423.1 | 0.80 | 5.6E-03 | 50.6% |
| LAB8 | 12425.4 | 0.81 | 3.3E-03 | 53.1% |
| Control | | 0.53 | | 0.0% |
| LAB13 | 11482.2 | 0.56 | 2.5E-02 | 47.4% |
| LAB51 | 11561.5 | 0.63 | 1.3E-02 | 64.1% |
| Control | | 0.38 | | 0.0% |
| LAB20 | 11131.2 | 0.58 | 4.1E-02 | 27.6% |
| LAB20 | 11132.7 | 0.61 | 2.1E-02 | 32.9% |
| LAB49 | 11281.4 | 0.59 | 1.9E-02 | 28.8% |
| Control | | 0.46 | | 0.0% |
| LAB2 | 11231.1 | 0.58 | 0.025 | 39.5% |
| Control | | 0.41 | | |

Table 24: Analyses of root growth rate (relative growth rate of root length and root coverage) of transgenic plants overexpressing the exogenous polynucleotides of some embodiments of the invention (using the cloned or synthetic genes listed in Table 10 above) under the regulation of a constitutive promoter (At6669; SEQ ID NO: 674) when grown under normal conditions as compared to control plants. "Incr." = increment with respect to a control plant which has been transformed with an empty vector. Ave. = Average calculated from several transgenic events. "Event " = number of event (transgenic transformation).

TABLE 25

Transgenic *Arabidopsis* plants exogenously expressing the polynucleotides of some embodiments of the invention under the regulation of the 35S promoter exhibit improved plant biomass and growth rate under normal conditions

| Gene Name | Event # | Average | p-value | % incr. |
|---|---|---|---|---|
| Leaf area (cm²) | | | | |
| BDL17 | 6081.3 | 0.80 | 3.7E-03 | 35.7% |
| Control | | 0.59 | | 0.0% |
| BDL103 | 8033.1 | 0.82 | 8.7E-03 | 39.5% |
| BDL103 | 8033.12 | 0.66 | 9.7E-04 | 12.3% |
| Control | | 1.16 | | 0.0% |
| BDL166 | 9985.2 | 1.13 | 1.6E-03 | 40.7% |
| Control | | 0.80 | | 0.0% |
| CTF226 | 10982.1 | 1.24 | 2.3E-02 | 37.6% |
| Control | | 0.90 | | 0.0% |
| BDL17 | 6081.3 | 1.21 | 3.8E-03 | 54.7% |
| BDL17 | 6081.5 | 1.17 | 1.0E-02 | 50.0% |
| BDL17 | 6083.2 | 1.20 | 7.1E-03 | 54.0% |
| Control | | 0.78 | | 0.0% |
| CTF180 | 11371.1 | 0.52 | 2.8E-02 | 39.5% |
| CTF180 | 11376.1 | 0.48 | 8.0E-03 | 27.8% |
| CTF205 | 11973.2 | 0.53 | 2.1E-02 | 41.3% |
| Control | | 0.38 | | 0.0% |
| Relative growth rate of leaf area (regression coefficient) | | | | |
| CTF113 | 5873.3 | 0.06 | 1.5E-02 | 46.6% |
| Control | | 0.04 | | 0.0% |
| BDL17 | 6081.3 | 0.08 | 3.7E-02 | 34.6% |
| Control | | 0.06 | | 0.0% |
| BDL103 | 8033.1 | 0.09 | 3.2E-02 | 38.2% |
| BDL103 | 8033.12 | 0.07 | 2.5E-03 | 8.1% |
| Control | | 0.13 | | 0.0% |
| BDL166 | 9985.2 | 0.11 | 4.8E-03 | 41.5% |
| Control | | 0.08 | | 0.0% |
| CTF215 | 11072.1 | 0.09 | 3.3E-02 | 34.4% |
| Control | | 0.07 | | 0.0% |
| CTF205 | 11972.3 | 0.06 | 3.7E-02 | 25.3% |
| Control | | 0.05 | | 0.0% |
| BDL17 | 6081.3 | 0.11 | 2.2E-02 | 43.1% |
| BDL17 | 6081.5 | 0.12 | 1.5E-02 | 46.9% |
| BDL17 | 6083.2 | 0.12 | 2.8E-03 | 59.2% |
| Control | | 0.08 | | 0.0% |
| CTF180 | 11371.1 | 0.05 | 1.1E-02 | 39.3% |
| CTF180 | 11376.1 | 0.05 | 4.0E-02 | 28.6% |
| CTF205 | 11973.2 | 0.05 | 4.5E-03 | 44.8% |
| Control | | 0.04 | | 0.0% |

Table 25: Analyses of leaf area and leaf area growth rate (leaf area growth rate) of transgenic plants overexpressing the exogenous polynucleotides of some embodiments of the invention (using the cloned or synthetic genes listed in Table 10 above) under the regulation of a constitutive promoter (35S; SEQ ID NO: 675) when grown under normal conditions as compared to control plants. "Incr." = increment with respect to a control plant which has been transformed with an empty vector. Ave. = Average calculated from several transgenic events. "Event #" = number of event (transgenic transformation).

TABLE 26

Transgenic *Arabidopsis* plants exogenously expressing the polynucleotides of some embodiments of the invention under the regulation of the At6669 promoter exhibit improved plant biomass and growth rate under normal conditions

| Gene Name | Event # | Average | p-value | % incr. |
|---|---|---|---|---|
| Leaf area (cm²) | | | | |
| LAB41 | 11554.3 | 0.66 | 4.8E-02 | 29.3% |
| LAB23 | 11572.6 | 0.76 | 1.9E-02 | 47.9% |
| Control | | 0.51 | | 0.0% |
| LAB11 | 11022.3 | 0.60 | 5.0E-03 | 31.9% |
| LAB11 | 11024.4 | 0.69 | 2.8E-04 | 50.7% |
| LAB16 | 11032.2 | 0.62 | 4.4E-02 | 36.7% |
| LAB22 | 11064.6 | 0.63 | 1.9E-02 | 38.5% |
| LAB36 | 11584.2 | 0.61 | 2.2E-02 | 33.9% |
| Control | | 0.46 | | 0.0% |
| LAB33 | 11272.2 | 0.65 | 1.2E-02 | 32.4% |

TABLE 26-continued

Transgenic Arabidopsis plants exogenously expressing the polynucleotides of some embodiments of the invention under the regulation of the At6669 promoter exhibit improved plant biomass and growth rate under normal conditions

| Gene Name | Event # | Average | p-value | % incr. |
|---|---|---|---|---|
| LAB25 | 11341.2 | 0.64 | 3.8E−02 | 30.4% |
| LAB17 | 11534.1 | 0.70 | 8.2E−05 | 42.1% |
| LAB15 | 11642.2 | 0.82 | 4.6E−02 | 67.1% |
| Control |  | 0.49 |  | 0.0% |
| LAB20 | 11131.2 | 0.58 | 2.0E−02 | 88.7% |
| LAB9 | 12284.1 | 0.51 | 3.3E−02 | 65.6% |
| LAB45 | 12361.1 | 0.44 | 1.8E−03 | 45.1% |
| Control |  | 0.31 |  | 0.0% |
| LAB9 | 12284.1 | 0.85 | 1.3E−02 | 78.6% |
| LAB45 | 12365.1 | 0.83 | 1.3E−04 | 74.9% |
| LAB8 | 12423.1 | 0.62 | 2.9E−02 | 31.4% |
| Control |  | 0.48 |  | 0.0% |
| LAB32 | 11163.1 | 0.41 | 4.0E−02 | 26.3% |
| LAB31 | 11422.5 | 0.40 | 3.4E−02 | 25.1% |
| LAB31 | 11423.1 | 0.48 | 4.0E−02 | 49.2% |
| LAB31 | 11423.4 | 0.55 | 3.3E−02 | 69.4% |
| LAB13 | 11481.5 | 0.54 | 4.3E−03 | 68.2% |
| LAB13 | 11482.2 | 0.43 | 1.5E−02 | 34.7% |
| LAB13 | 11483.2 | 0.58 | 3.3E−03 | 80.1% |
| LAB13 | 11484.2 | 0.69 | 1.8E−02 | 114.1% |
| LAB51 | 11561.2 | 0.45 | 1.5E−02 | 41.2% |
| LAB51 | 11561.5 | 0.58 | 3.4E−02 | 81.4% |
| LAB51 | 11563.2 | 0.42 | 1.2E−02 | 31.4% |
| LAB51 | 11564.5 | 0.48 | 3.1E−02 | 47.9% |
| LAB51 | 11564.7 | 0.53 | 1.0E−02 | 63.2% |
| LAB8 | 12422.3 | 0.42 | 2.9E−02 | 31.9% |
| LAB8 | 12423.1 | 0.40 | 4.7E−02 | 25.5% |
| Control |  | 0.32 |  | 0.0% |
| LAB20 | 11132.1 | 0.47 | 2.2E−02 | 19.9% |
| LAB49 | 11281.4 | 0.50 | 2.4E−03 | 30.1% |
| LAB3 | 11333.5 | 0.50 | 1.0E−03 | 28.8% |
| LAB5 | 11444.5 | 0.58 | 1.3E−02 | 49.4% |
| LAB36 | 11583.1 | 0.47 | 1.8E−02 | 21.6% |
| LAB36 | 11585.5 | 0.48 | 7.4E−03 | 22.9% |
| Control |  | 0.39 |  | 0.0% |
| Relative growth rate of leaf area | | | | |
| LAB31 | 11421.5 | 0.08 | 1.0E−05 | 53.6% |
| LAB31 | 11423.4 | 0.07 | 2.7E−05 | 45.4% |
| LAB13 | 11482.2 | 0.06 | 2.1E−02 | 23.5% |
| LAB13 | 11484.2 | 0.06 | 1.7E−02 | 25.0% |
| LAB41 | 11551.2 | 0.07 | 2.0E−03 | 34.5% |
| LAB41 | 11554.3 | 0.07 | 9.9E−04 | 49.2% |
| LAB23 | 11572.6 | 0.09 | 0.0E+00 | 86.1% |
| Control |  | 0.05 |  | 0.0% |
| LAB11 | 11024.4 | 0.08 | 4.4E−03 | 39.2% |
| Control |  | 0.06 |  | 0.0% |
| LAB25 | 11341.1 | 0.07 | 4.9E−02 | 24.6% |
| LAB17 | 11534.1 | 0.08 | 1.8E−03 | 41.4% |
| Control |  | 0.06 |  | 0.0% |
| LAB20 | 11131.2 | 0.05 | 1.3E−03 | 37.3% |
| LAB9 | 12281.2 | 0.05 | 1.9E−02 | 27.4% |
| LAB9 | 12284.1 | 0.05 | 2.6E−02 | 48.5% |
| LAB9 | 12286.1 | 0.05 | 3.9E−02 | 30.3% |
| LAB45 | 12364.2 | 0.05 | 4.7E−02 | 30.6% |
| Control |  | 0.04 |  | 0.0% |
| LAB20 | 11131.1 | 0.07 | 5.9E−04 | 47.5% |
| LAB9 | 12284.1 | 0.08 | 1.0E−06 | 83.1% |
| LAB9 | 12286.1 | 0.06 | 1.3E−02 | 32.8% |
| LAB45 | 12361.1 | 0.06 | 4.5E−03 | 44.4% |
| LAB45 | 12365.1 | 0.08 | 3.8E−04 | 69.1% |
| LAB8 | 12422.3 | 0.06 | 2.6E−02 | 37.8% |
| LAB8 | 12425.4 | 0.07 | 8.1E−05 | 58.7% |
| Control |  | 0.04 |  | 0.0% |
| LAB31 | 11423.4 | 0.06 | 2.7E−02 | 35.4% |
| Control |  | 0.04 |  | 0.0% |
| LAB49 | 11283.5 | 0.06 | 2.8E−02 | 41.4% |
| Control |  | 0.04 |  | 0.0% |

Table 26: Analyses of leaf area and leaf area growth rate (leaf area growth rate) of transgenic plants overexpressing the exogenous polynucleotides of some embodiments of the invention (using the cloned or synthetic genes listed in Table 10 above) under the regulation of a constitutive promoter (At6669; SEQ ID NO: 674) when grown under normal conditions as compared to control plants. "Incr." = increment with respect to a control plant which has been transformed with an empty vector. Ave. = Average calculated from several transgenic events. "Event #" = number of event (transgenic transformation).

Example 7

Evaluation of Transgenic Arabidopsis Plant Growth Under Abiotic Stress as Well as Under Favorable Conditions in Greenhouse Assay Grown Until Seed Production ABS Tolerance: Yield and Plant Growth Rate at High Salinity Concentration Under Greenhouse Conditions This assay follows the rosette area growth of plants grown in the greenhouse as well as seed yield at high salinity irrigation. Seeds were sown in agar media supplemented only with a selection agent (Kanamycin) and Hoagland solution under nursery conditions. The T2 transgenic seedlings were then transplanted to 1.7 trays filled with peat and perlite. The trays were irrigated with tap water (provided from the pots' bottom). Half of the plants were irrigated with a salt solution (40-80 mM NaCl and 5 mM $CaCl_2$) so as to induce salinity stress (stress conditions). The other half of the plants was irrigated with tap water (normal conditions). All plants were grown in the greenhouse until mature seeds, then harvested (the above ground tissue) and weighted (immediately or following drying in oven at 50° C. for 24 hours). High salinity conditions were achieved by irrigating with a solution containing 40-80 mM NaCl ("ABS" growth conditions) and compared to regular growth conditions.

Each construct was validated at its T2 generation. Transgenic plants transformed with a construct including the uidA reporter gene (GUS) under the At6669 promoter (SEQ ID NO:674) or with an empty vector including the At6669 promoter are used as control.

The plants were analyzed for their overall size, growth rate, flowering, seed yield, weight of 1,000 seeds, dry matter and harvest index (HI—seed yield/dry matter). Transgenic plants performance was compared to control plants grown in parallel under the same conditions. Mock-transgenic plants expressing the uidA reporter gene (GUS-Intron) or with no gene at all (empty vector, containing the Kan selection gene), under the same promoter were used as control.

The experiments were planned in nested randomized plot distribution. For each gene of the invention three to five independent transformation events were analyzed from each construct.

Digital Imaging

A laboratory image acquisition system, which consists of a digital reflex camera (Canon EOS 300D) attached with a 55 mm focal length lens (Canon EF-S series), mounted on a reproduction device (Kaiser RS), which included 4 light units (4×150 Watts light bulb) was used for capturing images of plant samples.

The image capturing process was repeated every 2 days starting from day 1 after transplanting till day 16. Same camera, placed in a custom made iron mount, was used for capturing images of larger plants sawn in white tubs in an environmental controlled greenhouse. The tubs were square shape and include 1.7 liter trays. During the capture process, the tubs were placed beneath the iron mount, while avoiding direct sun light and casting of shadows.

An image analysis system was used, which consists of a personal desktop computer (Intel P4 3.0 GHz processor) and a public domain program—ImageJ 1.39 (Java based image processing program which was developed at the U.S. National Institutes of Health and freely available on the internet at Hypertext Transfer Protocol://rsbweb (dot) nih (dot) gov/). Images were captured in resolution of 10 Mega Pixels (3888×2592 pixels) and stored in a low compression JPEG (Joint Photographic Experts Group standard) format. Next, analyzed data was saved to text files and processed using the JMP statistical analysis software (SAS institute).

Leaf Growth Analysis

Using the digital analysis leaves data was calculated, including leaf number, rosette area, rosette diameter, leaf blade area, plot coverage, leaf petiole length.

Vegetative Growth Rate: is the Rate of Growth of the Plant as Defined by Formulas VIII, IX, XI and XI Relative growth rate of leaf blade area=Regression coefficient of leaf area along time course.  Formula VIII Relative growth rate of rosette area=Regression coefficient of rosette area along time course.  Formula IX Relative growth rate of rosette diameter=Regression coefficient of rosette diameter along time course.  Formula X Relative growth rate of plot coverage=Regression coefficient of plot coverage along time course.  Formula XI Seeds Average Weight (Seed Weight or 1000 Seed Weight)

At the end of the experiment all seeds were collected. The seeds were scattered on a glass tray and a picture was taken. Using the digital analysis, the number of seeds in each sample was calculated.

Plant Dry Weight and Seed Yield

On about day 80 from sowing, the plants were harvested and left to dry at 30° C. in a drying chamber. The biomass and seed weight of each plot were measured and divided by the number of plants in each plot.

Dry weight=total weight of the vegetative portion above ground (excluding roots) after drying at 30° C. in a drying chamber;

Seed yield per plant=total seed weight per plant (grams).

The Harvest Index can be calculated using Formula IV (as described above; Harvest Index=Average seed yield per plant/Average dry weight).

Statistical Analyses

To identify genes conferring significantly improved ABST, nitrogen use efficiency, growth rate, biomass, oil content and yield production, the results obtained from the transgenic plants were compared to those obtained from control plants. To identify outperforming genes and constructs, results from the independent transformation events tested were analyzed separately. Data was analyzed using Student's t-test and results were considered significant if the p value was less than 0.1. The JMP statistics software package was used (Version 5.2.1, SAS Institute Inc., Cary, N.C., USA).

Experiment Results:

The genes presented in Tables 27-31, hereinbelow, have improved plant ABST when grown at high salinity irrigation levels (80-100 mM NaCl). These genes produced higher seed yield, harvest index, seed weight (expressed as 1000-seed weight) and plant biomass [(as expressed as plant dry weight (DW)] when grown under high salinity irrigation conditions, compared to control.

Tables 27-29 depict analyses of seed yield and weight (Table 27), harvest index (Table 28) and dry weight (Table 29) when grown under high salinity irrigation conditions in plants overexpressing the polynucleotides of some embodiments of the invention under the regulation of a constitutive (35S; SEQ ID NO:675). Evaluation of each gene was performed by testing the performance of several events. Some of the genes were evaluated in more than one tissue culture assay and the results obtained were repeated. Event with p-value<0.05 was considered statistically significant.

TABLE 27

Transgenic *Arabidopsis* plants exogenously expressing the polynucleotides of some embodiments of the invention under the regulation of the 35S promoter exhibit improved seed yield and weight under high salinity irrigation growth conditions

| Gene Name | Event # | Ave. | p-value | % incr. |
|---|---|---|---|---|
| Seed yield | | | | |
| CTF113 | 5871.2 | 0.03 | 3.0E−03 | 75.5% |
| Control | | 0.02 | | 0.0% |
| Seeds weight (g) | | | | |
| CTF113 | 5873.3 | 0.024 | 4.2E−02 | 13.5% |
| Control | | 0.021 | | 0.0% |

Table 27: Analyses of seed yield and weight [expressed as 1000-seed weight in grams (g)] of transgenic plants overexpressing the exogenous polynucleotides of some embodiments of the invention (using the cloned or synthetic genes listed in Table 10 above) under the regulation of a constitutive promoter (35S; SEQ ID NO: 675) when grown under high salinity irrigation conditions (80-100 mM NaCl) as compared to control plants. "Incr." = increment with respect to a control plant which has been transformed with an empty vector. Ave. = Average calculated from several transgenic events. "Event #" = number of event (transgenic transformation).

TABLE 28

Transgenic *Arabidopsis* plants exogenously expressing the polynucleotides of some embodiments of the invention under the regulation of the 35S promoter exhibit improved harvest index under nitrogen deficient growth conditions

| Gene Name | Event # | Harvest Index | | |
|---|---|---|---|---|
| | | Average | p-value | % increment |
| CTF113 | 5871.1 | 0.05 | 2.4E−02 | 67.8% |
| CTF113 | 5871.2 | 0.04 | 4.9E−02 | 42.8% |
| Control | | 0.03 | | 0.0% |

Table 28: Analyses of harvest index of transgenic plants transgenic plants overexpressing the exogenous polynucleotides of some embodiments of the invention (using the cloned or synthetic genes listed in Table 10 above) under the regulation of a constitutive promoter (35S; SEQ ID NO: 675) when grown under high salinity irrigation conditions (80-100 mM NaCl) as compared to control plants.
"Incr." = increment with respect to a control plant which has been transformed with an empty vector.
Ave. = Average calculated from several transgenic events.
"Event #" = number of event (transgenic transformation).

TABLE 29

Transgenic *Arabidopsis* plants exogenously expressing the polynucleotides of some embodiments of the invention under the regulation of the 35S promoter exhibit improved dry weight under high salinity irrigationv growth conditions

| Gene | | Dry Weight | | |
|---|---|---|---|---|
| Name | Event # | Average | p-value | % increment |
| CTF113 | 5871.2 | 0.82 | 4.3E−03 | 23.7% |
| CTF113 | 5873.3 | 0.83 | 2.9E−03 | 26.0% |
| Control | | 0.66 | | 0.0% |

Table 29: Analyses of dry weight of transgenic plants transgenic plants overexpressing the exogenous polynucleotides of some embodiments of the invention (using the cloned or synthetic genes listed in Table 10 above) under the regulation of a constitutive promoter (35S; SEQ ID NO: 675) when grown under high salinity irrigation conditions (80-100 mM NaCl) as compared to control plants.
"Incr." = increment with respect to a control plant which has been transformed with an empty vector.
Ave. = Average calculated from several transgenic events.
"Event #" = number of event (transgenic transformation).

The genes presented in Tables 30-31, hereinbelow, have improved plant performance and under regular growth conditions since they produced higher seed yield, harvest index, seed weight (expressed as 1000-seed weight) and plant biomass [(as expressed as plant dry weight (DW)] when grown under standard growth conditions, compared to control plants.

Tables 30-31 depict analyses of dry weight and seed yield (Table 30) and harvest index and seed weight (expressed as 1000-seed weight; Table 31) when grown under standard conditions (6 mM $KNO_3$, 1 mM $KH_2PO_4$, 1 mM $MgSO_4$, 2 mM $CaCl_2$ and microelements) in plants overexpressing the polynucleotides of some embodiments of the invention under the regulation of a constitutive promoter (35S; SEQ ID NO:675). Evaluation of each gene was performed by testing the performance of several events. Some of the genes were evaluated in more than one tissue culture assay and the results obtained were repeated. Event with p-value<0.05 was considered statistically significant.

TABLE 30

Transgenic *Arabidopsis* plants exogenously expressing the polynucleotides of some embodiments of the invention under the regulation of the 35S promoter exhibit improved plant biomass (dry weight) and seed yield under standard conditions

| Gene | | Dry Weight (g) | | | Gene | | Seed Yield (g) | | |
|---|---|---|---|---|---|---|---|---|---|
| Name | Event # | Ave. | P-Value | % incr. | Name | Event # | Ave. | P-Value | % incr. |
| BDL103 | 7853.3 | 0.94 | 3.3E−02 | 37.0% | BDL103 | 7853.1 | 0.30 | 1.3E−02 | 32.4% |
| BDL103 | 8033.4 | 0.98 | 3.3E−02 | 42.3% | BDL103 | 8033.4 | 0.30 | 2.6E−02 | 36.2% |
| Control | | 0.69 | | 0.0% | Control | | 0.22 | | 0.0% |
| BDL103 | 8033.3 | 1.32 | 2.5E−02 | 31.8% | BDL103 | 8033.3 | 0.71 | 1.2E−04 | 43.7% |
| Control | | 1.00 | | 0.0% | Control | | 0.49 | | 0.0% |

Table 30: Analyses of plant biomass (dry weight) and seed yield of transgenic plants overexpressing the exogenous polynucleotides of some embodiments of the invention (using the cloned or synthetic genes listed in Table 10 above) under the regulation of a constitutive promoter (35S; SEQ ID NO: 675) when grown under normal growth conditions (6 mM $KNO_3$, 1 mM $KH_2PO_4$, 1 mM $MgSO_4$, 2 mM $CaCl_2$ and microelements) as compared to control plants.
"Incr." = increment with respect to a control plant which has been transformed with an empty vector.
Ave. = Average calculated from several transgenic events.
"Event #" = number of event (transgenic transformation).

TABLE 31

Transgenic *Arabidopsis* plants exogenously expressing the polynucleotides of some embodiments of the invention under the regulation of the 35S promoter exhibit improved harvest index and seed weight under standard nitrogen conditions

| Gene Name | Event # | Ave. | P-Value | % incr. |
|---|---|---|---|---|
| Harvest Index | | | | |
| BDL14 | 5762.1 | 0.31 | 1.2E−02 | 45.1% |
| BDL14 | 5763.2 | 0.27 | 3.5E−02 | 29.6% |
| Control | | 0.21 | | 0.0% |
| BDL14 | 5762.1 | 0.53 | 3.9E−02 | 8.4% |
| Control | | 0.49 | | 0.0% |
| Seed Weight (g) | | | | |
| BDL103 | 7221.1 | 0.022 | 4.1E−03 | 22.3% |
| BDL103 | 7855.2 | 0.021 | 9.0E−03 | 18.3% |
| BDL103 | 8033.12 | 0.021 | 4.1E−02 | 19.5% |
| BDL103 | 8033.4 | 0.020 | 4.8E−02 | 13.3% |
| Control | | 0.018 | | 0.0% |

Table 31: Analyses of harvest index and seed weight of transgenic plants overexpressing the exogenous polynucleotides of some embodiments of the invention (using the cloned or synthetic genes listed in Table 10 above) under the regulation of a constitutive promoter (35S; SEQ ID NO: 675) when grown under standard nitrogen conditions (6 mM $KNO_3$, 1 mM $KH_2PO_4$, 1 mM $MgSO_4$, 2 mM $CaCl_2$ and microelements) as compared to control plants. "Incr." = increment with respect to a control plant which has been transformed with an empty vector. Ave. = Average calculated from several transgenic events. "Event #" = number of event (transgenic transformation).

Example 8

Evaluation of Transgenic *Arabidopsis* Plant Growth Under Abiotic Stress as Well as Under Favorable Conditions in Greenhouse Assay Grown Until Bolting This assay follows seed yield production, the biomass formation and the rosette area growth of plants grown in the greenhouse at high salinity and regular growth conditions. Transgenic *Arabidopsis* seeds were sown in agar media supplemented with ½ MS medium and a selection agent (Kanamycin). The $T_2$ transgenic seedlings were then transplanted to 1.7 trays filled with peat and perlite. The trays were irrigated with tap water (provided from the pots' bottom). Half of the plants were irrigated with a salt solution (50-150 mM NaCl and 5 mM $CaCl_2$) so as to induce salinity stress (stress conditions). The other half of the plants was irrigated with tap water (normal conditions). All plants were grown in the greenhouse until 90% of plants reach bolting (inflorescent start to emerge). Plant biomass (the above ground tissue) was weighted immediately after harvesting the rosette (plant fresh weight [FW]). Following, plants were dried in an oven at 50° C. for 48 hours and weighted (plant dry weight [DW]).

Each construct was validated at its $T_2$ generation. Transgenic plants transformed with a construct conformed by an empty vector carrying the 35S promoter and the selectable marker was used as control.

The plants were analyzed for their overall size, growth rate, fresh weight and dry matter. Transgenic plants performance was compared to control plants grown in parallel under the same conditions.

The experiment was planned in nested randomized plot distribution. For each gene of the invention three to five independent transformation events were analyzed from each construct.

Digital Imaging

A laboratory image acquisition system, which consists of a digital reflex camera (Canon EOS 300D) attached with a 55 mm focal length lens (Canon EF-S series), mounted on a reproduction device (Kaiser RS), which includes 4 light units (4×150 Watts light bulb) was used for capturing images of plant samples.

The image capturing process was repeated every 2 days starting from day 1 after transplanting till day 15. Same camera, placed in a custom made iron mount, was used for capturing images of larger plants sawn in white tubs in an environmental controlled greenhouse. During the capture process, the tubes were placed beneath the iron mount, while avoiding direct sun light and casting of shadows.

An image analysis system was used, which consists of a personal desktop computer (Intel P4 3.0 GHz processor) and a public domain program—ImageJ 1.39 [Java based image processing program which was developed at the U.S. National Institutes of Health and freely available on the internet at Hypertext Transfer Protocol://rsbweb (dot) nih (dot) gov/]. Images were captured in resolution of 10 Mega Pixels (3888×2592 pixels) and stored in a low compression JPEG (Joint Photographic Experts Group standard) format. Next, analyzed data was saved to text files and processed using the JMP statistical analysis software (SAS institute).

Leaf Analysis

Using the digital analysis leaves data was calculated, including leaf number, rosette area, rosette diameter, leaf blade area, plot coverage and leaf petiole area.

Vegetative Growth Rate: is the Rate of Growth of the Plant as Defined by Formula VIII, IX, X and XI as Described in Example 7 Hereinabove.

Plant Fresh and Dry Weight

On about day 40 from sowing, the plants were harvested and directly weighted for the determination of the plant fresh weight (FW) and left to dry at 50° C. in a drying chamber for about 48 hours before weighting to determine plant dry weight (DW).

Statistical Analyses

To identify genes conferring significantly improved ABST, the results obtained from the transgenic plants were compared to those obtained from control plants. To identify outperforming genes and constructs, results from the independent transformation events tested are analyzed separately. Data was analyzed using Student's t-test and results were considered significant if the p value was less than 0.1. The JMP statistics software package was used (Version 5.2.1, SAS Institute Inc., Cary, N.C., USA).

Experimental Results:

The genes presented in Tables 32-36, hereinbelow, were found to increase ABST when grown under high salinity irrigation conditions, compared to control plants. These genes produced larger plants with a larger photosynthetic capacity when grown under limiting nitrogen conditions.

Tables 32-36 depict analyses of plant biomass and photosynthetic area (fresh weight, dry weight, rosette diameter, rosette area and plot coverage) when grown under high salinity irrigation conditions (80-150 mM NaCl) in plants overexpressing the polynucleotides of some embodiments of the invention under the regulation of a constitutive promoter (At6669; SEQ ID NO:674). Evaluation of each gene was performed by testing the performance of several events. Some of the genes were evaluated in more than one tissue culture assay and the results obtained were repeated. Event with p-value<0.05 was considered statistically significant.

TABLE 32

Transgenic *Arabidopsis* plants exogenously expressing the polynucleotides of some embodiments of the invention exhibit improved plant biomass under high salinity conditions

| Gene Name | Event # | Ave. | p-value | % incr. |
|---|---|---|---|---|
| Fresh weight (g) | | | | |
| LAB22 | 11064.6 | 0.57 | 3.0E−06 | 75.1% |
| LAB41 | 11552.1 | 0.40 | 1.8E−02 | 22.2% |
| Control | | 0.33 | | 0.0% |
| LAB22 | 11062.1 | 0.57 | 1.5E−02 | 11.2% |
| LAB21 | 11144.1 | 0.63 | 9.3E−03 | 21.2% |
| LAB25 | 11341.2 | 0.64 | 3.4E−02 | 24.8% |
| LAB17 | 11533.1 | 0.58 | 8.1E−03 | 12.7% |
| LAB17 | 11533.6 | 0.66 | 1.5E−02 | 27.8% |
| LAB15 | 11641.1 | 0.56 | 3.9E−02 | 7.9% |
| Control | | 0.52 | | 0.0% |
| LAB40 | 11154.1 | 0.75 | 1.2E−02 | 20.8% |
| LAB40 | 11154.4 | 0.86 | 8.2E−03 | 38.4% |
| LAB40 | 11154.5 | 0.76 | 2.0E−02 | 23.2% |
| LAB24 | 11193.1 | 0.84 | 3.9E−03 | 35.4% |
| LAB49 | 11281.2 | 0.84 | 1.0E−03 | 35.4% |
| LAB3 | 11333.9 | 0.83 | 5.0E−03 | 33.3% |
| LAB14 | 11471.1 | 0.92 | 2.9E−04 | 48.5% |
| LAB14 | 11474.1 | 0.87 | 7.6E−04 | 40.4% |
| LAB14 | 11474.3 | 0.76 | 4.5E−02 | 22.2% |
| LAB51 | 11563.1 | 0.83 | 1.4E−03 | 34.3% |
| Control | | 0.62 | | 0.0% |
| LAB35 | 11462.3 | 0.77 | 1.7E−02 | 14.3% |
| LAB35 | 11462.5 | 0.75 | 3.9E−02 | 11.5% |
| LAB14 | 11472.1 | 0.88 | 7.8E−04 | 30.0% |
| Control | | 0.67 | | 0.0% |
| Dry weight (g) | | | | |
| LAB22 | 11064.6 | 0.07 | 1.0E−03 | 86.8% |
| LAB41 | 11551.2 | 0.07 | 2.4E−02 | 113.2% |
| Control | | 0.03 | | 0.0% |
| LAB21 | 11144.1 | 0.07 | 6.4E−03 | 22.8% |
| LAB34 | 11175.1 | 0.07 | 1.8E−02 | 35.7% |
| LAB33 | 11272.4 | 0.06 | 2.0E−02 | 15.8% |
| LAB33 | 11273.1 | 0.06 | 2.0E−02 | 15.8% |
| LAB25 | 11341.2 | 0.06 | 1.3E−02 | 18.1% |
| LAB17 | 11533.6 | 0.07 | 1.9E−03 | 32.3% |
| LAB23 | 11571.2 | 0.08 | 1.2E−02 | 42.7% |
| LAB23 | 11571.5 | 0.07 | 5.7E−03 | 24.0% |
| LAB15 | 11642.2 | 0.07 | 3.8E−02 | 36.8% |
| Control | | 0.05 | | 0.0% |
| LAB40 | 11151.1 | 0.09 | 1.4E−02 | 24.7% |
| LAB40 | 11154.5 | 0.08 | 4.2E−02 | 16.7% |
| LAB24 | 11193.1 | 0.09 | 3.9E−02 | 28.9% |
| LAB24 | 11193.5 | 0.09 | 2.5E−03 | 31.6% |
| LAB3 | 11333.9 | 0.08 | 4.6E−02 | 17.5% |
| LAB35 | 11461.2 | 0.08 | 3.1E−02 | 17.5% |
| LAB14 | 11471.1 | 0.10 | 9.4E−04 | 38.6% |
| LAB14 | 11474.1 | 0.09 | 1.3E−02 | 24.6% |
| LAB51 | 11561.2 | 0.10 | 5.7E−03 | 43.9% |
| LAB51 | 11563.1 | 0.09 | 9.7E−03 | 26.3% |
| Control | | 0.07 | | 0.0% |
| LAB35 | 11462.3 | 0.09 | 2.3E−02 | 22.4% |
| LAB35 | 11462.5 | 0.09 | 3.3E−02 | 18.9% |
| LAB14 | 11472.1 | 0.09 | 1.2E−02 | 30.2% |
| Control | | 0.07 | | 0.0% |

Table 32: Analyses of fresh weight and dry weight of transgenic plants overexpressing the exogenous polynucleotides of some embodiments of the invention (using the cloned or synthetic genes listed in Table 10 above) under the regulation of a constitutive promoter (6669) when grown under high salinity conditions as compared to control plants, "g" = grams. "Incr." = increment with respect to a control plant which has been transformed with an empty vector. Ave. = Average calculated from several transgenic events. "Event #" = number of event (transgenic transformation).

TABLE 33

Transgenic *Arabidopsis* plants exogenously expressing the polynucleotides of some embodiments of the invention exhibit improved plant biomass under high salinity conditions

| Gene Name | Event # | Ave. | p-value | % incr. |
|---|---|---|---|---|
| Rosette diameter (cm) | | | | |
| LAB22 | 11064.6 | 2.28 | 3.4E−02 | 25.5% |
| LAB41 | 11551.2 | 2.49 | 1.9E−02 | 37.3% |
| LAB41 | 11552.1 | 2.10 | 9.9E−03 | 15.8% |
| Control | | 1.81 | | 0.0% |
| LAB21 | 11144.1 | 2.69 | 2.4E−02 | 12.6% |
| LAB25 | 11341.2 | 2.77 | 7.1E−03 | 16.2% |
| LAB17 | 11531.6 | 2.67 | 9.1E−03 | 12.1% |
| LAB15 | 11642.2 | 2.80 | 5.2E−03 | 17.4% |
| Control | | 2.39 | | 0.0% |
| LAB40 | 11154.4 | 2.92 | 2.6E−03 | 24.3% |
| LAB40 | 11154.5 | 2.80 | 6.5E−03 | 19.2% |
| LAB24 | 11193.1 | 2.70 | 2.9E−02 | 15.3% |
| LAB24 | 11193.5 | 2.71 | 4.0E−02 | 15.7% |
| LAB49 | 11281.2 | 2.72 | 1.3E−02 | 16.0% |
| LAB5 | 11443.4 | 2.63 | 3.5E−02 | 12.2% |
| LAB5 | 11444.1 | 3.02 | 1.0E−03 | 28.8% |
| LAB5 | 11444.5 | 2.86 | 3.5E−02 | 21.9% |
| LAB51 | 11561.1 | 2.74 | 3.1E−02 | 17.0% |
| LAB51 | 11561.2 | 2.81 | 2.5E−02 | 19.8% |
| LAB51 | 11563.1 | 2.80 | 5.7E−03 | 19.3% |
| Control | | 2.34 | | 0.0% |
| Rosette area (cm²) | | | | |
| LAB22 | 11064.6 | 1.88 | 2.6E−03 | 49.0% |
| LAB41 | 11551.2 | 2.14 | 3.3E−02 | 70.0% |
| LAB41 | 11552.1 | 1.50 | 4.1E−02 | 18.8% |
| Control | | 1.26 | | 0.0% |
| LAB21 | 11144.1 | 2.31 | 1.1E−02 | 27.4% |
| LAB25 | 11341.2 | 2.44 | 7.1E−03 | 34.4% |
| LAB17 | 11531.6 | 2.17 | 3.3E−02 | 19.7% |
| LAB17 | 11533.6 | 2.65 | 8.5E−03 | 45.7% |
| LAB15 | 11642.2 | 2.45 | 6.2E−03 | 35.1% |
| Control | | 1.82 | | 0.0% |
| LAB40 | 11151.1 | 2.42 | 1.6E−02 | 44.8% |
| LAB40 | 11154.4 | 2.82 | 2.2E−02 | 68.2% |
| LAB40 | 11154.5 | 2.36 | 3.6E−03 | 40.7% |
| LAB24 | 11193.1 | 2.17 | 3.9E−02 | 29.9% |
| LAB49 | 11281.2 | 2.42 | 2.6E−03 | 44.8% |
| LAB3 | 11333.9 | 2.43 | 3.3E−02 | 45.4% |
| LAB5 | 11443.4 | 2.18 | 1.3E−02 | 30.2% |
| LAB5 | 11444.1 | 2.78 | 8.6E−03 | 66.1% |
| LAB5 | 11444.5 | 2.52 | 2.4E−02 | 50.3% |
| LAB51 | 11561.1 | 2.27 | 6.6E−03 | 35.5% |
| LAB51 | 11561.2 | 2.47 | 2.5E−03 | 47.6% |
| LAB51 | 11563.1 | 2.37 | 2.1E−02 | 41.5% |
| Control | | 1.67 | | 0.0% |

Table 33: Analyses of rosette diameter and area of transgenic plants overexpressing the exogenous polynucleotides of some embodiments of the invention (using the cloned or synthetic genes listed in Table 10 above) under the regulation of a constitutive promoter (6669) when grown under high salinity conditions as compared to control plants. "Incr." = increment with respect to a control plant which has been transformed with an empty vector. Ave. = Average calculated from several transgenic events. "Event #" = number of event (transgenic transformation).

TABLE 34

Transgenic *Arabidopsis* plants exogenously expressing the polynucleotides of some embodiments of the invention exhibit improved plant biomass under high salinity conditions

| Gene Name | Event # | Ave. | p-value | % incr. |
|---|---|---|---|---|
| Plot coverage (cm²) | | | | |
| LAB22 | 11064.6 | 15.03 | 2.6E−03 | 49.0% |
| LAB41 | 11551.2 | 17.15 | 3.3E−02 | 70.0% |
| LAB41 | 11552.1 | 11.98 | 4.1E−02 | 18.8% |
| Control | | 10.09 | | 0.0% |
| LAB21 | 11144.1 | 18.51 | 1.1E−02 | 27.4% |
| LAB25 | 11341.2 | 19.53 | 7.1E−03 | 34.4% |
| LAB17 | 11531.6 | 17.40 | 3.3E−02 | 19.7% |

TABLE 34-continued

Transgenic *Arabidopsis* plants exogenously expressing the polynucleotides of some embodiments of the invention exhibit improved plant biomass under high salinity conditions

| Gene Name | Event # | Ave. | p-value | % incr. |
|---|---|---|---|---|
| LAB17 | 11533.6 | 21.17 | 8.5E−03 | 45.7% |
| LAB15 | 11642.2 | 19.62 | 6.2E−03 | 35.1% |
| Control |  | 14.53 |  | 0.0% |
| LAB40 | 11154.1 | 16.79 | 3.3E−02 | 25.4% |
| LAB40 | 11154.4 | 22.53 | 2.2E−02 | 68.2% |
| LAB40 | 11154.5 | 18.84 | 3.6E−03 | 40.7% |
| LAB24 | 11193.1 | 17.40 | 3.9E−02 | 29.9% |
| LAB49 | 11281.2 | 19.40 | 2.6E−03 | 44.8% |
| LAB3 | 11333.9 | 19.48 | 3.3E−02 | 45.4% |
| LAB5 | 11443.4 | 17.44 | 1.3E−02 | 30.2% |
| LAB5 | 11444.1 | 22.24 | 8.6E−03 | 66.1% |
| LAB5 | 11444.5 | 20.13 | 2.4E−02 | 50.3% |
| LAB51 | 11561.1 | 18.15 | 6.6E−03 | 35.5% |
| LAB51 | 11561.2 | 19.77 | 2.5E−03 | 47.6% |
| LAB51 | 11563.1 | 18.95 | 2.1E−02 | 41.5% |
| Control |  | 13.39 |  | 0.0% |
| Leaf number | | | | |
| LAB16 | 11033.2 | 8.13 | 5.0E−04 | 12.3% |
| LAB16 | 11034.1 | 7.94 | 2.3E−03 | 9.7% |
| LAB22 | 11062.1 | 7.63 | 3.2E−02 | 5.4% |
| LAB22 | 11064.6 | 8.00 | 1.3E−02 | 10.6% |
| Control |  | 7.23 |  | 0.0% |
| LAB5 | 11441.1 | 8.41 | 1.7E−02 | 13.1% |
| Control |  | 7.44 |  | 0.0% |

Table 34: Analyses of plot coverage and leaf number of transgenic plants overexpressing the exogenous polynucleotides of some embodiments of the invention (using the cloned or synthetic genes listed in Table 32 above) under the regulation of a constitutive promoter (6669) when grown under high salinity conditions as compared to control plants. "Incr." = increment with respect to a control plant which has been transformed with an empty vector. Ave. = Average calculated from several transgenic events. "Event #" = number of event (transgenic transformation).

TABLE 35

Transgenic *Arabidopsis* plants exogenously expressing the polynucleotides of some embodiments of the invention exhibit improved plant biomass and growth rate under high salinity conditions

| Gene Name | Event # | Average | p-value | % incr. |
|---|---|---|---|---|
| RGR of rosette area (Regression coefficient) | | | | |
| LAB11 | 11024.3 | 0.24 | 2.9E−02 | 46.4% |
| LAB16 | 11033.2 | 0.29 | 1.6E−03 | 75.5% |
| LAB16 | 11034.1 | 0.33 | 4.9E−05 | 101.2% |
| LAB22 | 11062.1 | 0.26 | 5.9E−03 | 59.3% |
| LAB22 | 11062.3 | 0.25 | 2.5E−02 | 51.6% |
| LAB22 | 11064.6 | 0.25 | 6.5E−03 | 55.1% |
| LAB41 | 11551.2 | 0.29 | 4.4E−04 | 76.7% |
| Control |  | 0.16 |  | 0.0% |
| LAB21 | 11144.1 | 0.30 | 3.9E−02 | 27.0% |
| LAB25 | 11341.2 | 0.32 | 1.4E−02 | 34.6% |
| LAB17 | 11533.6 | 0.34 | 2.5E−02 | 43.8% |
| LAB17 | 11534.1 | 0.31 | 4.4E−02 | 29.0% |
| LAB23 | 11571.2 | 0.34 | 1.4E−02 | 40.4% |
| LAB23 | 11571.5 | 0.32 | 1.1E−02 | 34.6% |
| LAB15 | 11642.2 | 0.32 | 1.2E−02 | 33.1% |
| Control |  | 0.24 |  | 0.0% |
| LAB40 | 11151.1 | 0.31 | 2.5E−02 | 45.7% |
| LAB40 | 11154.4 | 0.36 | 2.7E−03 | 65.8% |
| LAB49 | 11281.2 | 0.31 | 4.4E−02 | 41.6% |
| LAB49 | 11281.4 | 0.35 | 6.3E−03 | 62.6% |
| LAB3 | 11333.9 | 0.31 | 3.3E−02 | 45.8% |
| LAB5 | 11444.1 | 0.36 | 3.5E−03 | 65.6% |
| LAB5 | 11444.5 | 0.32 | 1.8E−02 | 50.1% |
| LAB51 | 11561.2 | 0.32 | 2.6E−02 | 47.4% |

TABLE 35-continued

Transgenic *Arabidopsis* plants exogenously expressing the polynucleotides of some embodiments of the invention exhibit improved plant biomass and growth rate under high salinity conditions

| Gene Name | Event # | Average | p-value | % incr. |
|---|---|---|---|---|
| LAB51 | 11563.1 | 0.31 | 3.9E−02 | 42.9% |
| Control |  | 0.22 |  | 0.0% |
| RGR of rosette diameter (Regression coefficient) | | | | |
| LAB11 | 11024.3 | 0.23 | 2.1E−02 | 32.4% |
| LAB16 | 11033.2 | 0.25 | 2.4E−03 | 44.8% |
| LAB16 | 11034.1 | 0.28 | 8.6E−05 | 58.1% |
| LAB16 | 11034.4 | 0.24 | 7.6E−03 | 39.2% |
| LAB22 | 11062.1 | 0.24 | 5.1E−03 | 37.9% |
| LAB22 | 11064.6 | 0.24 | 3.6E−03 | 37.4% |
| LAB41 | 11551.2 | 0.26 | 4.5E−04 | 47.8% |
| Control |  | 0.17 |  | 0.0% |
| LAB25 | 11341.2 | 0.28 | 4.7E−02 | 15.9% |
| LAB13 | Control | 0.24 |  | 0.0% |
| LAB3 | 11333.9 | 0.30 | 3.9E−02 | 25.6% |
| Control |  | 0.24 |  | 0.0% |

Table 35: Analyses of relative growth rate (RGR) of rosette area and diameter of transgenic plants overexpressing the exogenous polynucleotides of some embodiments of the invention (using the cloned or synthetic genes listed in Table 10 above) under the regulation of a constitutive promoter (6669) when grown under high salinity conditions as compared to control plants. Ave. = Average calculated from several transgenic events. "Event #" = number of event (transgenic transformation).

TABLE 36

Transgenic *Arabidopsis* plants exogenously expressing the polynucleotides of some embodiments of the invention exhibit improved plant biomass and growth rate under high salinity conditions

| Gene Name | Event # | Ave. | p-value | % incr. |
|---|---|---|---|---|
| RGR of plot coverage | | | | |
| LAB11 | 11024.3 | 1.90 | 2.9E−02 | 46.4% |
| LAB16 | 11033.2 | 2.28 | 1.6E−03 | 75.5% |
| LAB16 | 11034.1 | 2.61 | 4.9E−05 | 101.2% |
| LAB22 | 11062.1 | 2.07 | 5.9E−03 | 59.3% |
| LAB22 | 11062.3 | 1.97 | 2.5E−02 | 51.6% |
| LAB22 | 11064.6 | 2.02 | 6.5E−03 | 55.1% |
| LAB41 | 11551.2 | 2.30 | 4.4E−04 | 76.7% |
| Control |  | 2.43 | 3.9E−02 | 27.0% |
| LAB21 | 11144.1 | 2.58 | 1.4E−02 | 34.6% |
| LAB25 | 11341.2 | 2.76 | 2.5E−02 | 43.8% |
| LAB17 | 11533.6 | 2.47 | 4.4E−02 | 29.0% |
| LAB17 | 11534.1 | 2.69 | 1.4E−02 | 40.4% |
| LAB23 | 11571.2 | 2.58 | 1.1E−02 | 34.6% |
| LAB23 | 11571.5 | 2.55 | 1.2E−02 | 33.1% |
| LAB15 | 11642.2 | 2.86 | 2.7E−03 | 65.8% |
| Control |  | 2.44 | 4.4E−02 | 41.6% |
| LAB40 | 11151.1 | 2.80 | 6.3E−03 | 62.6% |
| LAB40 | 11154.4 | 2.51 | 3.3E−02 | 45.8% |
| LAB49 | 11281.2 | 2.85 | 3.5E−03 | 65.6% |
| LAB49 | 11281.4 | 2.59 | 1.8E−02 | 50.1% |
| LAB3 | 11333.9 | 2.54 | 2.6E−02 | 47.4% |
| LAB5 | 11444.1 | 2.46 | 3.9E−02 | 42.9% |
| LAB5 | 11444.5 | 1.90 | 2.9E−02 | 46.4% |
| LAB51 | 11561.2 | 2.28 | 1.6E−03 | 75.5% |
| LAB51 | 11563.1 | 2.61 | 4.9E−05 | 101.2% |
| Control |  | 2.07 | 5.9E−03 | 59.3% |
| LAB40 | 11151.1 | 2.80 | 6.3E−03 | 62.6% |
| LAB40 | 11154.4 | 2.51 | 3.3E−02 | 45.8% |
| LAB49 | 11281.2 | 2.85 | 3.5E−03 | 65.6% |
| LAB49 | 11281.4 | 2.59 | 1.8E−02 | 50.1% |
| LAB3 | 11333.9 | 2.54 | 2.6E−02 | 47.4% |
| LAB5 | 11444.1 | 2.46 | 3.9E−02 | 42.9% |
| LAB5 | 11444.5 | 1.90 | 2.9E−02 | 46.4% |
| LAB51 | 11561.2 | 2.28 | 1.6E−03 | 75.5% |

TABLE 36-continued

Transgenic *Arabidopsis* plants exogenously expressing the polynucleotides of some embodiments of the invention exhibit improved plant biomass and growth rate under high salinity conditions

| Gene Name | Event # | Ave. | p-value | % incr. |
|---|---|---|---|---|
| LAB51 | 11563.1 | 2.61 | 4.9E−05 | 101.2% |
| Control | | 2.07 | 5.9E−03 | 59.3% |

Table 36: Analyses of relative growth rate (RGR) of plot coverage of transgenic plants overexpressing the exogenous polynucleotides of some embodiments of the invention (using the cloned or synthetic genes listed in Table 10 above) under the regulation of a constitutive promoter (6669) when grown under high salinity conditions as compared to control plants. "Incr." = increment with respect to a control plant which has been transformed with an empty vector. Ave. = Average calculated from several transgenic events. "Event #" = number of event (transgenic transformation).

Tables 37-41 depict analyses of plant biomass, growth rate and photosynthetic area (fresh weight, dry weight, rosette diameter, rosette area and plot coverage) when grown under normal conditions in plants overexpressing the polynucleotides of some embodiments of the invention under the regulation of a constitutive promoter (At6669; SEQ ID NO:674). Evaluation of each gene was performed by testing the performance of several events. Some of the genes were evaluated in more than one tissue culture assay and the results obtained were repeated. Event with p-value<0.05 was considered statistically significant.

TABLE 37

Transgenic *Arabidopsis* plants exogenously expressing the polynucleotides of some embodiments of the invention exhibit improved plant biomass under normal conditions

| Gene Name | Event # | Ave. | p-value | % incr. |
|---|---|---|---|---|
| *Fresh weight (g)* | | | | |
| LAB16 | 11033.2 | 1.13 | 2.4E−02 | 125.3% |
| LAB22 | 11064.6 | 1.19 | 0.0E+00 | 139.1% |
| LAB11 | Control | 0.50 | | 0.0% |
| LAB38 | 11434.3 | 2.59 | 4.5E−02 | 28.7% |
| Control | | 2.02 | | 0.0% |
| LAB40 | 11151.1 | 1.81 | 2.9E−02 | 16.9% |
| LAB40 | 11154.5 | 1.81 | 2.9E−02 | 16.9% |
| LAB39 | 11182.1 | 1.98 | 1.4E−03 | 27.4% |
| LAB24 | 11193.1 | 1.84 | 1.2E−02 | 19.0% |
| LAB49 | 11281.6 | 2.19 | 2.6E−05 | 41.1% |
| LAB3 | 11331.1 | 1.74 | 1.4E−02 | 12.1% |
| LAB5 | 11444.1 | 2.07 | 8.1E−03 | 33.5% |
| LAB35 | 11461.2 | 2.30 | 1.0E−05 | 48.4% |
| LAB35 | 11462.5 | 1.91 | 1.2E−03 | 23.0% |
| LAB14 | 11474.1 | 1.80 | 3.3E−02 | 16.1% |
| Control | | 1.55 | | 0.0% |
| LAB49 | 11281.6 | 1.84 | 3.8E−02 | 9.9% |
| Control | | 1.68 | | 0.0% |
| *Dry weight (g)* | | | | |
| LAB16 | 11033.2 | 0.11 | 0.0E+00 | 111.5% |
| LAB22 | 11062.1 | 0.09 | 4.0E−06 | 72.2% |
| LAB22 | 11064.6 | 0.11 | 0.0E+00 | 114.0% |
| Control | | 0.05 | | 0.0% |
| LAB40 | 11151.1 | 0.16 | 6.7E−03 | 18.8% |
| LAB40 | 11154.5 | 0.15 | 1.7E−02 | 13.1% |
| LAB39 | 11182.1 | 0.17 | 5.6E−03 | 27.2% |

TABLE 37-continued

Transgenic *Arabidopsis* plants exogenously expressing the polynucleotides of some embodiments of the invention exhibit improved plant biomass under normal conditions

| Gene Name | Event # | Ave. | p-value | % incr. |
|---|---|---|---|---|
| LAB24 | 11193.1 | 0.16 | 6.3E−03 | 16.9% |
| LAB49 | 11281.6 | 0.18 | 1.8E−04 | 36.6% |
| LAB5 | 11444.1 | 0.16 | 5.2E−03 | 23.0% |
| LAB35 | 11461.2 | 0.19 | 1.4E−02 | 46.0% |
| LAB14 | 11471.1 | 0.15 | 1.8E−02 | 13.6% |
| LAB51 | 11561.5 | 0.15 | 2.3E−02 | 15.5% |
| Control | | 0.13 | | 0.0% |

Table 37: Analyses of fresh weight and dry weight of transgenic plants overexpressing the exogenous polynucleotides of some embodiments of the invention (using the cloned or synthetic genes listed in Table 10 above) under the regulation of a constitutive promoter (At6669; SEQ ID NO: 674) when grown under noraml conditions as compared to control plants, "g" = grams. "Incr." = increment with respect to a control plant which has been transformed with an empty vector. Ave. = Average calculated from several transgenic events. "Event #" = number of event (transgenic transformation).

TABLE 38

Transgenic *Arabidopsis* plants exogenously expressing the polynucleotides of some embodiments of the invention exhibit improved plant biomass normal conditions

| Gene Name | Event # | Ave. | p-value | % incr. |
|---|---|---|---|---|
| *Rosette diameter (cm)* | | | | |
| LAB16 | 11033.2 | 3.00 | 3.5E−02 | 73.6% |
| LAB22 | 11064.6 | 2.84 | 0.0E+00 | 64.4% |
| LAB41 | 11551.4 | 1.95 | 3.7E−02 | 12.8% |
| Control | | 1.73 | | 0.0% |
| LAB40 | 11151.1 | 3.31 | 6.5E−03 | 17.4% |
| LAB40 | 11154.1 | 3.82 | 2.3E−02 | 35.7% |
| LAB39 | 11182.1 | 3.30 | 1.0E−03 | 17.2% |
| LAB24 | 11192.1 | 3.23 | 2.4E−03 | 14.7% |
| LAB24 | 11193.1 | 3.21 | 2.8E−03 | 13.9% |
| LAB49 | 11281.4 | 3.33 | 2.0E−03 | 18.1% |
| LAB49 | 11281.6 | 3.57 | 1.5E−04 | 26.6% |
| LAB3 | 11333.1 | 3.22 | 2.4E−03 | 14.3% |
| LAB3 | 11333.9 | 3.24 | 5.2E−03 | 15.1% |
| LAB5 | 11444.1 | 3.42 | 3.6E−04 | 21.3% |
| LAB35 | 11461.2 | 3.81 | 1.8E−02 | 35.3% |
| LAB51 | 11561.5 | 3.30 | 1.3E−03 | 17.0% |
| Control | | 2.82 | | 0.0% |
| *Rosette area (cm$^2$)* | | | | |
| LAB16 | 11033.2 | 2.91 | 9.5E−03 | 150.9% |
| LAB22 | 11064.6 | 2.85 | 0.0E+00 | 145.9% |
| Control | | 1.16 | | 0.0% |
| LAB38 | 11434.3 | 4.48 | 4.1E−02 | 46.7% |
| Control | | 3.05 | | 0.0% |
| LAB40 | 11151.1 | 3.19 | 2.4E−04 | 42.6% |
| LAB39 | 11182.1 | 3.05 | 5.8E−03 | 36.0% |
| LAB24 | 11192.1 | 2.90 | 1.9E−03 | 29.5% |
| LAB24 | 11193.1 | 2.77 | 1.2E−02 | 23.6% |
| LAB49 | 11281.4 | 2.91 | 1.7E−03 | 29.7% |
| LAB49 | 11281.6 | 3.26 | 1.8E−04 | 45.4% |
| LAB3 | 11333.1 | 2.76 | 2.3E−02 | 23.1% |
| LAB3 | 11333.9 | 2.92 | 4.1E−02 | 30.4% |
| LAB5 | 11443.3 | 3.19 | 1.8E−02 | 42.4% |
| LAB5 | 11444.1 | 3.24 | 2.5E−04 | 44.7% |
| LAB35 | 11461.2 | 4.25 | 1.8E−02 | 89.8% |
| LAB51 | 11561.5 | 2.77 | 9.7E−03 | 23.6% |
| Control | | 2.24 | | 0.0% |

Table 38: Analyses of rosette diameter and area of transgenic plants overexpressing the exogenous polynucleotides of some embodiments of the invention (using the cloned or synthetic genes listed in Table 10 above) under the regulation of a constitutive promoter (At6669; SEQ ID NO: 674) when grown under normal conditions as compared to control plants. "Incr." = increment with respect to a control plant which has been transformed with an empty vector. Ave. = Average calculated from several transgenic events. "Event #" = number of event (transgenic transformation).

TABLE 39

Transgenic *Arabidopsis* plants exogenously expressing the polynucleotides of some embodiments of the invention exhibit improved plant biomass under normal conditions

| Gene Name | Event # | Ave. | p-value | % incr. |
|---|---|---|---|---|
| Plot coverage (cm$^2$) | | | | |
| LAB16 | 11033.2 | 23.25 | 9.5E−03 | 150.9% |
| LAB22 | 11064.6 | 22.79 | 0.0E+00 | 145.9% |
| Control | | 9.27 | | 0.0% |
| LAB38 | 11434.3 | 35.81 | 4.1E−02 | 46.7% |
| Control | | 24.41 | | 0.0% |
| LAB40 | 11151.1 | 25.56 | 2.4E−04 | 42.6% |
| LAB39 | 11182.1 | 24.38 | 5.8E−03 | 36.0% |
| LAB24 | 11192.1 | 23.21 | 1.9E−03 | 29.5% |
| LAB24 | 11193.1 | 22.15 | 1.2E−02 | 23.6% |
| LAB49 | 11281.4 | 23.25 | 1.7E−03 | 29.7% |
| LAB49 | 11281.6 | 26.05 | 1.8E−04 | 45.4% |
| LAB3 | 11333.1 | 22.06 | 2.3E−02 | 23.1% |
| LAB3 | 11333.9 | 23.38 | 4.1E−02 | 30.4% |
| LAB5 | 11443.3 | 25.53 | 1.8E−02 | 42.4% |
| LAB5 | 11444.1 | 25.93 | 2.5E−04 | 44.7% |
| LAB35 | 11461.2 | 34.01 | 1.8E−02 | 89.8% |
| LAB51 | 11561.5 | 22.16 | 9.7E−03 | 23.6% |
| Control | | 17.92 | | 0.0% |
| Leaf number | | | | |
| LAB16 | 11032.5 | 8.44 | 4.1E−02 | 10.9% |
| LAB22 | 11064.6 | 8.69 | 9.0E−04 | 14.2% |
| Control | | 7.61 | | 0.0% |
| LAB39 | 11182.1 | 8.25 | 3.2E−02 | 8.5% |
| LAB49 | 11283.6 | 8.31 | 1.1E−02 | 9.3% |
| LAB35 | 11461.2 | 9.00 | 1.3E−03 | 18.4% |
| Control | | 7.60 | | 0.0% |

Table 39: Analyses of plot coverage and leaf number of transgenic plants overexpressing the exogenous polynucleotides of some embodiments of the invention (using the cloned or synthetic genes listed in Table 10 above) under the regulation of a constitutive promoter (At6669; SEQ ID NO: 674) when grown under normal conditions as compared to control plants. "Incr." = increment with respect to a control plant which has been transformed with an empty vector. Ave. = Average calculated from several transgenic events. "Event #" = number of event (transgenic transformation).

TABLE 40

Transgenic *Arabidopsis* plants exogenously expressing the polynucleotides of some embodiments of the invention exhibit improved plant biomass and growth rate under normal conditions

| Gene Name | Event # | Ave. | p-value | % incr. |
|---|---|---|---|---|
| RGR of rosette area (Regression coefficient) | | | | |
| LAB16 | 11032.5 | 0.33 | 9.2E−04 | 121.8% |
| LAB16 | 11033.2 | 0.39 | 0.0E+00 | 163.5% |
| LAB22 | 11062.1 | 0.30 | 4.3E−05 | 101.9% |
| LAB22 | 11063.4 | 0.29 | 7.0E−03 | 93.7% |
| LAB22 | 11064.1 | 0.21 | 4.9E−02 | 43.5% |
| LAB22 | 11064.6 | 0.39 | 0.0E+00 | 161.4% |
| Control | | 0.15 | | 0.0% |
| LAB17 | 11534.1 | 0.66 | 4.6E−02 | 60.4% |
| Control | | 0.41 | | 0.0% |
| LAB40 | 11151.1 | 0.42 | 2.6E−02 | 42.0% |
| LAB40 | 11154.1 | 0.51 | 7.6E−04 | 75.6% |
| LAB39 | 11182.1 | 0.41 | 3.6E−02 | 38.3% |
| LAB49 | 11281.6 | 0.43 | 2.0E−02 | 45.4% |
| LAB5 | 11443.3 | 0.42 | 2.1E−02 | 43.5% |
| LAB5 | 11444.1 | 0.42 | 2.2E−02 | 44.5% |
| LAB5 | 11444.5 | 0.45 | 1.9E−02 | 53.3% |
| LAB35 | 11461.2 | 0.56 | 1.6E−04 | 89.8% |
| Control | | 0.29 | | 0.0% |
| RGR of rosette diameter (Regression coefficient) | | | | |
| LAB16 | 11032.5 | 0.27 | 1.7E−03 | 65.7% |
| LAB16 | 11033.2 | 0.32 | 0.0E+00 | 97.3% |
| LAB22 | 11062.1 | 0.29 | 3.0E−06 | 77.5% |
| LAB22 | 11063.4 | 0.25 | 8.5E−03 | 55.1% |
| LAB22 | 11064.1 | 0.21 | 3.2E−02 | 29.1% |
| LAB22 | 11064.6 | 0.31 | 0.0E+00 | 92.7% |
| LAB41 | 11551.4 | 0.20 | 4.0E−02 | 22.1% |
| Control | | 0.16 | | 0.0% |
| LAB40 | 11154.1 | 0.39 | 5.1E−03 | 31.3% |
| LAB49 | 11281.6 | 0.38 | 9.4E−03 | 29.2% |
| LAB35 | 11461.2 | 0.39 | 6.0E−03 | 31.7% |
| Control | | 0.29 | | 0.0% |

Table 40: Analyses of relative growth rate (RGR) of rosette area and diameter of transgenic plants overexpressing the exogenous polynucleotides of some embodiments of the invention (using the cloned or synthetic genes listed in Table 10 above) under the regulation of a constitutive promoter (At6669; SEQ ID NO: 674) when grown under normal conditions as compared to control plants. "Incr." = increment with respect to a control plant which has been transformed with an empty vector. Ave. = Average calculated from several transgenic events. "Event #" = number of event (transgenic transformation).

TABLE 41

Transgenic *Arabidopsis* plants exogenously expressing the polynucleotides of some embodiments of the invention exhibit improved plant biomass and growth rate under normal conditions

| Gene Name | Event # | Ave. | p-value | % incr. |
|---|---|---|---|---|
| RGR of plot coverage | | | | |
| LAB16 | 11032.5 | 2.64 | 9.2E−04 | 121.8% |
| LAB16 | 11033.2 | 3.14 | 0.0E+00 | 163.5% |
| LAB22 | 11062.1 | 2.40 | 4.3E−05 | 101.9% |
| LAB22 | 11063.4 | 2.30 | 7.0E−03 | 93.7% |
| LAB22 | 11064.1 | 1.71 | 4.9E−02 | 43.5% |
| LAB22 | 11064.6 | 3.11 | 0.0E+00 | 161.4% |
| Control | | 1.19 | | 0.0% |
| LAB17 | 11534.1 | 5.31 | 4.6E−02 | 60.4% |
| Control | | 3.31 | | 0.0% |
| LAB40 | 11151.1 | 3.33 | 2.6E−02 | 42.0% |
| LAB40 | 11154.1 | 4.12 | 7.6E−04 | 75.6% |
| LAB39 | 11182.1 | 3.24 | 3.6E−02 | 38.3% |
| LAB49 | 11281.6 | 3.41 | 2.0E−02 | 45.4% |
| LAB5 | 11443.3 | 3.36 | 2.1E−02 | 43.5% |
| LAB5 | 11444.1 | 3.39 | 2.2E−02 | 44.5% |
| LAB5 | 11444.5 | 3.59 | 1.9E−02 | 53.3% |
| LAB35 | 11461.2 | 4.45 | 1.6E−04 | 89.8% |
| Control | | 2.34 | | 0.0% |

Table 41: Analyses of relative growth rate (RGR) of plot coverage of transgenic plants overexpressing the exogenous polynucleotides of some embodiments of the invention (using the cloned or synthetic genes listed in Table 10 above) under the regulation of a constitutive promoter (At6669; SEQ ID NO: 674) when grown under normal conditions as compared to control plants. "Incr." = increment with respect to a control plant which has been transformed with an empty vector. Ave. = Average calculated from several transgenic events. "Event #" = number of event (transgenic transformation).

Tables 42-46 depict analyses of plant biomass and photosynthetic area (fresh weight, dry weight, rosette diameter, rosette area and plot coverage) when grown under normal conditions in plants overexpressing the polynucleotides of some embodiments of the invention under the regulation of a constitutive promoter (35S; SEQ ID NO:675). Evaluation of each gene was performed by testing the performance of several events. Some of the genes were evaluated in more than one tissue culture assay and the results obtained were repeated. Event with p-value<0.05 was considered statistically significant.

TABLE 42

Transgenic *Arabidopsis* plants exogenously expressing the polynucleotides of some embodiments of the invention exhibit improved plant biomass under normal conditions

| Gene Name | Event # | Ave. | p-value | % incr. |
|---|---|---|---|---|
| Fresh weight (g) | | | | |
| BDL210 | 10834.3 | 1.83 | 4.6E−02 | 17.1% |
| Control | | 1.56 | | 0.0% |
| CTF226 | 10985.2 | 1.90 | 4.3E−02 | 10.7% |
| Control | | 1.72 | | 0.0% |
| Dry weight (g) | | | | |
| BDL210 | 10831.3 | 0.16 | 3.9E−02 | 16.4% |
| BDL210 | 10833.1 | 0.19 | 4.5E−02 | 32.0% |
| BDL210 | 10834.3 | 0.17 | 8.8E−03 | 23.1% |
| Control | | 0.14 | | 0.0% |

Table 42: Analyses of fresh and dry weight of transgenic plants overexpressing the exogenous polynucleotides of some embodiments of the invention (using the cloned or synthetic genes listed in Table 10 above) under the regulation of a constitutive promoter (35S; SEQ ID NO: 675) when grown under noraml conditions as compared to control plants, "g" = grams. "Incr." = increment with respect to a control plant which has been transformed with an empty vector. Ave. = Average calculated from several transgenic events. "Event #" = number of event (transgenic transformation).

TABLE 43

Transgenic *Arabidopsis* plants exogenously expressing the polynucleotides of some embodiments of the invention exhibit improved plant biomass normal conditions

| Gene Name | Event # | Ave. | p-value | % incr. |
|---|---|---|---|---|
| Rosette diameter (cm) | | | | |
| BDL210 | 10831.3 | 3.65 | 2.7E−02 | 6.5% |
| Control | | 3.43 | | 0.0% |
| Rosette area (cm²) | | | | |
| BDL210 | 10831.3 | 4.21 | 1.5E−02 | 16.9% |
| BDL210 | 10834.2 | 4.21 | 4.8E−02 | 17.0% |
| Control | | 3.60 | | 0.0% |

Table 43: Analyses of rosette diameter and area of transgenic plants overexpressing the exogenous polynucleotides of some embodiments of the invention (using the cloned or synthetic genes listed in Table 10 above) under the regulation of a constitutive promoter (35S; SEQ ID NO: 675) when grown under normal conditions as compared to control plants. "Incr." = increment with respect to a control plant which has been transformed with an empty vector. Ave. = Average calculated from several transgenic events. "Event #" = number of event (transgenic transformation).

TABLE 44

Transgenic *Arabidopsis* plants exogenously expressing the polynucleotides of some embodiments of the invention exhibit improved plant biomass under normal conditions

| Gene Name | Event # | Ave. | p-value | % incr. |
|---|---|---|---|---|
| Plot coverage (cm²) | | | | |
| BDL210 | 10831.3 | 33.67 | 1.5E−02 | 16.9% |
| BDL210 | 10834.2 | 33.70 | 4.8E−02 | 17.0% |
| | | 28.80 | | 0.0% |
| Leaf number | | | | |
| BDL210 | 10833.1 | 9.31 | 6.4E−03 | 6.2% |
| Control | | 8.77 | | 0.0% |

Table 44: Analyses of plot coverage and leaf number of transgenic plants overexpressing the exogenous polynucleotides of some embodiments of the invention (using the cloned or synthetic genes listed in Table 10 above) under the regulation of a constitutive promoter (35S; SEQ ID NO: 675) when grown under normal conditions as compared to control plants. "Incr." = increment with respect to a control plant which has been transformed with an empty vector. Ave. = Average calculated from several transgenic events. "Event #" = number of event (transgenic transformation).

TABLE 45

Transgenic plants exogenously expressing the polynucleotides of some embodiments of the invention exhibit improved plant biomass under normal conditions

| Gene Name | Event # | Ave. | p-value | % incr. |
|---|---|---|---|---|
| RGR of rosette area | | | | |
| BDL210 | 10833.1 | 0.81 | 2.4E−03 | 66.5% |
| Control | | 0.49 | | 0.0% |
| RGR of rosette diameter | | | | |
| BDL210 | 10833.1 | 0.46 | 3.8E−02 | 21.9% |
| Control | | 0.38 | | 0.0% |

Table 45: Analyses of relative growth rate (RGR) of rosette area and diameter of transgenic plants overexpressing the exogenous polynucleotides of some embodiments of the invention (using the cloned or synthetic genes listed in Table 10 above) under the regulation of a constitutive promoter (35S; SEQ ID NO: 675) when grown under normal conditions as compared to control plants. "Incr." = increment with respect to a control plant which has been transformed with an empty vector. Ave. = Average calculated from several transgenic events. "Event #" = number of event (transgenic transformation).

TABLE 46

Transgenic *Arabidopsis* plants exogenously expressing the polynucleotides of some embodiments of the invention exhibit improved plant biomass under normal conditions
RGR of plot coverage

| Gene Name | Event # | Ave. | p-value | % incr. |
|---|---|---|---|---|
| BDL210 | 10833.1 | 6.50 | 2.4E−03 | 66.5% |
| Control | | 3.90 | | 0.0% |

Table 46: Analyses of relative growth rate (RGR) of plot coverage of transgenic plants overexpressing the exogenous polynucleotides of some embodiments of the invention (using the cloned or synthetic genes listed in Table 10 above) under the regulation of a constitutive promoter (35S SEQ ID NO: 675) when grown under normal conditions as compared to control plants.
"Incr." = increment with respect to a control plant which has been transformed with an empty vector.
Ave. = Average calculated from several transgenic events.
"Event #" = number of event (transgenic transformation).

Example 9

Improved Transgenic Plant Performance Under Normal Conditions

To analyze whether the transgenic plants has performed better, plants were grown in pots with an adequate amount of nutrient and water. The plants were analyzed for their overall size, growth rate, time to inflorescence emergence (bolting) and flowering, seed yield, oil content of seed, weight of 1,000 seeds, dry matter and harvest index (HI—seed yield/dry matter). Transgenic plants performance was compared to control plants grown in parallel under the same conditions. Mock-transgenic plants expressing the uidA reporter gene (GUS-Intron) under the same promoter were used as control.

Parameters were measured as described in Examples 6, 7 and 8 above.

Statistical Analyses

To identify genes conferring significantly improved plant performance, the results obtained from the transgenic plants were compared to those obtained from control plants. Plant growth rate, plant area, time to bolt, time to flower, weight of 1,000 seeds, seed yield, total yield, oil yield, oil percent in seeds, dry matter, harvest index, rosette area and growth rate data were analyzed using one-way ANOVA. To identify out-performing genes and constructs, results from mix of transformation events or independent events tested were analyzed. The Least Mean Squares were calculated for each experiment. For gene versus control analysis T-test was applied, using significance of p<0.05. The JMP statistics software package was used (Version 5.2.1, SAS Institute Inc., Cary, N.C., USA).

Experimental Results

The polynucleotide sequences of the invention were assayed for a number of commercially desired traits.

Tables 47-57 depict analyses of seed yield (Table 47), oil yield (Table 48), dry matter (Table 49), harvest index (HI) (Tables 50 and 51), growth rate (Table 52), rosette area (Table 53), oil % in seed (Table 54), weight of 1000 seeds (Tables 55 and 56) and total yield (Table 57) in plants overexpressing the polynucleotides of some embodiments of the invention under the regulation of a constitutive (35S; SEQ ID NO:675) or a seed specific (napin; SEQ ID NO:676) promoter. Each Table represents an independent experiment, using at least 5 independent events per gene. Genes not connected by same letter as the control (A, B) are significantly different (p<0.05) from the control.

TABLE 47

Genes showing improved plant performance *Arabidopsis*: Seed yield

| Gene Id | Under regulation of | Least Mean Sq | Significance (t-Test compare to control) | % improvement |
|---|---|---|---|---|
| BDL11 | 35S | 0.420 | A | 4.2 |
| BDL17 | 35S | 0.426 | A | 5.8 |
| CONTROL (GUS Intron) | 35S | 0.403 | A | 0.0 |
| BDL12 | 35S | 0.319 | B | 9.7 |
| BDL14 | 35S | 0.378 | A | 30.3 |
| CONTROL (GUS Intron) | 35S | 0.290 | B | 0.0 |

Table 47: Analyses of seed yield per plant of transgenic plants overexpressing the exogenous polynucleotides of some embodiments of the invention (using the cloned or synthetic genes listed in Table 10 above) under the regulation of a constitutive promoter (35S promoter; SEQ ID NO: 675) when grown under normal conditions as compared to control plants.
"Least Mean Sq" = Least Mean Square.
"% improvement" relates to improvement of transgenic plant seed yield as compared to control plants that have been transformed with a vector comprising GUS intron under the transcriptional regulation of the same promoter.

TABLE 48

Genes showing improved plant performance *Arabidopsis*: Oil yield

| Gene Id | Under regulation of | Least Mean Sq | Significance (t-Test compare to control) | % improvement |
|---|---|---|---|---|
| BDL11 | 35S | 0.12 | A | 7.0 |
| BDL17 | 35S | 0.12 | A | 6.5 |
| CONTROL (GUS Intron) | 35S | 0.12 | A | 0.0 |
| BDL12 | 35S | 0.100 | B | 14.2 |
| BDL14 | 35S | 0.114 | A | 31.1 |
| CONTROL (GUS Intron) | 35S | 0.087 | B | 0.0 |

Table 48: Analyses of oil yield per plant of transgenic plants overexpressing the exogenous polynucleotides of some embodiments of the invention (using the cloned or synthetic genes listed in Table 10 above) under the regulation of a constitutive promoter (35S promoter; SEQ ID NO: 675) when grown under normal conditions as compared to control plants.
"Least Mean Sq" = Least Mean Square.
"% improvement" relates to improvement of transgenic plant oil yiel as compared to control plants that have been transformed with a vector comprising GUS intron under the transcriptional regulation of the same promoter.

TABLE 49

Genes showing improved plant performance *Arabidopsis*: Dry matter

Dry matter per plant (gr)

| Gene Id | Under regulation of | Least Mean Sq | Significance (t-Test compare to control) | % improvement |
|---|---|---|---|---|
| BDL14 | 35S | 1.0444 | A | 9.7 |
| CONTROL (GUS Intron) | 35S | 0.9523 | A | 0.0 |
| BDL11 | 35S | 1.3638 | A | 1.2 |
| CONTROL (GUS Intron) | 35S | 1.3474 | A | 0.0 |

Table 49. Analyses of dry matter per plant of transgenic plants overexpressing the exogenous polynucleotides of some embodiments of the invention (using the cloned or synthetic genes listed in Table 10 above) under the regulation of a constitutive promoter (35S promoter; SEQ ID NO: 675) when grown under normal conditions as compared to control plants.
"Least Mean Sq" = Least Mean Square.
"% improvement" relates to improvement of transgenic plant dry matter as compared to control plants that have been transformed with a vector comprising GUS intron under the transcriptional regulation of the same promoter.

TABLE 50

Genes showing improved plant performance *Arabidopsis*: harvest index (HI)

HI

| Gene Id | Under regulation of | Least Mean Sq | Significance (t-Test compare to control) | % improvement |
|---|---|---|---|---|
| BDL11 | 35S | 0.3063 | B | 2.0 |
| BDL17 | 35S | 0.3526 | A | 17.5 |
| CONTROL (GUS Intron) | 35S | 0.3002 | B | 0.0 |

Table 50. Analyses of harvest index of transgenic plants overexpressing the exogenous polynucleotides of some embodiments of the invention (using the cloned or synthetic genes listed in Table 10 above) under the regulation of a constitutive promoter (35S promoter; SEQ ID NO: 675) when grown under normal conditions as compared to control plants.
"Least Mean Sq" = Least Mean Square.
"% improvement" relates to improvement of transgenic harvest index as compared to control plants that have been transformed with a vector comprising GUS intron under the transcriptional regulation of the same promoter.

TABLE 51

Genes showing improved plant performance *Arabidopsis*: Harvest index

Harvest index

| Gene Id | Under regulation of | Mean | Significance (t-Test compare to control) | % improvement |
|---|---|---|---|---|
| BDL103 | 35S | 0.341 | A | 16.8 |
| CONTROL (GUS Intron) | 35S | 0.292 | B | 0 |

Table 51. Analyses of harvest index of transgenic plants overexpressing the exogenous polynucleotides of some embodiments of the invention (using the cloned or synthetic genes listed in Table 10 above) under the regulation of a constitutive promoter (35S promoter; SEQ ID NO: 675) when grown under normal conditions as compared to control plants.
"Least Mean Sq" = Least Mean Square.
"% improvement" relates to improvement of transgenic plant harvest index as compared to control plants that have been transformed with a vector comprising GUS intron under the transcriptional regulation of the same promoter.

TABLE 52

Genes showing improved plant performance *Arabidopsis*: Growth rate

| Gene Id | Under regulation of | Least Mean Sq | Significance (t-Test compare to control) | % improvement |
|---|---|---|---|---|
| BDL14 | 35S | 2.48 | A | 6.4 |
| CONTROL (GUS Intron) | 35S | 2.33 | A | 0.0 |
| BDL11 | 35S | 1.80 | A | 15.4 |
| CONTROL (GUS Intron) | 35S | 1.56 | A | 0.0 |
| BDL12 | 35S | 1.58 | B | 2.0 |
| BDL14 | 35S | 1.95 | A | 26.3 |
| CONTROL (GUS Intron) | 35S | 1.55 | B | 0.0 |

Table 52. Analyses of growth rate of transgenic plants overexpressing the exogenous polynucleotides of some embodiments of the invention (using the cloned or synthetic genes listed in Table 10 above) under the regulation of a constitutive promoter (35S promoter; SEQ ID NO: 675) when grown under normal conditions as compared to control plants.
"Least Mean Sq" = Least Mean Square.
"% improvement" relates to improvement of transgenic plant growth rate as compared to control plants that have been transformed with a vector comprising GUS intron under the transcriptional regulation of the same promoter.

TABLE 53

Genes showing improved plant performance *Arabidopsis*: Rosette area

| Gene Id | Under regulation of | Least Mean Sq | Significance (t-Test compare to control) | % improvement |
|---|---|---|---|---|
| BDL14 | 35S | 11.83 | A | 9.2 |
| CONTROL (GUS Intron) | 35S | 10.83 | B | 0.0 |
| BDL11 | 35S | 14.09 | A | 13.2 |
| CONTROL (GUS Intron) | 35S | 12.44 | A | 0.0 |
| BDL12 | 35S | 7.92 | B | −2.5 |
| BDL14 | 35S | 9.96 | A | 22.7 |
| CONTROL (GUS Intron) | 35S | 8.12 | B | 0.0 |

Table 53: Analyses of rosette area of transgenic plants overexpressing the exogenous polynucleotides of some embodiments of the invention (using the cloned or synthetic genes listed in Table 10 above) under the regulation of a constitutive promoter (35S promoter; SEQ ID NO: 675) when grown under normal conditions as compared to control plants.
"Least Mean Sq" = Least Mean Square.
"% improvement" relates to improvement of transgenic plant rosette area as compared to control plants that have been transformed with a vector comprising GUS intron under the transcriptional regulation of the same promoter. It should be noted that an increase in rosette area means better soil coverage and reduced water loss from soil. Decrease in rosette area means more plants could be put per area increasing yield.

TABLE 54

Genes showing improved plant performance *Arabidopsis*: oil % in seed

| Gene Id | Under regulation of | Least Mean Sq | Significance (t-Test compare to control) | % improvement |
|---|---|---|---|---|
| BDL14 | 35S | 31.31 | A | 3.1 |
| CONTROL (GUS Intron) | 35S | 30.355 | A | 0.0 |
| BDL11 | 35S | 29.216 | A | 1.5 |
| BDL17 | 35S | 28.904 | A | 0.4 |
| CONTROL (GUS Intron) | 35S | 28.78 | A | 0 |
| BDL12 | 35S | 31.30 | A | 3.7 |
| BDL14 | 35S | 30.27 | A | 0.3 |
| CONTROL (GUS Intron) | 35S | 30.19 | A | 0.0 |

Table 54. Analyses of oil percent in seed of transgenic plants overexpressing the exogenous polynucleotides of some embodiments of the invention (using the cloned or synthetic genes listed in Table 10 above) under the regulation of a constitutive promoter (35S promoter; SEQ ID NO: 675) when grown under normal conditions as compared to control plants.
"Least Mean Sq" = Least Mean Square.
"% improvement" relates to improvement of transgenic plant oil percent in seed as compared to control plants that have been transformed with a vector comprising GUS intron under the transcriptional regulation of the same promoter.

TABLE 55

Genes showing improved plant performance *Arabidopsis*: weight of 1,000 seeds

| Gene Id | Under regulation of | Least Mean Sq | Significance (t-Test compare to control) | % improvement |
|---|---|---|---|---|
| BDL14 | 35S | 0.019 | B | 6.1 |
| CONTROL (GUS Intron) | 35S | 0.018 | B | 0.0 |
| BDL11 | 35S | 0.0235 | A | 15.7 |
| CONTROL (GUS Intron) | 35S | 0.0203 | B | 0 |
| BDL12 | 35S | 0.0234 | A | 0.1 |
| CONTROL (GUS Intron) | 35S | 0.0234 | A | 0.0 |

Table 55. Analyses of weight of 1,000 seeds of transgenic plants overexpressing the exogenous polynucleotides of some embodiments of the invention (using the cloned or synthetic genes listed in Table 10 above) under the regulation of a constitutive promoter (35S promoter; SEQ ID NO: 675) when grown under normal conditions as compared to control plants.
"Least Mean Sq" = Least Mean Square.
"% improvement" relates to improvement of transgenic plant weight of 1,000 seeds as compared to control plants that have been transformed with a vector comprising GUS intron under the transcriptional regulation of the same promoter.

TABLE 56

Genes showing improved plant performance *Arabidopsis*: weight of 1,000 seeds

| Gene Id | Under regulation of | Least Mean Sq | Significance (t-Test compare to control) | % improvement |
|---|---|---|---|---|
| BDL14 | Napin | 0.0227 | A | 2.3 |
| CONTROL (GUS Intron) | Napin | 0.0222 | A | 0.0 |
| BDL12 | Napin | 0.0206 | A | 0.2 |
| CONTROL (GUS Intron) | Napin | 0.0205 | A | 0.0 |

Table 56. Analyses of weight of 1,000 seeds of transgenic plants overexpressing the exogenous polynucleotides of some embodiments of the invention (using the cloned or synthetic genes listed in Table 10 above) under the regulation of a seed specific napin promoter (SEQ ID NO: 675) when grown under normal conditions as compared to control plants.
"Least Mean Sq" = Least Mean Square.
"% improvement" relates to improvement of transgenic plant weight of 1,000 seeds as compared to control plants that have been transformed with a vector comprising GUS intron under the transcriptional regulation of the same promoter.

TABLE 57

Genes showing improved plant performance *Arabidopsis*: total yield

| | | total yield (gr/plant) | | |
|---|---|---|---|---|
| Gene Id | Under regulation of | Mean | Significance (t-Test compare to control) | % improvement |
| BDL103 | 35S | 0.305 | A | 10.1 |
| CONTROL (GUS Intron) | 35S | 0.277 | B | 0 |

Table 57. Analyses of total yield per plant of transgenic plants overexpressing the exogenous polynucleotides of some embodiments of the invention (using the cloned or synthetic genes listed in Table 10 above) under the regulation of a constitutive promoter (35S promoter; SEQ ID NO: 675) when grown under normal conditions as compared to control plants. "Least Mean Sq" = Least Mean Square.
"% improvement" relates to improvement of transgenic plant total yield as compared to control plants that have been transformed with a vector comprising GUS intron under the transcriptional regulation of the same promoter.

Example 10

Transgenic *Arabidosis* which Exogenously Express BDL103 Exhibit Increased Commercially Desired Traits in a Tissue Culture Assay Nitrogen Use Efficiency Tissue culture assays were performed as described in Example 6 hereinabove for determining plant performance under normal (i.e., 15 mM nitrogen) or nitrogen deficiency (i.e., 0.75 mM nitrogen) conditions.

Abiotic Stress Tolerance

To determine whether the transgenic plants exhibit increased tolerance to abiotic stress such as drought, an osmotic stress was induced by adding sorbitol or polyethylene glycol (PEG 8000) to the culturing medium. Control and transgenic plants were germinated and grown in plant-agar plates for 10 days, after which they were transferred to plates containing either 1.5% PEG8000 or 500 mM of sorbitol. Plants were grown under the osmotic stress conditions or the normal conditions for about additional 10 days, during which various parameters which indicate plant characteristics were measured. The measured parameters [e.g., plant weight (fresh and dry), yield, growth rate] were compared between the control and transgenic plants.

Tables 58-60 depict analyses of root coverage, root length, growth rate of root coverage, growth rate of root length and biomass in plants overexpressing the BDL103-short (SEQ ID NO:671) and BDL103-long (SEQ ID NO:670) polynucleotides under the regulation of a constitutive (35S; SEQ ID NO:675) when grown under normal conditions (Table 58), under nitrogen limiting conditions (Table 59), or under osmotic stress (15% PEG). Each Table includes data of several transformation events per gene. Results were considered significant if p-value was lower than 0.1 when compared to control plants (which were transformed with a vector containing GUS reporter gene).

TABLE 58

Improved growth rate, root coverage, root length and biomass in transgenic *Arabidopsis* plants exogenously expressing BDL103 under normal conditions

| | | BDL103 Long or Short/Event No. | | | | | | | | | |
|---|---|---|---|---|---|---|---|---|---|---|---|
| | | Long/ 3054 | Long/ 3055 | Long/ 3056 | Long/ 3057 | Long/ 3058 | Short/ 3060 | Short/ 3061 | Short/ 3062 | Short/ 3063 | Short/ 3064 |
| Roots Coverage (time point 1) | P A | | | | | 0.10 1.21 | | | | | |
| Roots Coverage (time point 6) | P A | | 0.08 1.36 | | | 0.25 1.12 | | | | | |
| Roots Coverage (time point 9) | P A | | 0.07 1.23 | | | | | | | | |
| Roots Length (time point 1) | P A | | | | | 0.03 1.19 | | | | | |
| Roots Length (time point 6) | P A | | 0.05 1.17 | | | 0.22 1.10 | | | | | |
| Roots Length (time point 9) | P A | | 0.01 1.15 | | | | | | | | |
| GR (growth rate) of Roots Coverage (time point 6) | P A | | 0.07 1.47 | | | 0.46 1.10 | | | | | |
| GR of Roots Length (time point 6) | P A | | 0.04 1.31 | | | | | | | | |
| RGR of Roots Coverage (time point 6) | P A | | 0.06 1.56 | 0.70 1.16 | | | | | 0.13 1.31 | 0.02 1.49 | 0.10 1.28 |
| RGR of Roots Coverage (time point 9) | P A | | | | | | | 0.23 1.87 | | | |
| RGR of Roots Length (time point 6) | P A | | 0.08 1.37 | 0.74 1.11 | | | | | | 0.21 1.16 | 0.11 1.13 |
| RGR of Roots Length (time point 9) | P A | | | | | | | 0.23 1.62 | | 0.41 1.12 | |
| DW [gr] (time point 1) | P A | | 0.56 1.13 | | | | | | | | |

TABLE 58-continued

Improved growth rate, root coverage, root length and biomass in transgenic
*Arabidopsis* plants exogenously expressing BDL103 under normal conditions

| | | Long/ 3054 | Long/ 3055 | Long/ 3056 | Long/ 3057 | Long/ 3058 | Short/ 3060 | Short/ 3061 | Short/ 3062 | Short/ 3063 | Short/ 3064 |
|---|---|---|---|---|---|---|---|---|---|---|---|
| DW [gr] (time point 6) | P | | 0.56 | | | | | | | | |
| | A | | 1.13 | | | | | | | | |
| DW [gr] (time point 9) | P | | 0.56 | | | | | | | | |
| | A | | 1.13 | | | | | | | | |

Table 58. Analysis of growth parameters in tissue culture conditions of transgenic plants overexpressing BDL103-Short polynucleotide (SEQ ID NO: 671) or BDL103-Long polynucleotide (SEQ ID NO: 670) under the regulation of a constitutive promoter (35S; SEQ ID NO: 675) when grown under normal conditions (15 mM nitrogen). Each event number refers to an independent transformation event in a plant (i.e., generation of a transgenic plant expressing the polynucleotide of choice). "A" = average; "P" = p-value; "GR" = growth rate; "RGR" = relative growth rate; "DW" = dry weight; "gr" = grams; Root coverage is presented in $cm^2$; root length is presented in cm; GR of root length is presented in cm/day; RGR of root length is presented in cm/day; RGR of root coverage is presented in $cm^2$/day. The various time points indicate days from beginning of experiment in which parameters were measured.

TABLE 59

Improved growth rate, root coverage, root length and biomass in transgenic
plants exogenously expressing BDL103 under nitrogen limiting conditions

| | | Long/ 3054 | Long/ 3055 | Long/ 3056 | Long/ 3057 | Long/ 3058 | Short/ 3060 | Short/ 3061 | Short/ 3062 | Short/ 3063 | Short/ 3064 |
|---|---|---|---|---|---|---|---|---|---|---|---|
| Roots Coverage (time point 6) | P | | 0.34 | | | 0.03 | | | | | |
| | A | | 1.10 | | | 1.26 | | | | | |
| Roots Coverage (time point 9) | P | | 0.05 | | | 0.00 | | | 0.27 | | |
| | A | | 1.19 | | | 1.40 | | | 1.18 | | |
| Roots Length (time point 1) | P | | | | | 0.04 | | | | | |
| | A | | | | | 1.11 | | | | | |
| Roots Length (time point 6) | P | | | | | 0.00 | | | | | |
| | A | | | | | 1.20 | | | | | |
| Roots Length (time point 9) | P | | 0.01 | | | 0.00 | | | | | |
| | A | | 1.14 | | | 1.25 | | | | | |
| GR of Roots Coverage (time point 6) | P | | 0.21 | | | 0.03 | | | | | |
| | A | | 1.19 | | | 1.31 | | | | | |
| GR of Roots Coverage (time point 9) | P | 0.53 | 0.09 | | 0.37 | 0.01 | | | 0.14 | 0.34 | |
| | A | 1.19 | 1.37 | | 1.27 | 1.70 | | | 1.66 | 1.26 | |
| GR of Roots Length (time point 6) | P | | 0.11 | | | 0.01 | | | | | |
| | A | | 1.21 | | | 1.25 | | | | | |
| GR of Roots Length (time point 9) | P | | 0.06 | | 0.09 | 0.01 | | | 0.07 | 0.37 | |
| | A | | 1.28 | | 1.28 | 1.39 | | | 1.39 | 1.11 | |
| RGR of Roots Coverage (time point 6) | P | | 0.08 | | 0.00 | 0.21 | | 0.06 | 0.04 | | 0.00 |
| | A | | 1.55 | | 1.69 | 1.20 | | 1.39 | 1.57 | | 1.91 |
| RGR of Roots Coverage (time point 9) | P | 0.04 | 0.33 | 0.11 | 0.22 | 0.23 | 0.14 | 0.45 | 0.13 | 0.02 | 0.31 |
| | A | 2.06 | 1.23 | 1.95 | 1.43 | 1.32 | 1.52 | 1.23 | 1.71 | 2.53 | 1.50 |
| RGR of Roots Length (time point 6) | P | | 0.07 | | 0.01 | 0.32 | | 0.31 | 0.12 | | 0.05 |
| | A | | 1.34 | | 1.39 | 1.11 | | 1.14 | 1.24 | | 1.39 |
| RGR of Roots Length (time point 9) | P | 0.21 | 0.38 | 0.21 | 0.06 | 0.33 | 0.19 | 0.33 | 0.06 | 0.08 | 0.55 |
| | A | 1.35 | 1.15 | 1.27 | 1.32 | 1.13 | 1.29 | 1.22 | 1.40 | 1.67 | 1.22 |
| DW [gr] (time point 1) | P | | 0.13 | | | | | | | | |
| | A | | 1.22 | | | | | | | | |
| DW [gr] (time point 6) | P | | 0.13 | | | | | | | | |
| | A | | 1.22 | | | | | | | | |

TABLE 59-continued

Improved growth rate, root coverage, root length and biomass in transgenic plants exogenously expressing BDL103 under nitrogen limiting conditions

| | | \multicolumn{9}{c}{BDL103 Long or Short/Event No.} |
|---|---|---|---|---|---|---|---|---|---|---|

| | | Long/ 3054 | Long/ 3055 | Long/ 3056 | Long/ 3057 | Long/ 3058 | Short/ 3060 | Short/ 3061 | Short/ 3062 | Short/ 3063 | Short/ 3064 |
|---|---|---|---|---|---|---|---|---|---|---|---|
| DW [gr] | P | | 0.13 | | | | | | | | |
| (time point 9) | A | | 1.22 | | | | | | | | |

Table 59. Analysis of growth parameters in tissue culture conditions of transgenic plants overexpressing BDL103-Short polynucleotide (SEQ ID NO: 671) or BDL103-Long polynucleotide (SEQ ID NO: 670) under the regulation of a constitutive promoter (35S; SEQ ID NO: 675) when grown under nitrogen limiting conditions (N 0.75 mM; see example 6). Each event number refers to an independent transformation event in a plant (i.e., generation of a transgenic plant expressing the polynucleotide of choice). "A" = average; "P" = p-value; "RGR" = relative growth rate; "DW" = dry weight; "gr" = grams; Root coverage is presented in $cm^2$; root length is presented in cm; GR of root length is presented in cm/day; RGR of root length is presented in cm/day; RGR of root coverage is presented in $cm^2$/day. The various time points indicate days from beginning of experiment in which parameters were measured.

TABLE 60

Improved growth rate, root coverage, root length and biomass in transgenic plants exogenously expressing BDL103 under osmotic stress conditions

| | | Long/ 3054 | Long/ 3055 | Long/ 3056 | Long/ 3057 | Long/ 3058 | Short/ 3060 | Short/ 3061 | Short/ 3062 | Short/ 3063 | Short/ 3064 |
|---|---|---|---|---|---|---|---|---|---|---|---|
| Roots Coverage (time point 9) | P | | | | | | | | 0.08 | 0.08 | |
| | A | | | | | | | | 1.25 | 1.34 | |
| Roots Length (time point 9) | P | | | | | | | | 0.08 | 0.03 | |
| | A | | | | | | | | 1.13 | 1.26 | |
| GR of Roots Coverage (time point 6) | P | | 0.32 | | | | | | 0.06 | 0.13 | |
| | A | | 1.19 | | | | | | 1.23 | 1.23 | |
| GR of Roots Coverage (time point 9) | P | | 0.39 | | | 0.28 | | | 0.04 | 0.04 | |
| | A | | 1.22 | | | 1.20 | | | 1.65 | 1.96 | |
| GR of Roots Length (time point 6) | P | | 0.11 | | | | | | 0.03 | 0.05 | |
| | A | | 1.25 | | | | | | 1.27 | 1.40 | |
| GR of Roots Length (time point 9) | P | | 0.09 | | | 0.02 | | | 0.01 | 0.02 | |
| | A | | 1.23 | | | 1.28 | | | 1.45 | 1.80 | |
| RGR of Roots Coverage (time point 6) | P | | 0.00 | | | | | | 0.01 | 0.05 | 0.68 |
| | A | | 2.12 | | | | | | 1.84 | 2.14 | 1.16 |
| RGR of Roots Coverage (time point 9) | P | | 0.46 | 0.04 | 0.27 | 0.24 | 0.56 | | 0.02 | 0.01 | 0.63 |
| | A | | 1.26 | 1.42 | 1.20 | 1.67 | 1.24 | | 1.50 | 1.80 | 1.26 |
| RGR of Roots Length (time point 6) | P | | 0.00 | | | | | | 0.00 | 0.05 | |
| | A | | 1.64 | | | | | | 1.57 | 1.76 | |
| RGR of Roots Length (time point 9) | P | | 0.18 | 0.09 | | 0.03 | 0.57 | 0.15 | 0.01 | 0.02 | |
| | A | | 1.26 | 1.28 | | 1.21 | 1.23 | 1.32 | 1.40 | 1.65 | |
| DW [gr] (time point 1) | P | | | 0.04 | | | | | 0.05 | 0.41 | |
| | A | | | 1.41 | | | | | 1.30 | 1.22 | |
| DW [gr] (time point 6) | P | | | 0.04 | | | | | 0.05 | 0.41 | |
| | A | | | 1.41 | | | | | 1.30 | 1.22 | |
| DW [gr] (time point 9) | P | | | 0.04 | | | | | 0.05 | 0.41 | |
| | A | | | 1.41 | | | | | 1.30 | 1.22 | |
| FW [gr] (time point 1) | P | | 0.47 | | | | | | 0.17 | 0.30 | |
| | A | | 1.32 | | | | | | 1.23 | 1.36 | |
| FW [gr] (time point 6) | P | | 0.47 | | | | | | 0.17 | 0.30 | |
| | A | | 1.32 | | | | | | 1.23 | 1.36 | |
| FW [gr] (time point 9) | P | | 0.47 | | | | | | 0.17 | 0.30 | |
| | A | | 1.32 | | | | | | 1.23 | 1.36 | |

Table 60. Analysis of growth parameters in tissue culture conditions of transgenic plants overexpressing BDL103-Short polynucleotide (SEQ ID NO: 671) or BDL103-Long polynucleotide (SEQ ID NO: 670) under the regulation of a constitutive promoter (35S; SEQ ID NO: 675) when grown under osmotic stress condition in the presence of 15% PEG (polyethylene glycol). Each event number refers to an independent transformation event in a plant (i.e., generation of a transgenic plant expressing the polynucleotide of choice). "A" = average; "P" = p-value; "GR" = growth rate; "RGR" = relative growth rate; "DW" = dry weight; "FW" = fresh weight; "gr" = grams; Root coverage is presented in $cm^2$; root length is presented in cm; GR of root length is presented in cm/day; RGR of root length is presented in cm/day; RGR of root coverage is presented in $cm^2$/day. The various time points indicate days from beginning of experiment in which parameters were measured.

Example 11

Transgenic *Arabidopsis* Plants which Exogenously Express BDL103 Exhibit Increased Commercially Desired Traits in a Greenhouse Assay Greenhouse assays were performed as described in Example 7 hereinabove for determining plant performance under normal conditions (i.e., irrigation with tap water).

Tables 61-62 depict analyses of growth rate, biomass, rosette diameter, rosette area, plot coverage, leaf number, petiole relative area, leaf blade area, blade relative area and harvest index in plants overexpressing the BDL103-long (SEQ ID NO:670; Table 61) and the BDL103-short (SEQ ID NO:671; Table 62) polynucleotides under the regulation of a constitutive (35S; SEQ ID NO:675) when grown in a greenhouse under normal conditions until seed production. Each Table includes data of several transformation events per gene. Results were considered significant if p-value was lower than 0.1 when compared to control plants (transformed with an empty vector).

TABLE 61

Improved growth rate, biomass, rosette diameter, rosette area, plot coverage, leaf number, petiole relative area, leaf blade area, blade relative area and harvest index in transgenic *arabidopsis* plants exogenously expressing BDL103-long (SEQ ID NO: 670) under favorable conditions

| Parameter (time point) | Event No | | | | | | | | | |
|---|---|---|---|---|---|---|---|---|---|---|
| | 2541 A | 2541 P | 2542 A | 2542 P | 2543 A | 2543 P | 2545 A | 2545 P | 2546 A | 2546 P |
| Yield | 1.76 | 0.40 | 1.18 | 0.43 | 1.51 | 0.05 | 1.36 | 0.03 | | |
| Rosette Diameter (time point 8) | 1.11 | 0.18 | 1.37 | 0.03 | 1.33 | 0.10 | 1.14 | 0.41 | 1.12 | 0.65 |
| Rosette Diameter (time point 5) | 1.13 | 0.00 | 1.31 | 0.22 | 1.25 | 0.10 | 1.11 | 0.43 | 1.13 | |
| Rosette Diameter (time point 3) | | | 1.59 | 0.01 | 1.52 | 0.07 | 1.29 | 0.25 | 1.16 | 0.55 |
| Rosette Diameter (time point 1) | | | 1.20 | 0.08 | 1.19 | 0.30 | | | | |
| Rosette Area (time point 8) | 1.37 | 0.00 | 1.65 | 0.24 | 1.53 | 0.14 | 1.24 | 0.35 | | |
| Rosette Area (time point 5) | 1.23 | 0.12 | 1.48 | 0.17 | 1.25 | 0.19 | | | 1.21 | |
| Rosette Area (time point 3) | | | 1.97 | 0.16 | 1.68 | 0.06 | 1.37 | 0.38 | 1.23 | 0.60 |
| Rosette Area (time point 1) | 1.17 | 0.36 | 1.23 | 0.04 | | | | | | |
| RGR of Rosette Diameter (time point 8) | | | 1.13 | 0.54 | 1.14 | 0.07 | | | 1.38 | |
| RGR of Rosette Diameter (time point 5) | 9.61 | 0.11 | | | | | | | | |
| RGR of Rosette Diameter (time point 3) | | | 2.20 | 0.18 | 2.00 | 0.11 | 2.00 | 0.11 | 2.41 | 0.04 |
| RGR of Rosette Area (time point 8) | 1.18 | 0.36 | 1.15 | 0.30 | 1.32 | 0.00 | 1.19 | 0.00 | 1.19 | |
| RGR of Rosette Area (time point 5) | 6.59 | 0.29 | | | | | | | | |
| RGR of Rosette Area (time point 3) | | | 2.22 | 0.28 | 2.66 | 0.00 | 2.67 | 0.26 | 2.11 | 0.12 |
| RGR of Plot Coverage (time point 8) | 1.18 | 0.36 | 1.15 | 0.30 | 1.32 | 0.00 | 1.19 | 0.00 | 1.19 | |
| RGR of Plot Coverage (time point 5) | 6.59 | 0.29 | | | | | | | | |
| RGR of Plot Coverage (time point 3) | | | 2.22 | 0.28 | 2.66 | 0.00 | 2.67 | 0.26 | 2.11 | 0.12 |
| RGR of Leaf Number (time point 5) | 8.30 | 0.21 | | | | | | | | |
| RGR of Leaf Number (time point 3) | | | 1.39 | 0.44 | 2.59 | 0.01 | 3.00 | 0.33 | 2.37 | 0.02 |
| Plot Coverage (time point 8) | 1.40 | 0.00 | 1.59 | 0.34 | 1.55 | 0.13 | 1.26 | 0.32 | | |
| Plot Coverage (time point 5) | 1.24 | 0.10 | 1.42 | 0.32 | 1.27 | 0.17 | 1.11 | 0.53 | | |
| Plot Coverage (time point 3) | | | 1.90 | 0.26 | 1.71 | 0.05 | 1.39 | 0.36 | 1.15 | 0.64 |
| Plot Coverage (time point 1) | 1.19 | 0.33 | 1.17 | 0.09 | | | | | | |
| Petiole Relative Area (time point 8) | 1.31 | 0.81 | | | 1.23 | 0.66 | | | | |
| Petiole Relative Area (time point 3) | 2.69 | 0.02 | | | | | | | | |
| Petiole Relative Area (time point 1) | | | | | 1.18 | 0.43 | 1.42 | 0.00 | 1.39 | 0.26 |
| Leaf Petiole Area (time point 8) | 1.95 | 0.64 | | | 1.67 | 0.22 | | | | |
| Leaf Petiole Area (time point 3) | 3.05 | 0.00 | | | | | | | | |

TABLE 61-continued

Improved growth rate, biomass, rosette diameter, rosette area, plot coverage, leaf number, petiole relative area, leaf blade area, blade relative area and harvest index in transgenic *arabidopsis* plants exogenously expressing BDL103-long (SEQ ID NO: 670) under favorable conditions

| Parameter (time point) | 2541 A | 2541 P | 2542 A | 2542 P | 2543 A | 2543 P | 2545 A | 2545 P | 2546 A | 2546 P |
|---|---|---|---|---|---|---|---|---|---|---|
| Leaf Petiole Area (time point 1) | | | | | 1.11 | 0.61 | 1.33 | 0.01 | 1.18 | 0.49 |
| Leaf Number (time point 8) | | | 1.10 | 0.02 | 1.10 | 0.03 | | | | |
| Leaf Number (time point 5) | 1.07 | 0.05 | 1.12 | 0.15 | 1.11 | 0.28 | | | 1.12 | |
| Leaf Number (time point 3) | | | 1.50 | 0.02 | 1.43 | 0.12 | 1.25 | 0.40 | 1.28 | 0.29 |
| Leaf Number (time point 1) | 1.28 | 0.00 | 1.37 | 0.00 | | | | | | |
| Leaf Blade Area (time point 8) | 1.43 | 0.00 | 1.53 | 0.32 | 1.37 | 0.15 | 1.28 | 0.00 | | |
| Leaf Blade Area (time point 5) | 1.18 | 0.17 | 1.36 | 0.14 | 1.14 | 0.11 | | | 1.11 | |
| Leaf Blade Area (time point 3) | | | 1.59 | 0.20 | 1.41 | 0.02 | 1.31 | 0.14 | 1.14 | 0.59 |
| Harvest index | 1.19 | 0.01 | 1.18 | 0.38 | | | | | 1.13 | 0.08 |
| Blade Relative Area (time point 8) | | | | | | | 1.03 | 0.07 | | |
| Blade Relative Area (time point 5) | 1.03 | 0.05 | | | | | | | | |
| Blade Relative Area (time point 3) | | | 1.19 | 0.08 | 1.18 | 0.09 | 1.18 | 0.10 | 1.18 | 0.09 |
| Blade Relative Area (time point 1) | | | 1.11 | 0.01 | | | | | | |

Table 61. Analysis of growth parameters in a greenhouse assay of transgenic plants overexpressing BDL103-long polynucleotide (SEQ ID NO: 670) under the regulation of a constitutive promoter (35S; SEQ ID NO: 675) which were grown until seed production under normal conditions (as described in Example 7 above). Each event number refers to an independent transformation event in a plant (i.e., generation of a transgenic plant expressing the polynucleotide of choice). "A" = average; "P" = p-value; "RGR" = relative growth rate; "gr" = grams; yield is presented in mg/plant; Rosette Diameter is presented in cm/plant; Rosette Area is presented in $cm^2$/plant; RGR of Rosette Diameter is presented in cm/plant*day; RGR of Rosette Area is presented in $cm^2$/plant*day; RGR of Plot Coverage is presented in $cm^2$/plant*day; RGR of Leaf Number is presented in 1/day; Plot Coverage is presented in $cm^2$; Petiole Relative Area is presented in percent; Leaf Petiole Area is presented in $cm^2$; Leaf Number is presented as number of leaves per plant; Leaf Blade Area is presented in $cm^2$; Harvest Index is presented in g/DW (dry weight); Blade Relative Area is presented in percent; The various time points indicate days from beginning of experiment in which parameters were measured.

TABLE 62

Improved growth rate, biomass, rosette diameter, rosette area, plot coverage, leaf number, petiole relative area, leaf blade area, blade relative area and harvest index in transgenic *arabidopsis* plants exogenously expressing BDL103-short (SEQ ID NO: 671) under favorable conditions

| Parameter (time point) | 2353 A | 2353 P | 2357 A | 2357 P | 2359 A | 2359 P | 2360 A | 2360 P | 2361 A | 2361 P |
|---|---|---|---|---|---|---|---|---|---|---|
| Yield | 1.32 | 0.26 | 1.32 | 0.01 | 1.14 | 0.18 | | | | |
| Rosette Diameter (time point 8) | 1.28 | | 1.24 | 0.00 | 1.13 | 0.44 | 1.21 | 0.31 | 1.15 | 0.05 |
| Rosette Diameter (time point 5) | 1.26 | 0.07 | 1.15 | 0.13 | | | | | | |
| Rosette Diameter (time point 3) | 1.43 | 0.01 | 1.28 | 0.06 | 1.21 | 0.13 | 1.29 | 0.41 | 1.10 | 0.52 |
| Rosette Diameter (time point 1) | 1.26 | 0.29 | | | | | | | | |
| Rosette Area (time point 8) | 1.46 | | 1.36 | 0.00 | 1.12 | 0.10 | 1.32 | 0.39 | 1.15 | 0.23 |
| Rosette Area (time point 5) | 1.32 | 0.00 | 1.27 | 0.00 | | | 1.16 | 0.61 | | |
| Rosette Area (time point 3) | 1.36 | 0.10 | 1.56 | 0.02 | | | 1.31 | 0.63 | | |
| Rosette Area (time point 1) | 1.18 | 0.06 | | | | | | | | |
| RGR of Rosette Diameter (time point 8) | 1.13 | | 1.19 | 0.32 | 1.26 | 0.52 | 1.29 | 0.22 | 1.37 | 0.14 |
| RGR of Rosette Diameter (time point 3) | 1.52 | 0.46 | 2.09 | 0.08 | 1.94 | 0.12 | 1.64 | 0.42 | 1.66 | 0.46 |
| RGR of Rosette Area (time point 8) | 1.15 | | | | 1.18 | 0.07 | 1.21 | 0.03 | 1.23 | 0.01 |

TABLE 62-continued

Improved growth rate, biomass, rosette diameter, rosette area, plot coverage, leaf number, petiole relative area, leaf blade area, blade relative area and harvest index in transgenic *arabidopsis* plants exogenously expressing BDL103-short (SEQ ID NO: 671) under favorable conditions

| Parameter (time point) | Event No. | | | | | | | | | |
|---|---|---|---|---|---|---|---|---|---|---|
| | 2353 A | 2353 P | 2357 A | 2357 P | 2359 A | 2359 P | 2360 A | 2360 P | 2361 A | 2361 P |
| RGR of Rosette Area (time point 3) | 1.34 | 0.34 | 2.01 | 0.04 | 1.58 | 0.34 | 1.77 | 0.11 | 2.15 | 0.25 |
| RGR of Plot Coverage (time point 8) | 1.15 | | | | 1.18 | 0.07 | 1.21 | 0.03 | 1.23 | 0.01 |
| RGR of Plot Coverage (time point 3) | 1.34 | 0.34 | 2.01 | 0.04 | 1.58 | 0.34 | 1.77 | 0.11 | 2.15 | 0.25 |
| RGR of Leaf Number (time point 8) | 1.19 | | | | | | | | | |
| RGR of Leaf Number (time point 3) | 1.22 | 0.63 | 1.42 | 0.56 | 2.51 | 0.13 | 1.75 | 0.25 | 3.70 | 0.00 |
| Plot Coverage (time point 8) | 1.48 | | 1.29 | 0.10 | | | 1.35 | 0.37 | 1.17 | 0.19 |
| Plot Coverage (time point 5) | 1.34 | 0.00 | 1.21 | 0.06 | | | 1.18 | 0.58 | | |
| Plot Coverage (time point 3) | 1.39 | 0.09 | 1.49 | 0.06 | | | 1.33 | 0.61 | 1.11 | 0.75 |
| Plot Coverage (time point 1) | 1.20 | 0.06 | | | | | | | | |
| Petiole Relative Area (time point 8) | | | | | 1.21 | 0.71 | 1.92 | 0.25 | 3.37 | 0.44 |
| Petiole Relative Area (time point 5) | | | | | | | | | 1.20 | 0.25 |
| Petiole Relative Area (time point 1) | | | | | 1.31 | 0.20 | | | 1.75 | 0.01 |
| Leaf Petiole Area (time point 8) | | | | | 1.32 | 0.60 | 2.47 | 0.32 | 3.96 | 0.43 |
| Leaf Petiole Area (time point 5) | | | | | | | | | 1.20 | 0.38 |
| Leaf Petiole Area (time point 1) | | | | | 1.24 | 0.02 | | | 1.96 | 0.21 |
| Leaf Number (time point 8) | 1.15 | | | | | | | | | |
| Leaf Number (time point 5) | 1.12 | 0.01 | 1.21 | 0.00 | 1.08 | 0.05 | | | | |
| Leaf Number (time point 3) | 1.31 | 0.09 | 1.32 | 0.11 | 1.19 | 0.29 | 1.28 | 0.45 | 1.15 | 0.63 |
| Leaf Number (time point 1) | 1.26 | 0.01 | 1.21 | 0.23 | | | | | | |
| Leaf Blade Area (time point 8) | 1.29 | | 1.33 | 0.05 | 1.08 | 0.05 | 1.22 | 0.39 | | |
| Leaf Blade Area (time point 5) | 1.21 | 0.01 | 1.10 | 0.03 | | | 1.11 | 0.63 | | |
| Leaf Blade Area (time point 3) | 1.22 | 0.16 | 1.42 | 0.02 | | | | | | |
| Harvest index | 1.30 | 0.44 | | | | | | | | |
| Blade Relative Area (time point 5) | | | 1.04 | 0.07 | | | | | | |
| Blade Relative Area (time point 3) | 1.15 | 0.16 | 1.19 | 0.09 | 1.10 | 0.28 | | | | |

Table 62. Analysis of growth parameters in a greenhouse assay of transgenic plants overexpressing BDL103-short polynucleotide (SEQ ID NO: 671) under the regulation of a constitutive promoter (35S; SEQ ID NO: 675) which were grown until seed production under normal conditions (as described in Example 7 above). Each event number refers to an independent transformation event in a plant (i.e., generation of a transgenic plant expressing the polynucleotide of choice). "A" = average; "P" = p-value; "RGR" = relative growth rate; "gr" = grams; yield is presented in mg/plant; Rosette Diameter is presented in cm/plant; Rosette Area is presented in $cm^2$/plant; RGR of Rosette Diameter is presented in cm/plant*day; RGR of Rosette Area is presented in $cm^2$/plant*day; RGR of Plot Coverage is presented in $cm^2$/plant*day; RGR of Leaf Number is presented in 1/day; Plot Coverage is presented in $cm^2$; Petiole Relative Area is presented in percent; Leaf Petiole Area is presented in $cm^2$; Leaf Number is presented as number of leaves per plant; Leaf Blade Area is presented in $cm^2$; Harvest Index is presented in g/DW (dry weight); Blade Relative Area is presented in percent; The various time points indicate days from beginning of experiment in which parameters were measured.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08952218B2). An electronic copy of the "Sequence Listing" will also be available from the USPTO upon request and payment of the fee set forth in 37 CFR 1.19(b)(3).

What is claimed is:

1. A method of improving an agronomic trait selected from the group consisting of: root coverage, root length, leaf area, rosette diameter, rosette area, plot coverage, leaf number, growth rate of root length, growth rate of root coverage, growth rate of rosette area, growth rate of rosette diameter and growth rate of plot coverage of a plant as compared to a native plant which is grown under the same growth conditions, comprising:
    (a) expressing within the plant an exogenous polynucleotide comprising the nucleic acid sequence set forth in SEQ ID NO:619 or 16, and
    (b) selecting plants resultant of step (a) for an increased root coverage, increased root length, increased leaf area, increased rosette diameter, increased rosette area, increased plot coverage, increased leaf number, increased growth rate of root length, increased growth rate of root coverage, increased growth rate of rosette area, increased growth rate of rosette diameter, or increased growth rate of plot coverage as compared to a native plant which is grown under the same growth conditions, thereby improving the agronomic trait selected from the group consisting of: root coverage, root length, leaf area, rosette diameter, rosette area, plot coverage, leaf number, growth rate of root length, growth rate of root coverage, growth rate of rosette area, growth rate of rosette diameter and growth rate of plot coverage of the plant as compared to the native plant which is grown under the same growth conditions.

2. A method of improving an agronomic trait selected from the group consisting of: root coverage, root length, leaf area, rosette diameter, rosette area, plot coverage, leaf number, growth rate of root length, growth rate of root coverage, growth rate of rosette area, growth rate of rosette diameter, and growth rate of plot coverage of a plant as compared to a native plant which is grown under the same growth conditions, comprising:
    (a) expressing within the plant an exogenous polynucleotide comprising a nucleic acid sequence encoding the polypeptide set forth in SEQ ID NO:75 or an orthologue thereof, said orthologue having at least 88% sequence identity to the polypeptide set forth in SEQ ID NO:75, and
    (b) selecting plants resultant of step (a) for an increased root coverage, increased root length, increased leaf area, increased rosette diameter, increased rosette area, increased plot coverage, increased leaf number, increased growth rate of root length, increased growth rate of root coverage, increased growth rate of rosette area, increased growth rate of rosette diameter, or increased growth rate of plot coverage as compared to a native plant which is grown under the same growth conditions, thereby improving the agronomic trait selected from the group consisting of: root coverage, root length, leaf area, rosette diameter, rosette area, plot coverage, leaf number, growth rate of root length, growth rate of root coverage, growth rate of rosette area, growth rate of rosette diameter, and growth rate of plot coverage of the plant as compared to the native plant which is grown under the same growth conditions.

3. The method of claim 2, wherein said polypeptide is set forth in SEQ ID NO:75.

4. The method of claim 2, wherein said nucleic acid sequence is set forth in SEQ ID NO:619 or 16.

5. The method of claim 2, wherein said orthologue is isolated from a plant selected from the group consisting of barley, *arabidopsis*, maize, cotton, oilseed rape, rice, sugar cane, *sorghum*, soybean, sunflower, tomato, switchgrass, and wheat.

6. A method of producing a crop comprising: (a) selecting a parent plant transformed with an exogenous polynucleotide encoding the polypeptide set forth in SEQ ID NO:75 or an orthologue thereof, wherein said orthologue has at least 88% sequence identity to the polypeptide set forth in SEQ ID NO:75 for an increased root coverage, increased root length, increased leaf area, increased rosette diameter, increased rosette area, increased plot coverage, increased leaf number, increased growth rate of root length, increased growth rate of root coverage, increased growth rate of rosette area, increased growth rate of rosette diameter, or increased growth rate of plot coverage as compared to a native plant of the same species which is grown under the same conditions, and (b) growing progeny crop plant of said parent plant, wherein said progeny crop plant has said increased root coverage, said increased root length, said increased leaf area, said increased rosette diameter, said increased rosette area, said increased plot coverage, said increased leaf number, said increased growth rate of root length, said increased growth rate of root coverage, said increased growth rate of rosette area, said increased growth rate of rosette diameter, or said increased growth rate of plot coverage, wherein said progeny crop comprises the exogenous polynucleotide, thereby producing the crop.

7. The method of claim 6, wherein said growing said crop plant is under non-stress conditions.

8. The method of claim 6, wherein said growing said crop plant is under nitrogen deficient conditions.

9. The method of claim 2, wherein said orthologue is set forth in SEQ ID NO: 519, 520, 521, or 522.

10. The method of claim 6, wherein said orthologue is set forth in SEQ ID NO: 519, 520, 521, or 522.

11. A method of producing a transgenic plant, comprising:
    (a) expressing within the plant an exogenous polynucleotide comprising the nucleic acid sequence set forth in SEQ ID NO:619 or 16, and (b) selecting plants resultant of step (a) for an increased root coverage under nitrogen limiting conditions as compared to a native plant which is grown under the same growth conditions, thereby producing the transgenic plant.

12. A method of producing a transgenic plant, comprising:
(a) expressing within the plant an exogenous polynucleotide comprising a nucleic acid sequence encoding the polypeptide set forth in SEQ ID NO:75 or an orthologue thereof, said orthologue has at least 88% sequence identity to the polypeptide set forth in SEQ ID NO:75, and
(b) selecting plants resultant of step (a) for an increased root coverage under nitrogen limiting conditions as compared to a native plant which is grown under the same growth conditions, thereby producing the transgenic plant.

13. A method of producing a crop comprising: (a) selecting a parent plant transformed with an exogenous polynucleotide encoding the polypeptide set forth in SEQ ID NO:75 or an orthologue thereof, wherein said orthologue has at least 88% sequence identity to the polypeptide set forth in SEQ ID NO:75 for an increased root coverage under nitrogen limiting conditions as compared to a native plant of the same species which is grown under the same growth conditions, and (b) growing progeny crop plant of said parent plant, said progeny crop plant has said increased root coverage, wherein said progeny crop comprises the exogenous polynucleotide, thereby producing the crop.

14. The method of claim 13, wherein said polypeptide is set forth in SEQ ID NO:75.

15. The method of claim 1, wherein said selecting is under non-stress conditions.

16. The method of claim 2, wherein said selecting is under non-stress conditions.

17. The method of claim 6, wherein said growing said crop plant is under non-stress conditions.

18. The method of claim 6, wherein said growing said crop is under nitrogen limiting conditions.

19. A method of improving an agronomic trait selected from the group consisting of: root coverage, root length, leaf area, rosette diameter, rosette area, plot coverage, leaf number, growth rate of root length, growth rate of root coverage, growth rate of rosette area, growth rate of rosette diameter, and growth rate of plot coverage of a plant as compared to a native plant which is grown under the same growth conditions, comprising:
(a) expressing within the plant an exogenous polynucleotide comprising a nucleic acid sequence encoding the polypeptide selected from the group consisting of SEQ ID NOs: 75, and 517-523, and
(b) selecting plants resultant of step (a) for an increased root coverage, increased root length, increased leaf area, increased rosette diameter, increased rosette area, increased plot coverage, increased leaf number, increased growth rate of root length, increased growth rate of root coverage, increased growth rate of rosette area, increased growth rate of rosette diameter, or increased growth rate of plot coverage as compared to a native plant which is grown under the same growth conditions, thereby improving the agronomic trait selected from the group consisting of: root coverage, root length, leaf area, rosette diameter, rosette area, plot coverage, leaf number, growth rate of root length, growth rate of root coverage, growth rate of rosette area, growth rate of rosette diameter, and growth rate of plot coverage of the plant as compared to the native plant which is grown under the same growth conditions.

20. A method of producing seeds of a crop comprising: (a) selecting a parent plant transformed with an exogenous polynucleotide comprising a nucleic acid sequence encoding the polypeptide set forth in SEQ ID NO:75 or an orthologue thereof, wherein said orthologue has at least 88% sequence identity to the polypeptide set forth in SEQ ID NO:75 for an increased root coverage, increased root length, increased leaf area, increased rosette diameter, increased rosette area, increased plot coverage, increased leaf number, increased growth rate of root length, increased growth rate of root coverage, increased growth rate of rosette area, increased growth rate of rosette diameter, or increased growth rate of plot coverage as compared to a native plant of the same species which is grown under the same conditions, (b) growing a seed producing crop plant from said parent plant resultant of step (a), wherein said seed producing crop plant comprises said exogenous polynucleotide and has said increased root coverage, said increased root length, said increased leaf area, said increased rosette diameter, said increased rosette area, said increased plot coverage, said increased leaf number, said increased growth rate of root length, said increased growth rate of root coverage, said increased growth rate of rosette area, said increased growth rate of rosette diameter, or said increased growth rate of plot coverage, and (c) producing seeds from said seed producing crop plant resultant of step (b), thereby producing seeds of the crop.

21. The method of claim 20, wherein said orthologue is set forth in SEQ ID NO: 519, 520, 521, or 522.

\* \* \* \* \*